United States Patent
Miki et al.

(10) Patent No.: US 7,396,978 B2
(45) Date of Patent: Jul. 8, 2008

(54) SEED COAT GENE AND GENE PRODUCT

(75) Inventors: Brian Miki, Ottawa (CA); Mark Gijzen, London (CA); Shea Miller, Ottawa (CA)

(73) Assignee: Her Majesty the Queen in right of Canada, as represented by the Minister of Agriculture and Agri-Food, Ottawa Ontario (CA)

( * ) Notice: Subject to any disclaimer, the term of this patent is extended or adjusted under 35 U.S.C. 154(b) by 206 days.

(21) Appl. No.: 10/861,875

(22) Filed: Jun. 4, 2004

(65) Prior Publication Data

US 2005/0034195 A1    Feb. 10, 2005

Related U.S. Application Data

(60) Division of application No. 09/673,333, filed as application No. PCT/CA99/00293 on Apr. 13, 1999, now abandoned, which is a continuation-in-part of application No. 08/441,597, filed on May 15, 1995, now Pat. No. 5,824,863.

(51) Int. Cl.
| | |
|---|---|
| C12N 15/82 | (2006.01) |
| C12N 15/29 | (2006.01) |
| A01H 5/00 | (2006.01) |
| A01H 5/10 | (2006.01) |

(52) U.S. Cl. .................. 800/278; 800/298; 536/23.6; 435/419; 435/320.1

(58) Field of Classification Search ................ 536/23.6; 435/320.1, 419; 800/298
See application file for complete search history.

(56) References Cited

U.S. PATENT DOCUMENTS 5,569,834 A * 10/1996 Hinchee et al. ............. 800/312

FOREIGN PATENT DOCUMENTS

| CA | 2186833 | 3/1998 |
|---|---|---|
| CA | 2211018 | 3/1998 |
| WO | WO 91/09957 | 7/1991 |
| WO | WO 97/15656 | 5/1997 |

OTHER PUBLICATIONS

Odani S. et al. Soybean hydrophobic protein. Isolation, partial characterization and the complete primary structure. Eur J Biochem. Feb. 2, 1987;162(3):485-91.*
Whisstock J.C. et al. Prediction of protein function from protein sequence and structure. Q Rev Biophys. Aug. 2003;36(3):307-40. Review.*
Christou P. et al. Inheritance and expression of foreign genes in transgenic soybean plants. Proc Natl Acad Sci U S A. Oct. 1989;86(19):7500-7504.*
Hattori, J. et al., "A conserved BURP domain defines a novel group of plant proteins with unusual primary structures," *Molecular Gen. Genet.*, 259:424-428 (1998).
Colombo, L. et al., "Downregulation of Ovule-Specific MADS Box Genes from Petunia Results in Maternally Controlled Defects in Seed Development," *Plant Cell*, 9:703-715 (1997).
Sabala, I. et al., "A spruce gene, af70, constitutively expressed in somatic embryos and induced by ABA and low temperature in seedlings," *Physiologia Plantarum*, 99:316-22 (1997).
Tornero, P. et al, "Identification of a New Pathogen-Induced Member of the Subtilisin-like Processing Protease Family from Plants," *Journal of Biological Chemistry*, 272:4412-19 (1997).
Solinas, G. et al., Cloning of three cDNA's encoding novel myb (accession Nos. Y11352, Y11415 and Y113510 from anaerobically treated rice coleoptiles (PGR 97-069), *Plant Physiol.*, 114:395 (1997).
Siezen, Roland J. and Leunissen, Jack A. M., "Subtilases: The superfamily of subtilisin-like serine proteases," *Protein Science*, 6:501-23 (1996).
Sabala, I. et al., "Characterization of a spruce gene constitutively expresses in somatic embryos and induced by ABA and low temperature in seedlings," *Eur. Bioinformatics Inst.*, 48:(1996).
Barrett, Alan J. and Rawlings, Neil D., "Perspectives in Biochemistry and Biophysics: Families and Clans of Serine Peptidases," *Archives of Biochemistry and Biophysics*, 318:247-50 (1995).
Ribeiro, A. et al., "A Nodule-Specific Gene Encoding a Subtilisin-Like Protease is Expressed in Early Stages of Actinorhizal Nodule Development," *Plant Cell*, 7:785-794 (1995).
Weber, Hans et al., "Seed Coat-Associated Invertases of Fava Bean Control Both Unloading and Storage Functions: Cloning of cDNAs and Cell Type-Specific Expression," *Plant Cell*, 7:1835-46 (1995).
Yamagata, Hiroshi et al., "Cucumisin, a Serine Protease from Melon Fruits, Shares Structural Homology with Subsilisin and Is Generated from a Large Precursor," *Journal of Biological Chemistry*, 269:32725-32731 (1994).
Wang, Chang-Sheng and Vodkin, Lila O., "Extraction of RNA from Tissues Containing High Levels of Procyanidins that Bind RNA," *Plant Molecular Biology Reporter*, 12:132-145 (1994).
Fobert, Pierre R. et al., "T-DNA tagging of a seed coat-specific cryptic promoter in tobacco," *Plant Journal* 6:567-77 (1994).
Capel, J. et al., "No-random distribution of transposable elements in the nuclear genome of plants," *Nucleic Acids Research*, 21:2369-73 (1993).
Yamaguchi-Shinozaki, Kazuko and Shinozaki, Kazuo, "The plant hormone abscisic acid mediates the drought-induced expression but not the seed-specific expression of rd22, a gene responsive to dehydration stress in *Arabidopsis thaliana*," *Mol. Gen. Genet.*, 238:17-25 (1993).
Datta, N. et al., "Isolation and characterization of three families of auxin down-regulated cDNA clones," *Plant Molecular Biology*, 21:859-69 (1993).
Lindsey, K. et al., "Tagging genomic sequences that direct transgene expression by activation of a promoter trap in plants," *Transgenic Research*, 2:33-47 (1993).

(Continued)

*Primary Examiner*—Cynthia Collins
(74) *Attorney, Agent, or Firm*—Heslin Rothenberg Farley & Mesiti PC

(57) ABSTRACT

The present invention is directed to a nucleic acid comprising a nucleotide sequence that encodes a protein that imparts a dull luster to a seed coat when expressed within seed-coat tissues and to transgenic seeds, plant cells and plants expressing the protein.

12 Claims, 44 Drawing Sheets

OTHER PUBLICATIONS

Covello, Patrick S. and Gray, Michael W., "Silent mitochondrial and active nuclear genes for subunit 2 of cytochrome *c* oxidase (*cox2*) in soybean: evidence for RNA-mediated gene transfer," *The EMBO Journal*, 11:3815-20 (1992).

Irniger, S. et al., "The yeast actin intron contains a cryptic promoter that can be switched on be preventing transcriptional interference," *Nucleic Acids Research, Institute of Microbiology, Swiss Federal Institute of Technology*, Zürich, Switzerland, 20:2733-39 (1992).

Fourel, Geneviève et al., "Expression of the Woodchuck N-*myc2* Retroposon in Brain and in Liver Tumors is Driven by a Cryptic N-*myc* Promoter," *Molecular and Cellular Biology*, 12:5336-44 (1992).

Gottlob-McHugh, Sylvia G. et al., "Normal Growth of Transgenic Tobacco Plants in the Absence of Cytosolic Pyruvate Kinase," *Plant Physiol.*, 100:820-25 (1992).

Zheng, Liansheng et al., "The β Subunit of Tomato Fruit Polygalacturonase Isoenzyme 1: Isolation, Characterization, and Identification of Unique Structural Features," *Plant Cell*, 4:1147-1156 (1992).

Ouellet, Thérèse, Rutledge, Robert G. and Miki, Brian L., "Members of the acetohydroxyacid synthase multigene family of *Brassica napus* have divergent patterns of expression," *Plant Journal*, 2:321-330 (1992).

Koncz, C. et al., "T-DNA insertional mutagenesis in *Arabidopsis*," *Plant Molecular Biology*, 20:963-76 (1992).

Breyene, P. et al., "Characterization of a Plant Scaffold Attachment Region in a DNA Fragment that Normalizes Transgene Expression in Tobacco," *Plant Cell*, 4:463-71 (1992).

Al-Shawi, R. et al., "The Herpes Simplex Virus Type 1 Thymidine Kinase is Expressed in the Testes of Transgenic Mice under the Control of a Cryptic Promoter," *Mol. and Cellular Biology*, 11:4207-16 (1991).

Feldmann, Kenneth A., "T-DNA insertion mutagenesis in *Arabidopsis*; mutational spectrum," *Plant Journal*, 1:71-82 (1991).

Kertbundit, S. et al., "In vivo random β-glucuronidase gene fusions in *Arabidopsis thaliana*," *Proc. Natl. Acad. Sci. USA*, 88:5212-16 (1991).

Nugent, Jacqueline M. and Palmer, Jeffrey D., "RNA-Mediated Transfer of the Gene *coxII* from the Mitochondrion to the Nucleus during Flowering Plant Evolution," *Cell*, 66:473-481 (1991).

Gheysen, Godelieve, Villarroel, Raimundo and VanMontagu, Marc, "Illegitimate recombination in plants: a model for T-DNA integration," *Genes & Development*, 5:287-97 (1991).

Takahashi, Nobuo et al., "Activation and Suppression of a Cryptic Promoter in the Intron of the Human Melanoma-associated ME491 Antigen Gene," *Jpn. Journal Cancer Res.*, 82:1239-44 (1991).

Rutledge, R. G. et al., "Molecular characterization and genetic origin of the *Brassica napus* acetohydroxyacid synthase multigene family," *Mol. Gen. Genet.*, 229:31-40 (1991).

Palmer, Jeffrey D., "Plastid Chromosomes: Structure and Evolution," *Molecular Biology of Plasmids*, Bogorad, L and Vasil, I.K., eds., Chapter 2:5-53 (1991).

Fobert, Pierre R., Miki, Brian L. and Iyer, V. N., "Detection of gene regulatory signals in plants revealed by T-DNA-mediated fusions," *Plant Molecular Biology*, 17: 837-851 (1991).

Bäumlein, Helmut et al., "A novel seed protein gene from *Vicia faba* is developmentally regulated in transgenic tobacco and *Arabidopsis* plants," *Mol. Gen. Genet.*, 225:459-67 (1991).

Walden, R. et al., "T-DNA as a gene tag," *Plant Journal*, 1:281-288 (1991).

Van Lijsebettens, M. et al., "Insertional mutagenesis in *Arabidopsis thaliana*," *Plant Science*, 80:27-37 (1991).

van de Ven, Wim J. M., et al., "Furin is a subtilisin-like proprotein processing enzyme in higher eukaryotes," *Molecular Biology Reports*, 14:265-75 (1990).

Yanofsky, Martin F. et al., "The protein encoded by the *Arabidopsis* homeotic gene *agamous* resembles transcription factors," *Nature*, 346:36-39 (1990).

Kosugi, S. et al., "An Improved Assay for β-Glucuronidase in Transformed Cells: Methanol Almost Completely Suppresses a Putative Endogenous β-Glucuronidase Activity," *Plant Science*, 70:133-140 (1990).

Koltunow, A. et al., "Different Temporal and Spatial Gene Expression Patterns Occur during Anther Development," *Plant Cell*, 2:1201-24 (1990).

Gheysen, G. et al. "Cloning and sequence analysis of truncated T-DNA inserts fro *Nicotiana tabacum*," *Gene*, 94:155-63 (1990).

Baszczynski, Chris L. and Fallis, Lynne, "Isolation and nucleotide sequence of a genomic clone encoding a new *Brassica napus* napin gene," *Plant Molecular Biology*, 14:633-35 (1990).

Mizuno, K. et al., "Yeast *Kex2* Gene Encodes an Endopeptidase Homologous to Subtilisin-Like Serine Proteases," *Biochemical and Biophysical Research Communications*, 156:246-54 (1988).

Chen, Z.-L. et al., "A DNA sequence element that confers seed-specific enhancement to a constitutive promoter," *The EMBO Journal*, 7:297-302 (1988).

Moos, M. et al., "Reproducible High Yield Sequencing of Proteins Electrophoretically Separated and Transferred to an Inert Support," *Journal of Biological Chemistry*, 263:6005-8 (1988).

Sanders, P. R. et al., "Comparison of cauliflower mosaic virus 35S and nopaline synthase promoters in transgenic plants," *Nucleic Acids Research, Plant Molecular Biology Group*, MO USA, 15:1543-58 (1987).

Odani, S. et al., "Soybean hydrophobic protein: Isolation, partial characterization and the complete primary structure," *Eur. J. Biochem.*, 162:485-91 (1987).

Joshi, C. P., "An Inspection of the domain between putative TATA box and translation start site in 79 plant genes," *Nucleic Acids Research, Division of Biochemical Sciences, National Chemical Laboratory*, India, 15:6643-53 (1987).

Jefferson, Richard A., "Assaying Chimeric Genes in Plants: The GUS Gene Fusion System," *Plant Molecular Biology Reporter*, 5:387-405 (1987).

Blum, Helmut et al., "Improved silver staining of plant proteins, RNA and DNA in polyacrylamide gels," *Electrophoresis, Institut für Biochemie*, 8:93-99 (1987).

Gheysen, Godelieve, VanMotagu, Marc and Zambryski, Patricia, "Integration of *Agrobacterium tumefaciens* transfer DNA (T-DNA) involves rearrangements of target plant DNA sequences," *Proc. Natl. Acad. Sci. USA*, 84:6169-73 (1987).

Power, Scott D. et al. "Secretion and autoproteolytic maturation of subtilisin," *Proc. Natl. Acad. Sci. USA*, 83:3096-3100, (1986).

Gasser, Susan and Laemmli, Ulrich K., "Cohabitation of Scaffold Binding Regions with Upstream/Enhancer Elements of Three Developmentally Regulated Genes of *D. melanogaster*," *Cell*, 46:521-30 (1986).

Fling, Steven P. and Gregerson, Dale S., "Peptide and Protein Molecular Weight Determination by Electrophoresis Using a High-Molarity Tris Buffer System without Urea," *Analytical Biochemistry*, 155:83-88 (1985).

Rhodes, P. R. and Vodkin, L. O., "Highly structured sequence homology between an insertion element and the gene in which it resides," *Proc. Natl. Acad. Sci. USA*, 82:493-97 (1985).

Okamuro, Jack K. and Goldberg, Robert B., "Tobacco single-copy DNA is highly homologous to sequences present in the genomes of its diploid progenitors," *Mol. Gen. Genet.*, 198:290-298 (1985).

Bevan, Michael, "Binary *Agrobaceterium* vectors for plant transformation," *Nucleic Acids Research: Plant Breeding Institute*, Cambridge, UK, 12:8711-21 (1984).

Pickett, James W., "Recognition of protein coding regions in DNA sequences," *Nucleic Acids Research: Theoretical Division, Los Alamos National Laboratory*, NM, USA, 10:5303-18 (1982).

\* cited by examiner

```
                                                    1    2
         XbaI                                        ┌───┐
    1    TCTAGACTTGTCTTTTCTTTACATAATCCTCTTCTTCTTTTTTTGTTAGTTTCTTCTGT

61    TTTATCCAAAAAACGAATTATTGATTAAGAAATACACCAGACAAGTTTTTTACTTCTTTT
         ┌1──┐2
  121    TCTTTTTTTTTTGTGGTAAAAAATTACACCTGGACAAGTTTATCACGAAAATGAAAATT
                                                            8
  181    GCTATTTAAGGGATGTAGTTCCGGACTATTTGGAAGATAAGTGTTAACAAAATAAATAAA
                      6  3                              7
                      ┌──┐──────┐                       ┌──┐4
  241    TAAAAAGTTTATACAGTTAGATCTCTCTATAACAGTCATCCTTATTTATAACAATACTTT
         7
         ┌4─┐                                    4       3
  301    ACTATAACCGTCAAATTTATTTTGAAACAAAATTTTCATGTTATGTTACTATAACAGTAT
                                              ←──6──┐
  361    TTTATTATAGCAACCAAAAAATATCGAAACAGATACGATTGTTATAGAGCGATTTGATTG
                                     SnaB1
  421    TATCATTATCCACATATTTTCGTAAGCCCAATTACTCCTCCTACGTACGATGAAAGTAAA

481    CCAATTTAAAGTTGCAAAAATCCAATAGATTTCAATACTTCTTCAACTGGCGTTATGTTA

541    GGTAATGACTCCTTTTTAACTTTTCATCTTTAATTTGAAGTTTCTTTCATTAAAAGAAAG
         5───XbaI───→                              5───XbaI───→
  601    TTTCTAGAAGAGAAGTGTTTTAACACTTCTAGCTCTACTATTATCTGTGTTTCTAGAAGA
                                                                 ←─8─
  661    AAAATAGAAAATGTGTCCACCTCAAAAACAACTAAAGGTGG┌GCAAATCTC┐CACCTATTTA
         ←──┐       ←───7───┐
  721    TTTTATTTTGGATTAATTAAGATATAGTAAAGATCAG┌TTATAAACG┐GAGTTTTGAGTTGA

781    TACAG┌TGAATTTTAAG┐ATGTGTACCGATTTAACTTTATTTACATTTATGTTTCGCACATA
         TATA                    ↓
  841    TAAGAAGTCCGATTTGGAAATACTAGATTTTGTCAATCAGGCAATTCATGTGGTTGAAGA

901    ATTTAAGTTATATACAATGATGATATAAAGAATTTTTATACTATTAGTGCAAATTAATCG

957    ATTACTAAAAATTATTATTCTATTAATTTATGCTATC│GTGCCTCCCCAACCCGTCGACC
                                              │ATATCAAATTTAGTATTCCTTT
                                              *
 1005    GCGGTACCCGGTGGTCAGTCCCTT ATG TTA CGT CCT GTA GAA ACC CCA ACC
                                   M   L   R   P   V   E   T   P   T
```

FIGURE 6

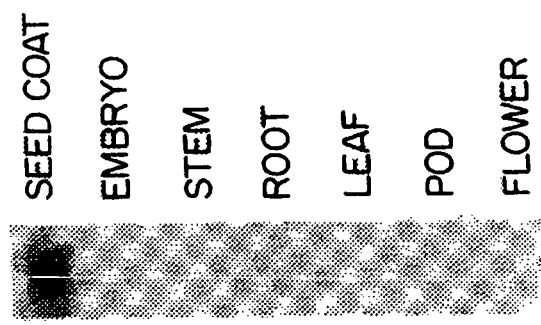
FIG. 10A
FIG. 10B
FIG. 10C
FIG. 10D

RESTRICTION MAP OF SC21

1 kb

Restriction map of sc4
The shaded and open boxes represent exons and introns respectively.

```
TAAGCTTTCAAGAGACAAACTGCTTTGAAAAATGGGATCCAAGGTTGTTGCATCCGTTGC    60
                                  M  G  S  K  V  V  A  S  V  A    10

CCTTCTCCTCTCCATCAACATTCTTTTCATTTCCATGGTTAGCTCCAGCAGCCACTACGA   120
 L  L  L  S  I  N  I  L  F  I  S  M  V  S  S  S  H  Y  D         30

TCCACAGCCCCAACCTTCTCACGTCACTGCTCTTATTACACGACCTAGTTGTCCGGATCT   180
 P  Q  P  Q  P  S  H  V  T  A  L  I  T  R  P  S  C  P  D  L      50

GAGTATTTGCCTCAATATTTTAGGCGGGTCTCTAGGAACCGTGGATGATTGTTGTGCCCT   240
 S  I  C  L  N  I  L  G  G  S  L  G  T  V  D  D  C  C  A  L      70

CATCGGTGGTCTTGGTGACATTGAAGCCATTGTGTGCCTTTGCATCCAACTCAGGGCCCT   300
 I  G  G  L  G  D  I  E  A  I  V  C  L  C  I  Q  L  R  A  L      90

CGGAATATTAAACCTTAACCGTAATTTGCAGTTAATATTAAACTCCTGTGGACGAAGCTA   360
 G  I  L  N  L  N  R  N  L  Q  L  I  L  N  S  C  G  R  S  Y     110

CCCGTCAAACGCCACTTGCCCCCGAACCTAAGAACAGAATATGTATGGCACTAATTACCA   420
 P  S  N  A  T  C  P  R  T  *                                   119

TATTACTTCGTATCATGGTGTTTGTTTGTTTGTCTGTGTTTAAAGTTAAGGATGTTATAC   480

CCTTCGTGCCTGCTACATATATATAGTGGGCACTATAATATTACCAATAAATTAACGTCC   540

ATATATAAGAATAATAATAAATAAATAAATATTTCTATACAAATAAAGGTTACGTAATGT   600

TGTTGTTCTCGTGGATGGGGATCTTATCTTCCTCCTCGCTATCTTTGTTTATCGTATTTC   660

AGTGAAAGTTGTTCAATAAAAGTCCTTTGTTCAACAAGT(A)ₙ                    700
```

*FIGURE 15(A)*

MGSKVVASVALLLSINILFISMVSS 25
SSHYDPQPQPSHVTALITRPSCPDL 50
SICLNILGGSLGTVDDCCALIGGLG 75
DIEAIVCLCIQLRALGILNLNRNLQ 100
LILNSCGRSYPSNATCPRT 119
FIG. 15(B)
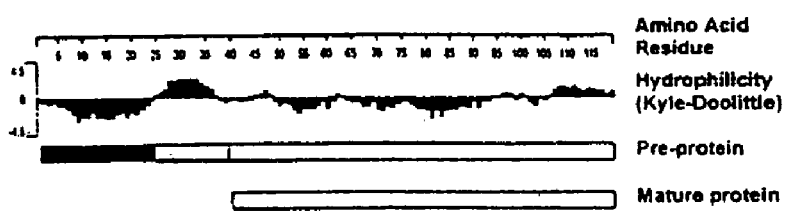
FIG. 15(C)
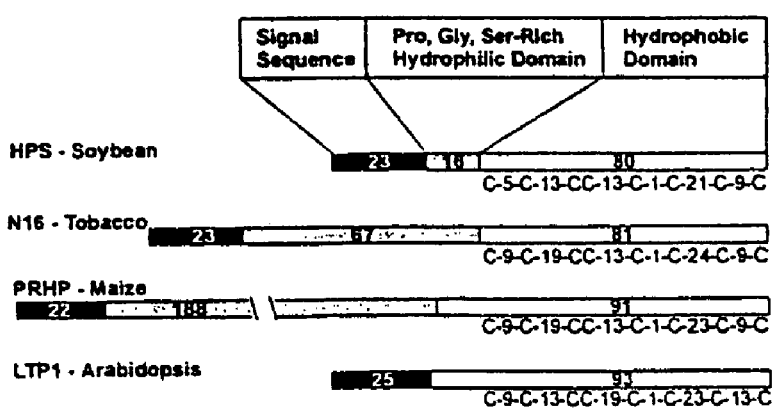
FIG. 15(D)
FIG. 15

CULTIVAR: CLARK    WILLIAMS 82
PHENOTYPE: DULL    SHINY
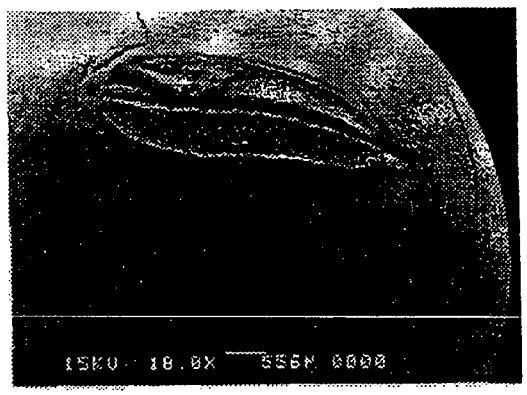 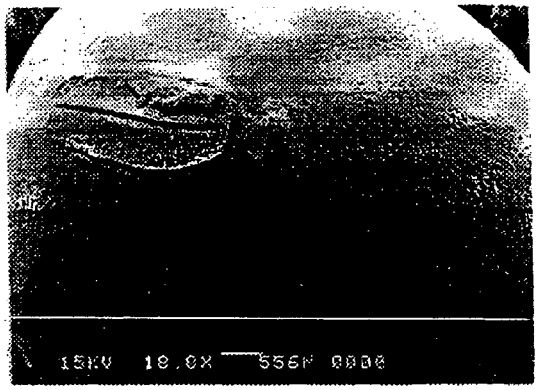
FIG. 16A
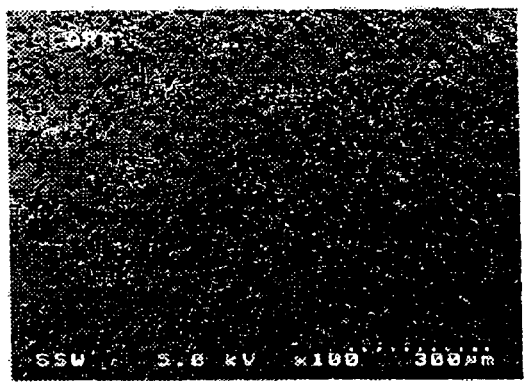 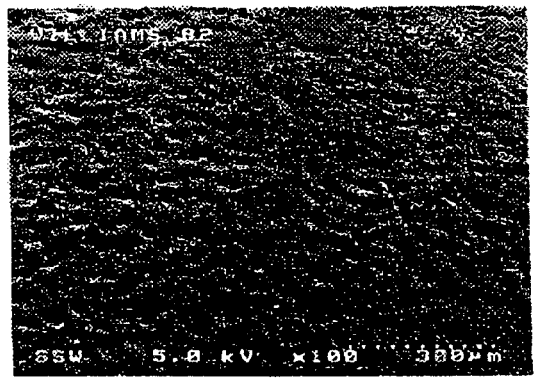
FIG. 16B
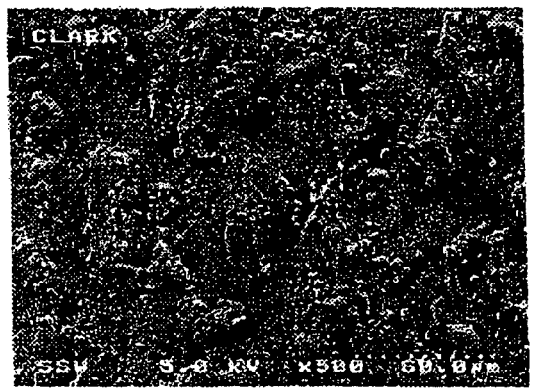 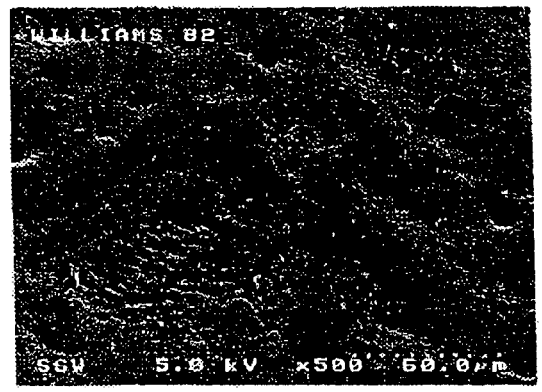
FIG. 16C

```
   --C AAT GCT GCG TTA ACT CCT AGA CAT TAC TGG GAA ACG ATG CTT CCA AGA ACT CCC   55
       N   A   A   L   T   P   R   H   Y   W   E   T   M   L   P   R   T   P    18

TTG CCG AAA GCA ATC ACA GAG CTA CTA AGC CTT GAA AGT AGG TCC ATA TTT GAA TAT  112
 L   P   K   A   I   T   E   L   L   S   L   E   S   R   S   I   F   E   Y    37

GCC GGG AAT GAT GAC CAG TCA GAA AGT AGG TCC ATA TTA GGA TAC GCT GGC TAT AAT  169
 A   G   N   D   D   Q   S   E   S   R   S   I   L   G   Y   A   G   Y   N    56

CAA GAC GAG GAT GAT GTG AGC AAA CAC AAT ATA CAA ATC TTC AAC AGG TTG TTT TTC  226
 Q   D   E   D   D   V   S   K   H   N   I   Q   I   F   N   R   L   F   F    75

TTG GAA GAG GAC CTG CGT GCT GGC AAA ATA TTC AAC ATG AAG TTC GTC AAC AAC ACA  283
 L   E   E   D   L   R   A   G   K   I   F   N   M   K   F   V   N   N   T    94

AAA GCC ACA GTC CCG TTG CTA CCG CGC CAA ATT TCG AAA CAA ATA CCG TTC TCA GAA  340
 K   A   T   V   P   L   L   P   R   Q   I   S   K   Q   I   P   F   S   E   113

GAT AAA AAG AAG CAA GTG TTG GCG ATG CTT GGC GTG GAA GCG AAC TCA AGC AAC GCC  397
 D   K   K   K   Q   V   L   A   M   L   G   V   E   A   N   S   S   N   A   132

AAG ATC ATA GCG GAG ACC ATT GGT CTT TGC CAA GAG CCT GCA ACG GAG GGA GAA AGG  454
 K   I   I   A   E   T   I   G   L   C   Q   E   P   A   T   E   G   E   R   151

AAA CAC TGC GCG ACT TCG TTG GAG TCC ATG GTT GAT TTC GTC GTT TCC GCG CTC GGG  511
 K   H   C   A   T   S   L   E   S   M   V   D   F   V   V   S   A   L   G   170

AAG AAC GTT GGT GCT TTC TCA ACA GAG AAA GAA AGG GAA ACT GAG TCT GGA AAG TTT  568
 K   N   V   G   A   F   S   T   E   K   E   R   E   T   E   S   G   K   F   189

GTA GTG GTG AAA AAT GGG GTG AGG AAG TTG GGA GAT GAT AAG GTT ATT GCC TGT CAT  625
 V   V   V   K   N   G   V   R   K   L   G   D   D   K   V   I   A   C   H   208

CCA ATG AGT TAC CCT TAT GTT GTG TTT GGG TGT CAT CTA GTG CCA AGG AGT AGC GGG  682
 P   M   S   Y   P   Y   V   V   F   G   C   H   L   V   P   R   S   S   G   227

TAT TTG GTG CGC TTG AAG GGA GAA GAT GGG GTT CGA GTG AAA GCA GTT GTT GCG TGC  739
 Y   L   V   R   L   K   G   E   D   G   V   R   V   K   A   V   V   A   C   246

CAC AGA GAC ACG TCA AAG TGG GAC CAT AAT CAT GGG GCA TTC AAA GTG CTC AAT CTT  796
 H   R   D   T   S   K   W   D   H   N   H   G   A   F   K   V   L   N   L   265

AAG CCT GGG AAT GGT ACA GTA TGC CAT GTC TTC ACT GAG GGG AAT CTT CTT TGG CTT  853
 K   P   G   N   G   T   V   C   H   V   F   T   E   G   N   L   L   W   L   284

CCA AAT TAG attaattaccatatacatatttgtccttgttctatccttaaataagtggaatcacctgaagaa  925
 P   N   *                                                                   286 ttgtgcgtaatgagttgtttgtctttgtggaaattgttatctgtcttgcatcaccaaataggtatatataaaata 1000 acaggagcgtggtattttgttgcacaaaaatggatttcaaccgatcaaaaaaatatagcctttaccaattagaagg 1075 gtttggctttgttagcaaataataaaaataaaatatcttgatgg(a)n                            1119
```

```
SC4c     FFLEEDLRAG KIFNMKFVNN --TKATVPLL PRQISKQIPF SEDKKKQVLA MLGVEANSSN 131
RD22     FFLEKDLVRG KEMNVRFNAE DGYGGKTAFL PRGEAETVPF GSEKFSETLK RFSVEAGSEE 235
PG1B     FFREKMLKSG TIMPMPDIK- -DKMPKRSFL PRVIASKLPF STSKIAELKK IFHAGDESQV 472
Sali3-2  FFYKEDLHPG KTMKVQFTKR ---------- --------PY AQPY--GVYT WLTDIKDTSK 215
USP      FF-EHDLHPG KNFNLGHTNS VGSIIR---- --------PF TKSR--QGVT --DSIWLANK 111
ADR6     FFYKEDLHPG KTMKVQFSKP ---------- --------PF QQPW--GVGT WLKEIKDTTK 111

SC4c     AKIIAETIGL CQE-PATEGE RKHCATSLES MVDFVVSALG KN-VGAFSTE KERETESGK- 188
RD22     AEMMKKTIEE C-EARKVSGE EKYCATSLES MVDFSVSKLG KYHVRAVSTE VAKKNAPMQK 294
PG1B     EKMIGDALSE C-ERAPSAGE TKRCVNSAED MIDFATSVLG RN-VVVRTTE DTKGSNGNIM 530
Sali3-2  EGYSFEEI-- CIKKEAFEGE EKFCAKSLGT VIGFAISKLG KN-IQVLSSS FVNKQE---- 168
USP      EKQSLEDF-- CYSPTAI-AE HKHCVSSLKS MIDQVISHFG STKIKAISSN FAPYQD---- 164
ADR6     EGYSFEEL-- CIKKEAIEGE EKFCAKSLGT VIGFAISKLG KN-IQVLSSS FVNKQD---- 164

SC4c     FVVVKNGVRK LGDDKVIACH PMSYPYVVFG CHLVPR-SSG YLVRLKGEDG VR-VKAVVAC 246
RD22     YKIAAAGVKK LSDDKSVVCH KQKYPFAVFY CHKAMM-TTV YAVPLEGENG MR-AKAVAVC 352
PG1B     I-GSVKGING GKVTKSVSCH QTLYPYLLYY CHSVPKVRVY EADILDPNSK VKINHGVAIC 589
Sali3-2  -QYTVEGVQN LG-DKAVMCH GLNFRTAVFY CHKV-RETTA FVVPLVAGDG TK-TQALAVC 224
USP      -QYVVEDVKK VG-DNAVMCH RLNFEKVVFN CHQV-RDTTA YVVSLVASDG TK-TKALTVC 220
ADR6     -QYTVEGVQN LG-DKAVMCH RLNFRTAVFY CHEV-RETTA FMVPLVAGDG TK-TQALAIC 220

SC4c     HRDTSKWDHN HGAFKVLNLK PGNGTVCHVF TEGNLLWLPN *                    286
RD22     HKNTSAWNPN HLAFKVLKVK PGTVPVCHFL PETHVVWFSY *                    392
PG1B     HVDTSSWGPS HGAFVALGSG PGKIEVCHWI FENDMTWAIA D*                           630
Sali3-2  HSDTSGMNH- HILHELMGVD PGTNPVCHFL GSKAILWVPN ISMDTAYQTN VVV*       276
USP      HHDTRGMNP- ELLYEALEVT PGTVPVCHFI GNKAAAWVPN HTADNLCVM*                   268
ADR6     HSNTSGMNH- QMLHQLMGVD PGTNPVCHFL GSKAILWVPN LSVDTAYQTN IVA*       272
```

B

```
SC4c     --NAALTPRL YWETMLPRTP LPKAITELLS L 29
RD22     AIAADLTPER YWSTALPNTP IPNSLHNLLT F 48
Sali3-2  HVHASLPEED YWEAVWPNTP IPTALRDVLK P 53
USP      GITATSSGED YWQSIWPNTP LPKTFSDLLI P 48
ADR6     ARESHARDED FWHAVWPNTP IPSSLRDLLK P 49
```

FIG. 19(B)

```
caaagttttaac ATG AAA GGC AAT AAT ACA CTT TTG TTG CAT TTA TTC TAC ACT ACT CTC   60
             M   K   G   N   N   T   L   L   L   H   L   F   Y   T   T   L    16

TTC CTG TTT CTT GTA GTG TCA AGT TCA TCT TCA ACA GGG AAT GAA AGT AAC GAT GAC   117
 F   L   F   L   V   V   S   S   S   S   S   T   G   N   E   S   N   D   D    35

ACT AAC AGT AAA GAA GTT TAT ATC GTG TAC ATG GGA GCT GCA GAT TCA ACA AAA GCT   174
 T   N   S   K   E   V   Y   I   V   Y   M   G   A   A   D   S   T   K   A    54

TCT CTT AAA AAT GAG CAC GCT CAG ATT CTG AAT TCA GTG CTA AGA AGG AAT GAG AAT   231
 S   L   K   N   E   H   A   Q   I   L   N   S   V   L   R   R   N   E   N    73

GCC CTA GTA CGG AAC TAC AAG CAT GGT TTC TCT GGG TTC GCA GCT CGT CTA TCA AAA   288
 A   L   V   R   N   Y   K   H   G   F   S   G   F   A   A   R   L   S   K    92

GAG GAG GCA AAC TCA ATT GCT CAG AAA CCT GGT GTG GTG TCT GTT TTC CCT GAC CCC   345
 E   E   A   N   S   I   A   Q   K   P   G   V   V   S   V   F   P   D   P    111

ATT CTG AAG CTC CAC ACT ACA CGT TCA TGG GAT TTC CTC AAA AGC CAA ACT CGT GTC   402
 I   L   K   L   H   T   T   R   S   W   D   F   L   K   S   Q   T   R   V    130

AAT ATC GAC ACC AAA CCA AAT ACG CTG TCC GGT TCT TCT TTT TCT TCA TCA GAC GTC   459
 N   I   D   T   K   P   N   T   L   S   G   S   S   F   S   S   S   D   V    149

ATT CTT GGC GTC TTA GAC ACA GGC ATA TGG CCA GAG GCG GCG AGT TTT AGC GAC AAG   516
 I   L   G   V   L   D   T   G   I   W   P   E   A   A   S   F   S   D   K    168

GGT TTC GGT CCT GTT CCA TCC CGA TGG AAA GGC ACC TGC ATG ACA TCA AAA GAC TTC   573
 G   F   G   P   V   P   S   R   W   K   G   T   C   M   T   S   K   D   F    187

AAT TCC TCT TGT TGT AAC AGG AAG ATA ATT GGC GCG AGG TTT TAC CCT AAC CCA GAG   630
 N   S   S   C   C   N   R   K   I   I   G   A   R   F   Y   P   N   P   E    206

GAG AAA ACG GCA AGG GAT TTC AAC GGA CAT GGG ACT CAC GTT TCG TCG ACG GCA GTG   687
 E   K   T   A   R   D   F   N   G   H   G   T   H   V   S   S   T   A   V    225

GGC GTG CCG GTG AGT GGC GCA TCG TTC TAT GGT CTG GCG GCG GGG ACG GCA AGG GGT   744
 G   V   P   V   S   G   A   S   F   Y   G   L   A   A   G   T   A   R   G    244

GGG TCC CCT GAG TCA AGG TTG GCG GTT TAC AAA GTG TGT GGG GCT TTT GGG TCA TGT   801
 G   S   P   E   S   R   L   A   V   Y   K   V   C   G   A   F   G   S   C    263

CCT GGG TCG GCC ATT CTT GCG GGG TTT GAC GAT GCC ATT CAC GAC GGA GTG GAT ATC   858
 P   G   S   A   I   L   A   G   F   D   D   A   I   H   D   G   V   D   I    282

TTG TCG CTG TCG CTC GGT GGA TTC GGT GGA ACC AAA ACC GAT TTG ACC ACC GAC CCG   915
 L   S   L   S   L   G   G   F   G   G   T   K   T   D   L   T   T   D   P    301

ATT GCG ATT GGA GCA TTC CAC TCC GTC CAG CGC GGC ATC CTG GTG GTC TGC GCC GCC   972
 I   A   I   G   A   F   H   S   V   Q   R   G   I   L   V   V   C   A   A    320

GGG AAC GAC GGA GAA CCA TTC ACC GTT CTC AAC GAC GCA CCT TGG ATT TTA ACC GTT   1029
 G   N   D   G   E   P   F   T   V   L   N   D   A   P   W   I   L   T   V    339

GCA GCT TCC ACC ATC GAC CGT GAT CTT CAA TCC GAC GTG GTC TTG GGT AAT AAC CAA   1086
 A   A   S   T   I   D   R   D   L   Q   S   D   V   V   L   G   N   N   Q    358
```

FIG. 23(B)

```
GTC GTC AAG GGA AGA GCC ATA AAT TTC TCC CCT CTT TTA AAT TCT CCC GAT TAT CCA 1143
 V   V   K   G   R   A   I   N   F   S   P   L   L   N   S   P   D   Y   P  377

ATG ATA TAT GCT GAG TCT GCT GCC AGG GCA AAT ATC TCC AAC ATA ACT GAT GCA AGA 1200
 M   I   Y   A   E   S   A   A   R   A   N   I   S   N   I   T   D   A   R  396

CAA TGC CAC CCA GAT TCA TTA GAT CCA AAA AAA GTC ATA GGG AAG ATT GTG GTT TGT 1257
 Q   C   H   P   D   S   L   D   P   K   K   V   I   G   K   I   V   V   C  415

GAT GGA AAA AAT GAC ATT TAT TAT TCA ACT GAT GAG AAA ATT GTC ATA GTG AAG GCG 1314
 D   G   K   N   D   I   Y   Y   S   T   D   E   K   I   V   I   V   K   A  434

TTG GGA GGA ATA GGT CTG GTT CAT ATT ACT GAT CAA TCT GGA TCA GTA GCA TTT TAT 1371
 L   G   G   I   G   L   V   H   I   T   D   Q   S   G   S   V   A   F   Y  453

TAT GTG GAC TTC CCA GTA ACA GAG GTA AAA TCA AAA CAT GGC GAC GCA ATC CTC CAG 1428
 Y   V   D   F   P   V   T   E   V   K   S   K   H   G   D   A   I   L   Q  472

TAC ATC AAC TCA ACT AGC CAT CCA GTG GGA ACA ATA CTA GCA ACA GTT ACA ATT CCT 1485
 Y   I   N   S   T   S   H   P   V   G   T   I   L   A   T   V   T   I   P  491

GAT TAT AAG CCT GCT CCC CGG GTG GGT TAT TTT TCA TCA AGA GGG CCT TCA TTG ATT 1542
 D   Y   K   P   A   P   R   V   G   Y   F   S   S   R   G   P   S   L   I  510

ACA AGC AAT GTT CTC AAG CCT GAT ATT GCA GCC CCG GGA GTT AAC ATT CTC GCT GCA 1599
 T   S   N   V   L   K   P   D   I   A   A   P   G   V   N   I   L   A   A  529

TGG TTT GGA AAT GAC ACA TCA GAG GTT CCA AAA GGA AGA AAG CCC TCA CTA TAT CGC 1656
 W   F   G   N   D   T   S   E   V   P   K   G   R   K   P   S   L   Y   R  548

ATA CTC TCA GGA ACT TCC ATG GCT ACT CCA CAT GTT TCA GGG CTT GCA TGC AGT GTC 1713
 I   L   S   G   T   S   M   A   T   P   H   V   S   G   L   A   C   S   V  567

AAA AGA AAA AAC CCC ACT TGG AGT GCC TCC GCA ATC AAA TCT GCC ATC ATG ACT TCA 1770
 K   R   K   N   P   T   W   S   A   S   A   I   K   S   A   I   M   T   S  586

GCA ATT CAA AAT GAC AAT TTG AAG GGT CCC ATA ACA ACG GAT TCA GGG TTG ATA GCC 1827
 A   I   Q   N   D   N   L   K   G   P   I   T   T   D   S   G   L   I   A  605

ACA CCT TAT GAC TAT GGA GCA GGG GCA ATT ACA ACA TCT GAA CCA TTG CAA CCG GGG 1884
 T   P   Y   D   Y   G   A   G   A   I   T   T   S   E   P   L   Q   P   G  624

CTA GTT TAT GAA ACC AAC AAC GTT GAC TAC TTG AAC TAT TTG TGT TAC AAT GGA CTT 1941
 L   V   Y   E   T   N   N   V   D   Y   L   N   Y   L   C   Y   N   G   L  643

AAC ATA ACC ATG ATA AAG GTC ATC TCC GGA ACT GTC CCC GAG AAT TTC AAT TGT CCC 1998
 N   I   T   M   I   K   V   I   S   G   T   V   P   E   N   F   N   C   P  662

AAG GAT TCG AGC TCT GAT CTC ATC TCC AGC ATC AAC TAC CCT TCC ATA GCA GTA AAC 2055
 K   D   S   S   S   D   L   I   S   S   I   N   Y   P   S   I   A   V   N  681

TTC ACT GGC AAA GCA GAC GCG GTC GTG AGT AGA ACT GTC ACA AAC GTT GAC GAA GAA 2112
 F   T   G   K   A   D   A   V   V   S   R   T   V   T   N   V   D   E   E  700

GAT GAA ACA GTG TAC TTC CCC GTT GTT GAA GCT CCT AGT GAA GTA ATT GTC ACA CTC 2169
 D   E   T   V   Y   F   P   V   V   E   A   P   S   E   V   I   V   T   L  719

TTT CCA TAT AAT CTT GAG TTT ACG ACA AGT ATT AAA AAA CAA AGC TAC AAT ATT ACT 2226
 F   P   Y   N   L   E   F   T   T   S   I   K   K   Q   S   Y   N   I   T  738
```

FIG. 23(B)(Cont'd)

```
TTC AGA CCG AAG ACC TCC TTG AAG AAA GAT TTG TTT GGA TCT ATC ACT TGG AGT AAC  2283
 F   R   P   K   T   S   L   K   K   D   L   F   G   S   I   T   W   S   N   757

GAC AAA TAT ATG GTT CGA ATT CCT TTT GTA TTA ACT AAA TAG tgaaattaaaaagtagcga  2344
 D   K   Y   M   V   R   I   P   F   V   L   T   K   *                       770 tgaataaatgcaagctaagttcttcgtggtgcctacactcgagtcctgattatttattattcatatgccttctgt  2419 tttaatttat ttattatact ttcagcct(a)n                                          2447
```

FIG. 23(B)(Cont'd)

| D region | | H region | |
|---|---|---|---|
| | * | | * |
| SC20:2 | SDVILGVLDTGI 156 | SC20:2 | DFNGHGTHVSSTAVG 224 |
| AF70 | TDIILGFLDTGI 145 | AF70 | DYQGHGTYTAATAAG 229 |
| Cucumisin | SNIVVGVLDTGI 143 | Cucumisin | DNTGHGTHTASTAAG 214 |
| P69B | KGVIIGVIDTGI 149 | P69B | DDIGHGTHTASTAAG 213 |
| Ag12 | EDVIIGVIDSGV 148 | Ag12 | DTLGHGTHTASTAAG 216 |
| Subtilisin BPN′ | SNVKVAVIDSGI 142 | Subtilisin BPN′ | DNNSHGTHVAGTVAA 181 |
| Kex2 | AGVVAAIVDDGL 178 | Kex2 | SDDYHGTRCAGEIAA 223 |
| Furin | HGIVVSILDDGI 156 | Furin | NDNRHGTRCAGEVAA 204 |

| S region | | N region | |
|---|---|---|---|
| | * | | # |
| SC20:2 | SGTSMATPHVSGLA 562 | SC20:2 | SVQRGILVVCAAGNDG 322 |
| AF70 | SGTSVAVPHVTGAA 571 | AF70 | ATQKGILVVSSAGNEG 329 |
| Cucumisin | SGTSMSCPHITGIA 535 | Cucumisin | AVERGILTSNSAGNGG 310 |
| P69B | SGTSMSCPHLSGVA 541 | P69B | ATERGILVSCSAGNSG 308 |
| Ag12 | SGTSMACPHASGVA 547 | Ag12 | AMEKGVVVSTSAGNAG 318 |
| Subtilisin BPN′ | NGTSMASPHVAGAA 338 | Subtilisin BPN′ | AVASGVVVVAAAGNEG 264 |
| Kex2 | GGTSAAAPLAAGVY 395 | Kex2 | RDSKGAIYVFASGNGG 316 |
| Furin | TGTSASAPLAAGII 378 | Furin | RGGLGSIFVWASGNGG 297 |

FIG. 23(D)

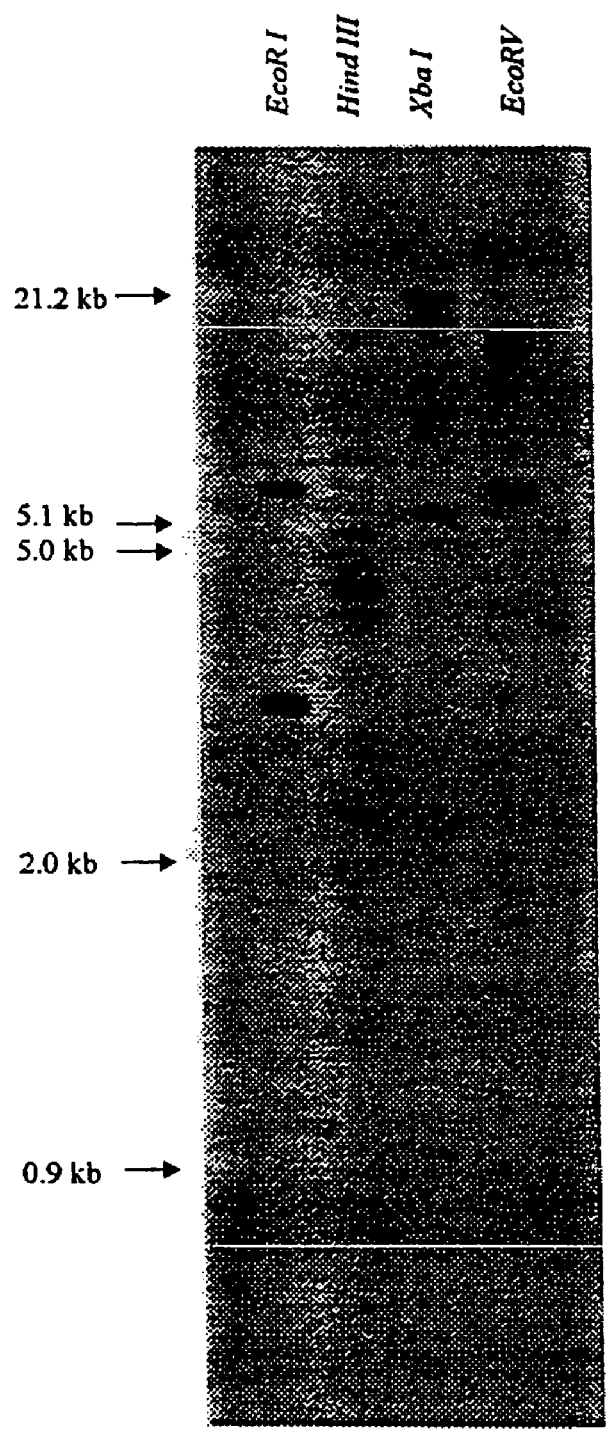
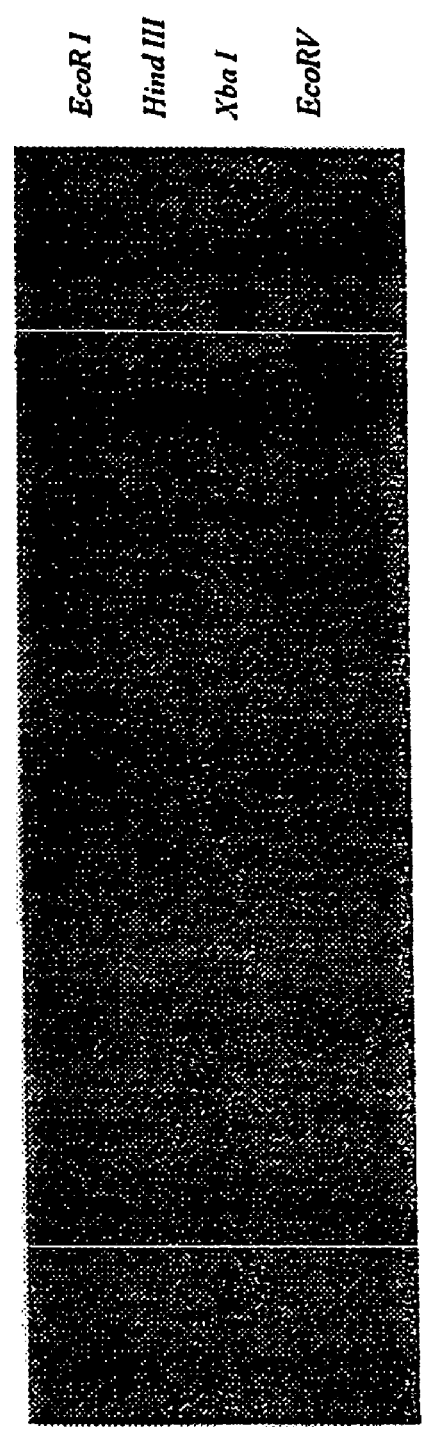
Fig. 25 A    Fig. 25 B

SEED COAT GENE AND GENE PRODUCT

FIELD OF INVENTION

This invention relates to seed-coat promoters, genes and proteins encoded by these genes. More specifically, it relates to genes and promoters that are developmentally regulated and expressed, or activated, within tissues comprising the seed-coat, and tissues directly associated with the seed-coat, of plants. Furthermore, this invention also relates to proteins encoded by genes expressed within these tissues are their localization within, or onto, the seed-coat.

BACKGROUND AND PRIOR ART

Bacteria from the genus *Agrobacterium* have the ability to transfer specific segments of DNA (T-DNA) to plant cells, where they stably integrate into the nuclear chromosomes. Analyses of plants harbouring the T-DNA have revealed that this genetic element may be integrated at numerous locations, and can occasionally be found within genes. One strategy which may be exploited to identify integration events within genes is to transform plant cells with specially designed T-DNA vectors which contain a reporter gene, devoid of cis-acting transcriptional and translational expression signals (i.e. promoterless), located at the end of the T-DNA. Upon integration, the initiation codon of the promoterless gene (reporter gene) will be juxtaposed to plant sequences. The consequence of T-DNA insertion adjacent to, and downstream of, gene promoter elements may be the activation of reporter gene expression. The resulting hybrid genes, referred to as T-DNA-mediated gene fusions, consist of unknown and thus uncharacterized plant promoters residing at their natural location within the chromosome, and the coding sequence of a marker gene located on the inserted T-DNA (Fobert et al., 1991, Plant Mol. Biol. 17, 837-851).

It has generally been assumed that activation of promoterless or enhancerless marker genes result from T-DNA insertions within or immediately adjacent to genes. The recent isolation of several T-DNA insertional mutants (Koncz et al., 1992, Plant Mol. Biol. 20, 963-976; reviewed in Feldmann, 1991, Plant J. 1, 71-82; Van Lijsebettens et al., 1991, Plant Sci. 80, 27-37; Walden et al., 1991, Plant J. 1: 281-288; Yanofsky et al., 1990, Nature 346, 35-39), shows that this is the case for at least some insertions. However, other possibilities exist. One of these is that integration of the T-DNA activates silent regulatory sequences that are not associated with genes. Lindsey et al. (1993, Transgenic Res. 2, 3347) referred to such sequences as "pseudo-promoters" and suggested that they may be responsible for activating marker genes in some transgenic lines.

Inactive regulatory sequences that are buried in the genome but with the capability of being functional when positioned adjacent to genes have been described in a variety of organisms, where they have been called "cryptic promoters" (Al-Shawi et al., 1991, Mol. Cell. Biol. 11, 4207-4216; Fourel et al., 1992, Mol. Cell. Biol. 12, 5336-5344; Irniger et al., 1992, Nucleic Acids Res. 20, 4733-4739; Takahashi et al., 1991, Jpn J. Cancer Res. 82, 1239-1244). Cryptic promoters can be found in the introns of genes, such as those encoding for yeast actin (Irniger et al., 1992, Nucleic Acids Res. 20, 4733-4739), and a mammalian melanoma-associated antigen (Takahashi et al., 1991, Jpn J. Cancer Res. 82, 1239-1244). It has been suggested that the cryptic promoter of the yeast actin gene may be a relict of a promoter that was at one time active but lost function once the coding region was assimilated into the exon-intron structure of the present-day gene (Irniger et al., 1992, Nucleic Acids Res. 20, 4733-4739). A cryptic promoter has also been found in an untranslated region of the second exon of the woodchuck N-myc proto-oncogene (Fourel et al., 1992, Mol. Cell. Biol. 12, 5336-5344). This cryptic promoter is responsible for activation of a N-myc2, a functional processed gene which arose from retroposition of N-myc transcript (Fourel et al., 1992, Mol. Cell. Biol. 12, 5336-5344). These types of regulatory sequences have not yet been isolated from plants.

Weber et al. (1995, Plant Cell 7:1835-1846) disclose a cDNA sequence of a seed-coat associated invertase. However, all of the cDNA's characterized were found to be expressed in tissues other than the seed-coat, including anthers, cotyledon, stem and root. Furthermore, no promoter was isolated, characterized, or disclosed.

Described herein is the occurrence of seed-coat genes and promoters that have been obtained as a result of differential screening of seed-coat genomic libraries, or generated by tagging with a promoterless GUS (β-glucuronidase) T-DNA vector, or by identification of genes that are highly expressed in the seed-coat or associated tissues. Expression analysis of these DNA's reveal that they are spatially and developmentally regulated in seed coats. Prior to this work, promoters, as well as genes specifically expressed in seed coat tissues had not been isolated or reported. Furthermore, proteins encoded by genes that are expressed within seed-coat, or associated with seed-coat tissues, are also disclosed.

SUMMARY OF INVENTION

This invention relates to seed-coat promoters and genes. More specifically, it relates to genes and promoters that are developmentally regulated and expressed, or activated, within tissues comprising the seed-coat of plants, and tissues directly associated with the seed-coat, of plants. Furthermore, this invention also relates to proteins encoded by genes expressed within these tissues and their localization within, or onto, the seed-coat.

A transgenic tobacco plant, T218, contained a 4.7 kb EcoRI fragment containing the 2.2 kb promoterless GUS-nos gene and 2.5 kb of 5' flanking tobacco DNA. Deletion of the region approximately between 2.5 and 1.0 kb of the 5' flanking region did not alter GUS expression, as compared to the entire 4.7 kb GUS fusion. A further deletion to 0.5 kb of the 5' flanking site resulted in complete loss of GUS activity. Thus the region between 1.0 and 0.5 of the 5' flanking region of the tobacco DNA contains the elements essential to gene activation. This region is contained within a XbaI-SnaBI restriction site fragment of the flanking tobacco DNA. Furthermore, other promoters have been identified that are differentially expressed within the seed-coats of plants, and that are capable of driving expression of heterologous genes that are operatively linked thereto.

Thus according to the present invention there is provided an isolated genomic DNA molecule, differentially expressed in seed coat tissues. Furthermore, this genomic DNA molecule is differentially expressed within the outer integument of the seed coat, the inner integument of the seed coat, the thick walled parenchyma of the seed coat, the thin walled parenchyma of the seed coat, the endothelium of the seed coat, the hourglass cells of the seed coat, the palisade of the seed coat, the stellate parenchyma of the seed coat, or the membranous endocarp, or a combination thereof.

This invention is also directed to a seed-coat promoter obtained from the genomic DNA molecule as described above. Also considered within the scope of the present invention is a cryptic seed coat promoter. Furthermore, this invention is directed to a seed coat promoter, as described above, that controls the differential expression of a gene associated therewith, within the outer integument of the seed coat, the inner integument of the seed coat, the thick walled parenchyma of the seed coat, the thin walled parenchyma of the seed coat, the endothelium of the seed coat, the hourglass cells of the seed coat, the palisade of the seed coat, or the stellate parenchyma the seed coat, membranous endocarp, or a combination thereof This invention also relates to an isolated genomic DNA characterized by the restriction map selected from the group consisting of FIG. 12(a), FIG. 12(b), FIG. 12(c) and FIG. 12(d).

According to the present invention, there is also provided an isolated seed-coat promoter. Furthermore, this seed coat promoter may be obtained from angiosperms. More specifically, this seed-coat promoter is obtained from the group consisting of tobacco or soybean.

This invention is also directed to a cloning vector comprising a gene encoding a protein and an isolated seed-coat promoter, wherein the gene is under the control of the seed-coat promoter. Furthermore, this invention includes a plant cell which has been transformed with such a vector.

This invention also provides for a transgenic plant containing a seed-coat promoter, operatively linked to a gene encoding a protein.

The present invention is also directed to a seed-coat promoter comprising at least 10 contiguous nucleotides of nucleotides 1-2526 of SEQ ID NO:7, or an analogue of the sequence defined by nucleotides 1-2526 of SEQ ID NO:7, wherein the analogue hybridizes to a nucleic acid defined by nucleotides 1-2526 of SEQ ID NO:7 under stringent hybridization conditions and maintains seed-coat, or seed-coat associated promoter activity.

This invention also includes a seed-coat promoter comprising at least 10 contiguous nucleotides of nucleotides 1-2450 of SEQ ID NO:8, or an analogue of the nucleic acid sequence defined by nucleotides 1-2450 of SEQ ID NO:8, wherein the analogue hybridizes to a nucleic acid defined by nucleotides 1-2450 of SEQ ID NO:8 under stringent hybridization conditions and maintains seed-coat, or seed-coat associated promoter activity.

The present invention also is directed to a seed-coat promoter comprising at least 10 contiguous nucleotides of nucleotides 1-5514 of SEQ ID NO:9, or an analogue of the nucleotides sequence defined by nucleotides 1-5514 of SEQ ID NO:9, wherein the analogue hybridizes to a nucleic acid defined by nucleotides 1-5514 of SEQ ID NO:9 under stringent hybridization conditions and maintains seed-coat, or seed-coat associated promoter activity.

BRIEF DESCRIPTION OF THE DRAWINGS

FIG. 3 shows the expression pattern of promoter fusions during seed development. GUS activity in developing seeds (4-20 days postanthesis (dpa)) of (FIG. 3a) plant T218 (●-●) and.

FIG. 5 shows the mapping of the T218 GUS fusion termini and expression of the region surrounding the insertion site in untransformed plants.

FIG. 6 provides the nucleotide sequence of pT218 (top line) (SEQ ID NO: 1) and pIS-1 (bottom line). Sequence identity is indicated by dashed lines. The T-DNA insertion site is indicated by a vertical line after bp 993. This site on pT218 is immediately followed by a 12 bp filler DNA, which is followed by the T-DNA. The first nine amino acids of the GUS gene and the GUS initiation codon (*) are shown. The major and minor transcriptional start site is indicated by a large and small arrow, respectively. The presumptive TATA box is identified and is in boldface. Additional putative TATA and CAAT boxes are marked with boxes. The location of direct (1-5) and indirect (6-8) repeats are indicated by arrows.

FIG. 10(*a*) shows the expression of SC4; FIG. 10(*b*) shows the expression of SC20; FIG. 10(*c*) shows the expression of SC21, FIG. 10(*d*) shows the expression of Ep locus peroxidase within these tissues. FIG. 10(*e*) shows the expression of HP (hydrophobic protein) in leaf, flower, pod, seed coat, embryo, stem or root tissues. FIGS. 10(*f*) and (*g*), total RNA was isolated from leaf, flower, pod shells, seed coat, embryo, stem or root tissue. Equal amounts of RNA (10 µg) were vacuum blotted to nylon and probed with HPS cDNA. Ribosomal RNA (rRNA), visualized by staining with ethidium bromide, is shown as control. FIG. 10(*f*), RNA from tissues at early (E) mid (M) or late (L) stages of development were compared for HP gene expression. All samples shown are from dull seeded phenotype (cv Harosoy 63). FIG. 10(*g*), RNA from pod tissues of dull (cv Harosoy 63) and shiny (cv. Williams 82) seeded soybeans were compared for HP gene expression.

FIG. 11(*b*) SC21; FIG. 11(*c*) HP (hydrophobic protein) genomic region, and FIG. 11(*d*) SC4. Included in FIG. 11(*c*) are restriction enzyme sites for BamHI, BglII, HindIII, and XbaI; the HP ORF; TATA box consensus signals; and the position of direct repeats of 12 bp or longer.

FIG. 12(*a*) shows the structures present at six days after anthesis (DAF); FIG. 12(*b*), at 12 DAF; and FIG. 12(*c*) at 18 DAF.

FIG. 13(*a*) seed coat at 3 days after anthesis (DAF), probed with SC4; FIG. 13(*b*) seed coat at 9 DAF, probed with SC20; FIG. 13(*c*) seed coat at 15 DAF, probed with SC21; FIG. 13(*d*) seed coat at 18 days after anthesis, probed with a soybean peroxidase, corresponding to the Ep locus. FIGS. 13(*e*), (*f*) and (*g*) were obtained from cross sections of developing soybean seeds (cultivar Maple Presto, EpEp). Hybridization of $^{35}$S-probe to complementary mRNA appears as bright white signal in these dark field microscopy images. FIG. 13(*e*) 6 DAF (DPA, days post anthesis), FIG. 13(*f*) 9 DAF, and FIG. 13(*g*) 12 DAF. Scale bars are 100 :m. Emb, embryo; F, funiculus; HG, hourglass cells; PC, pericarp; SC, seed coat.

FIG. 14(*a*) shows a plastic embedded section of the seed-coat near the hilum at 21 daf and stained with Toluidine Blue O. Note the association of the membranous endocarp with the seed-coat pallisade. FIG. 14(*b*) shows a wax-embedded section of a soybean seed-coat as 12 daf probed with $^{35}$S-labelled Hydrophobic Protein (HP) antisense RNA, and counter stained with Toluidine Blue O. Note strong specific localization of the probe within the membranous endocarp. Pallisade (p), hourglass cells (h), counterpallisade (c), arial cells (a), stellate parenchyma (s), thin walled parenchyma (n), thickwalled parenchyma (k), pod parenchyma (d), and membranous endocarp ➤. FIGS. 14(*c*) and (*d*) show localization of HP mRNA transcript by in situ hybridization. Cross sections of soybean pods containing immature seeds (dull phenotype, HPS (+), cv Maple Presto). Hybridization of $^{35}$S labelled HP probe to complementary mRNA appears as bright white signal in these dark field microscopy images. E, embryo; Ep, inner epidermal layer of endocarp; Ex, exocarp; F, funiculus; M, mesocarp; Sc, seed coat; Sm, sclerenchyma layer of endocarp. Bar=100 µm. FIG. 14(*c*), Expression at 6 DPA (days post anthesis). FIG. 14(*d*), Expression 12 DPA.

FIG. 15 shows the Soybean hydrophobic protein (HP) cDNA and deduced amino acid sequences. FIG. 15(*a*), the cDNA and amino acid sequence of HP. The pre-protein signal sequence is underlined. FIG. 15(*b*) shows the deduced amino acid sequence of HP pre-protein. Alternate N-terminal residues are boxed, as determined by peptide microsequence analysis. FIG. 15(*c*) shows a Kyle-Doolittle hydrophilicity plot of HP (Lasergene). In this plot, positive values indicate greater hydrophilic character. Also represented are the three domains of the HP pre-protein and the length of the mature peptide. FIG. 15(*d*) shows a schematic comparison of HP domain structure to three other plant proteins. Bold numbers indicate the length in amino acid residues for the domain segments. The pattern of spacing between the eight cysteine residues within the hydrophobic domains is also shown below each protein. Sequences for tobacco N16 polypeptide (D86629), maize proline rich hydrophobic protein (PRHP) (X60432), and *Arabidopsis* lipid transfer protein 1 (LTP1) (M80567) were retrieved from GenBank.

FIG. 16 shows scanning electron micrographs of representative 'Dull' and 'Shiny' seeded soybean cultivars. Scale bars are included in the figures. The lowest magnification (×18), FIG. 16(*a*) is a view of the entire seed. The large oval shaped scar on the seed surface is the hilum, corresponding to the point of detachment of the mature seed from the funiculus. FIG. 16(*b*), ×100, and FIG. 16(*c*) ×500, are focused outside of hilum region.

FIG. 17(*a*), Soluble protein extracts from the embryo, seed coat, and seed surface of a dull phenotype (cv Harosoy 63). Each sample at approximately 1 µg of total protein. FIG. 17(*b*), Seed surface protein extracts of a dull phenotype (cv Harosoy 63) with different concentrations of dithiothreitol (DTT) present in the sample loading buffer, as indicated at the top of each lane. FIG. 17(*c*), Seed surface protein extracts of dull (D), shiny (S), and bloom (B).

FIG. 19 shows the nucleotide sequence and deduced amino acid sequence of SC4 cDNA, and the sequence comparisons between SC4 protein and BURP proteins. FIG. 19(*a*), 5' and 3' untranslated sequences are in lowercase lettering. The stop codon is shown with an asterisk and two polyadenylation signals are underlined. Two copies of a ten amino acid repeat is also underlined. Concensus sequences for N-glycosylation (NNT; NSSN; and NGTV) are also underlined. FIG. 19(b), amino acid alignment of the carboxyl terminus of the SC4 protein with the BURP domain (A) and the amino terminus of the SC4 protein with the conserved segments of the second domain (B) of several BURP domain proteins. Pg1β is not included in panel B as the second domain of this protein does not contain a conserved segment. Gaps were introduced to optimize the alignment. Conserved amino acids are shown in bold face. Amino acids of each protease are numbered from the precursor sequence.

FIG. 22(a) shows Southern analysis of the gene family composition of sc4 in soybean. FIG. 22(b) shows Southern analysis of sc4 in diverse plant species. Hybridized filter was washed under conditions of low stringency, twice at 52° C. for 15 min in 2×SSC, 0.1% SSC, 0.1% SDS and once at 52° C. for 30 min in 0.1×SSC, 0.1% SDS.

FIG. 23 reveals the characterization of sc20 and the SC20 protein. FIG. 23(b) shows the nucleotide sequence and deduced amino acid sequence of sc20 cDNA SEQ ID NO:12. The stop codon is shown with an asterisk and the polyadenylation signal is underlined. The concensus sequences for N-glycosylation are also underlined. In FIG. 23(d), alignment of SC20 protein with other subtilases is shown. D, H and S regions represent amino acid sequences around the catalytic aspartate, histidine and serine residues of the subtilases. The catalytic residues are labelled with an asterisk. N region represents amino acid sequence around the conserved asparagine residue, of subtilases. # indicates the conserved asparagine. AF70, cucumisin, P69B, Ag12, subtilisin BPN', kex2, furin are from *Picea abies, Cucumis melo* L., *Lycopersicon esculentum, Alnus glutinosa, Bacillus subtilis, Saccharomyces cerevisiae*, and *Homo sapiens* respectively. Conserved amino acids are shown in boldface. Amino acids of each protease are numbered from the precursor sequence.

FIG. 25(a) and (b), Southern analysis of the gene family composition of sc20 in soybean under conditions of medium stringency (twice at 52° C. for 15 min in 2×SSC, 0.1% SDS, and once at 52° C. for 30 min in 0.1×SSC, 0.1% SDS), FIG. 25(a), and high stringency (once at 62° C. for 30 min in 0.1×SSC, 0.1% SDS) FIG. 25(b). FIG. 25(c) shows Southern analysis of sc4 in diverse plant species genomic DNA was digested with EcoRI. Hybridization used a radiolabelled SC20 cDNA probe. The filter was washed under conditions of medium stringency, twice at 52° C. for 15 min in 2×SSC, 0.1% SDS and once at 52° C. for 30 min in 0.1×SSC, 0.1% SDS.

DETAILED DESCRIPTION OF THE PREFERRED EMBODIMENTS

T-DNA tagging with a promoterless β-glucuronidase (GUS) gene generated a transgenic *Nicotiana tabacum* plant that expressed GUS activity only in developing seed coats. Cloning and deletion analysis of the GUS fusion revealed that the promoter responsible for seed coat specificity was located in the plant DNA proximal to the GUS gene. Deletion analyses localized the cryptic promoter to an approximately 0.5 kb region between a XbaI and a SnaBI restriction endonuclease site of the 5' flanking tobacco DNA. This region spans from nucleotide 1 to nucleotide 467 of SEQ ID NO: 1.

Figure 11C:
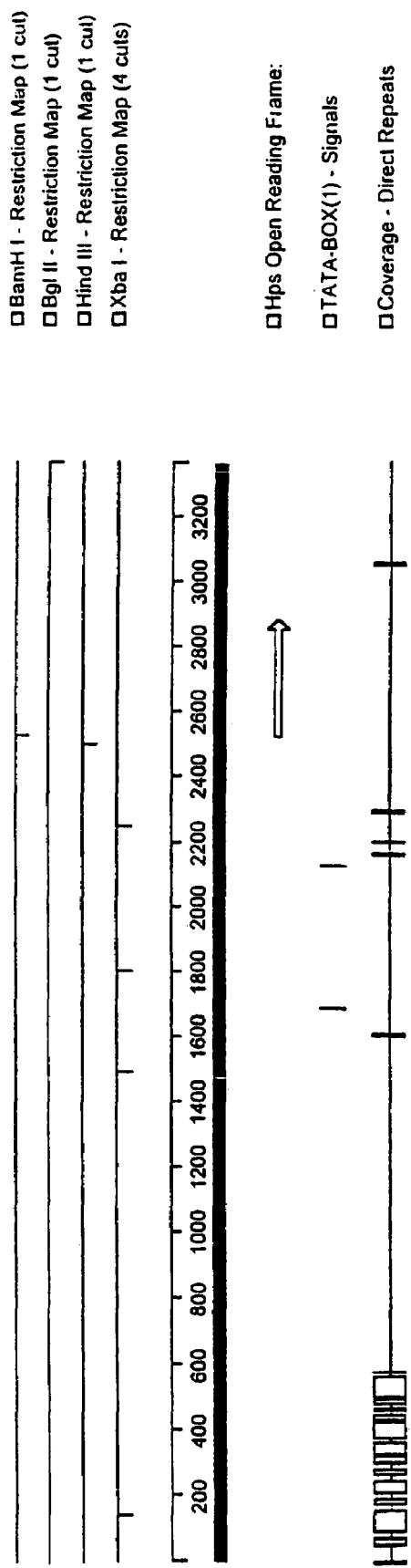
Figure 12A:
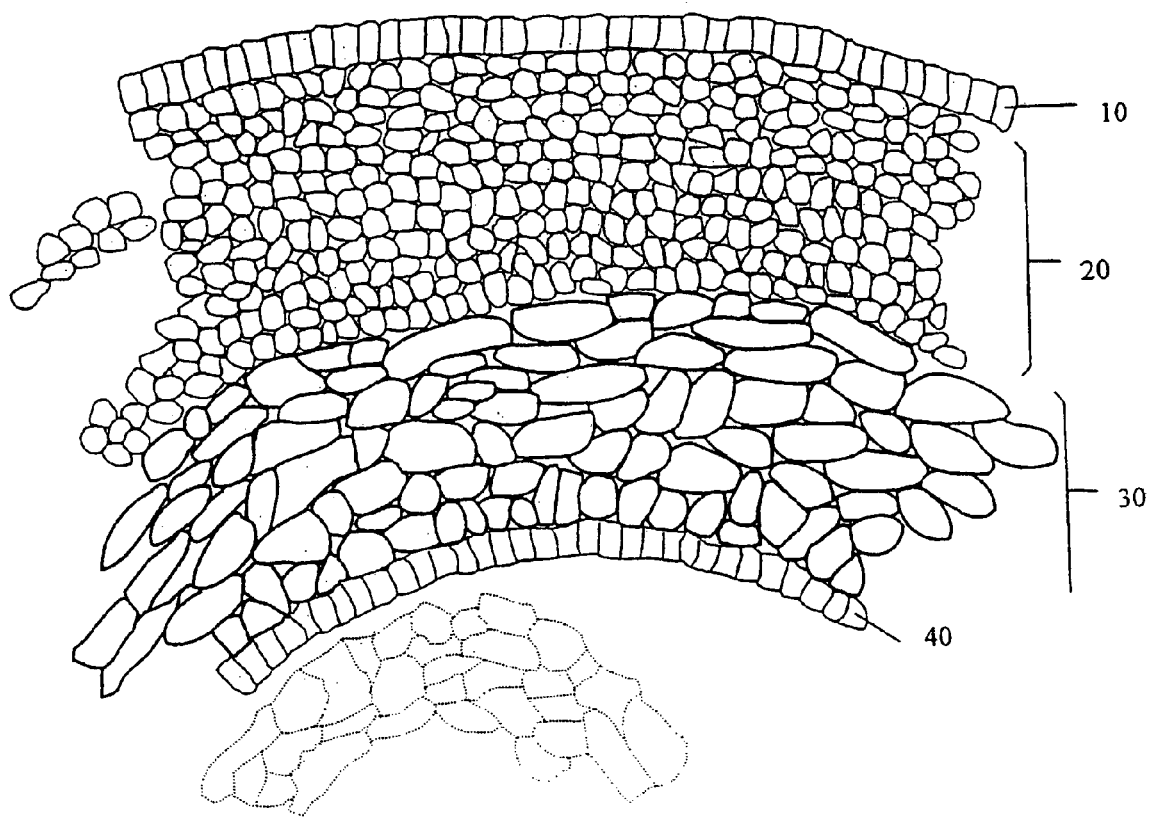
FIG. 12 shows the morphology of the seed coat of *Glycine max*.

Other work, based on the differential screening of seed coat libraries has led to the identification of several other genes that are differentially expressed within, or tissues that are directly associated with, the seed coat of plants. These genes include SC4 (SEQ ID NO's: 3 and 9, cDNA and genomic sequences, respectively), SC20 (SEQ ID NO's: 4 and 8, cDNA and genomic sequences respectively), SC21 (SEQ ID NO: 5, cDNA sequence), and their associated promoters (see SEQ ID NO 9 and 8 for promoters of SC 4 and SC20, respectively; also FIG. 12). Furthermore, the isolation of genes encoding highly expressed seed coat proteins led to the identification of a seed-coat specific peroxidase from the Ep locus and associated promoter (Ep genomic sequence, SEQ ID NO:2), as well as a gene encoding a seed-coat localized hydrophobic protein (HP, cDNA sequence SEQ ID NO:6) and associated promoter (within genomic sequence, SEQ ID NO:7, also see FIG. 11(c)). Thus, the present invention includes promoters, genes and proteins isolated from several plant species, that are preferentially expressed, or specific to seed-coat tissues, as well as promoters, genes and associated proteins obtained from tissues associated with the seed-coat.

The term cryptic promoter means a promoter that is not associated with a gene and thus does not control expression in its native location. These inactive regulatory sequences are buried in the genome but are capable of being functional when positioned adjacent to a gene.

The DNA sequence of an aspect of the present invention includes the DNA sequence of SEQ ID NO: 1, the promoter region within SEQ ID NO: 1 (for example from nucleotide 1 to 476), and analogues thereof. Similarly, another aspect of this invention includes a DNA sequence of. SEQ ID NO:2, the promoter region of this sequence (nucleotides 1-1532), and analogues thereof. Another aspect of this invention includes a DNA sequence of SEQ ID NO:7, the promoter region (nucleotides 1-2526), and analogues thereof, a DNA sequence of SEQ ID NO 8, the promoter region (nucleotides 1-2450) and analogues thereof, and a DNA sequence of SEQ ID NO:9, the promoter region (nucleotides 1-5514) and analogues thereof.

Analogues include those DNA sequences which hybridize under stringent hybridization conditions (see Maniatis et al., in Molecular Cloning (A Laboratory Manual), Cold Spring Harbor Laboratory, 1982, p. 387-389) to the DNA sequence of SEQ ID NO: 1, 2, 7, 8 or 9 provided that said sequences maintain the seed coat, or seed-coat associated promoter activity. An example of one such stringent hybridization conditions may be hybridization at 4×SSC at 65° C., followed by washing in 0.1×SSC at 65° C. for an hour, or at 62° C. for 30 min in 0.1×SSC, 0.1% SDS. Alternatively an exemplary stringent hybridization condition could be in 50% formamide, 4×SSC at 42° C. With the use of Digoxigenin labelled probes, stringent hybridization may include 65° C. in 0.25 M $Na_2HPO_4$ (pH 7.2), 20% SDS, 1 mM EDTA and 0.5% blocking reagent (Boehringer Mannheim) followed by washing at 22° C. in 20 mM $Na_2HPO_4$ (pH 7.2), 1% SDS and 1 mM EDTA and washes in the same solution at 68° C. Analogues also include those DNA sequences which hybridize to the sequence of SEQ ID NO: 1, 2, 7, 8 or 9 under relaxed hybridization conditions provided that said sequences maintain the seed-coat promoter activity. Examples of such non-hybridization conditions includes hybridization at 4×SSC at 50° C. or with 30-40% formamide at 42° C. Alternate conditions of medium stringency include washing the filter twice at 52° C. for 15 min in 2×SSC, 0.1% SDS and once at 52° C. for 30 min in 0.1×SSC, 0.1% SDS.

Furthermore, another aspect of this invention is directed to the identification and characterization of seed-coat promoters (see FIG. 11) and their corresponding genes of cDNA's (SEQ ID NO's: 3-6), as characterized by Southern or in situ hybridization analysis of the expression patterns of genes expressed under the control of seed-coat promoters within developing seed coats (FIGS. 13 and 14). Furthermore, restriction maps of the promoter and downstream regions of several seed-coat genomic clones is presented (FIG. 11).

Figure 12B:
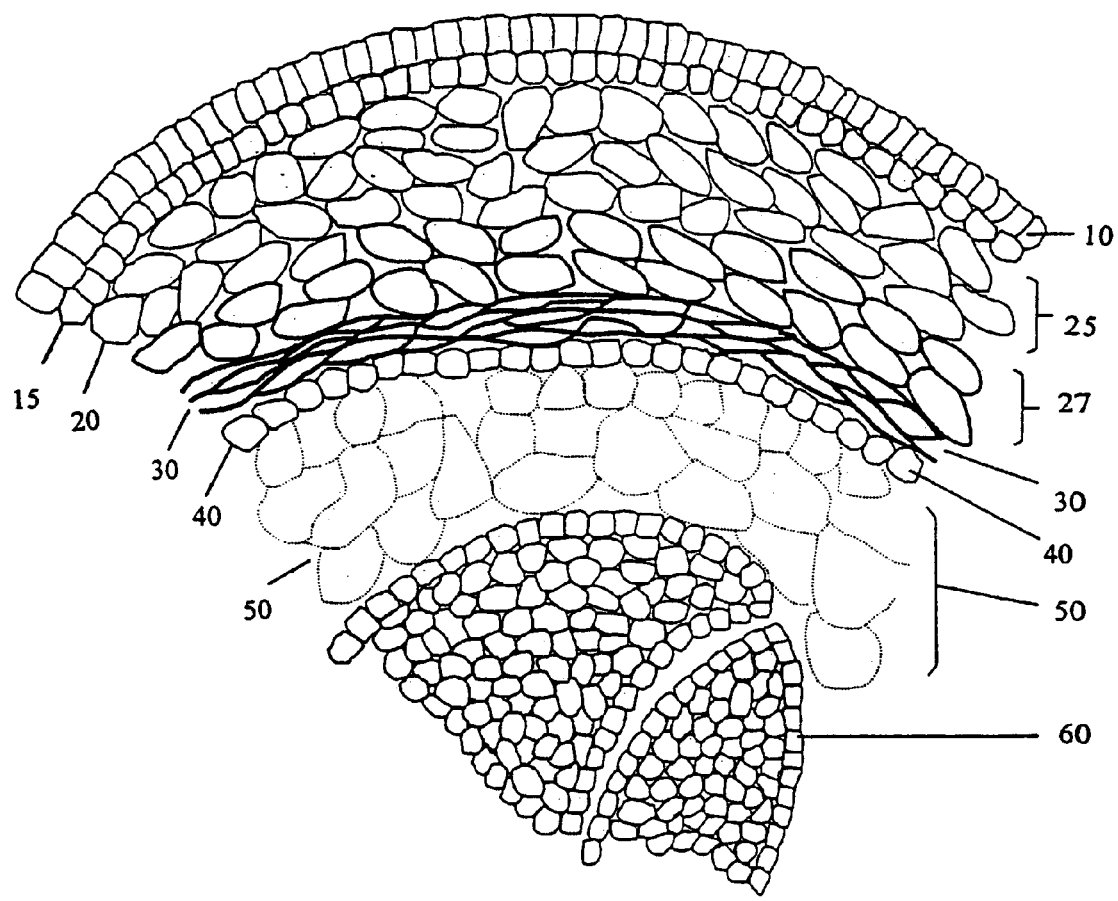

Proteins of interest may be expressed in seed coat tissues by placing a gene capable of expressing the protein of interest under the control of the DNA promoters of this invention. Genes of interest include but are not restricted to herbicide resistant genes, genes encoding viral coat proteins, or genes encoding proteins conferring biological control of pest or pathogens such as an insecticidal protein for example *B. thuringiensis* toxin. Other genes include those capable of modifying the production of proteins that alter the taste of the seed and/or that affect the nutritive value of the seed.

By "seed-coat" it is meant tissues typically found within, and associated with, the seed-coat of developing or mature angiosperm seeds. With out wishing to limit the types of tissues found within a seed-coat, this region of the seed typically comprises a range of cell types including, and bounded by, an inner endothelium, and an outer epidermis or palisade cell layer. Within these inner and out cell layers, there may be found parenchyma-like cells, for example thin, or thick walled parenchyma, or stellate parenchyma, vascular tissue, hypodermis, hour-glass cells (osteosclereids), and one or more integuments, including the inner and outer integuments. However, it is to be understood that other cell types found within the region between the inner endothelium and outer epidermis may also be considered to comprise the seed-coat, for example, but not limited to the hilum, and funiculus comprising arial cells. Furthermore, it is to be understood that "seed-coat" also refers to tissues associated with, or adhering to the seed coat, for example the membranous endocarp (of the inner ovary wall), as this cell type adheres to the seed-coat and remains in association with the seed coat (see for example FIGS. 15(*a*), (*b*), and FIG. 16). Therefore, as used herein, tissues that are associated with, or that adhere to, the seed-coat are referred to as "seed-coat associated tissues", or "tissues associated with the seed-coat" It is contemplated that other cell types may also associate with seed-coat tissues in addition to those disclosed above and that the tissues identified above should not be considered limiting in any manner.

By "seed-coat gene" it is meant a gene that is differentially expressed within the seed-coat as detected under stringent conditions (as defined above). Examples of such a gene include, but are not limited to SC4, SC 20, SC 21, or Ep locus peroxidase. However, the product of the gene may be exported from the cell to an exterior location of a seed-coat cell, including the surface of the seed-coat itself. An example, which is not to be considered limiting in any manner, of a gene product that is synthesized in within a seed-coat associated cell, and that is localized onto the surface of the seed coat, is the hydrophobic protein (HP; see FIGS. 14(*a*) (*b*) and FIG. 16).

A "seed-coat promoter" is a promoter that is differentially active within cells of the seed-coat. When operably linked with a gene under its control, a seed-coat promoter confers expression to a gene within the seed-coat, which can be detected under stringent conditions (as defined above). Seed coat associated promoter refers to a promoter that is active in tissue associated with the seed coat as defined above.

By "differentially expressed" it is meant the expression of a gene under the control of a promoter, as detected by standard means, within a specified tissue or organ. Such standard means for detecting expression include, but are not limited to, Northerns, or in situ hybridizations and the like performed under stringent conditions, or reporter gene expression. For example, a gene that is differentially expressed in seed-coat tissues is detectable within seed-coat tissues, and displays little or no expression in other tissues such as root, stem.

By "preferentially expressed" it is meant the expression of a gene under the control of a promoter, as detected by standard means, wherein the majority of expression is detected within a specified tissue or organ. Such standard means for detecting expression include, but are not limited to, Northerns, or in situ hybridizations and the like performed under stringent conditions, or the expression of reporter genes. For example, a gene that is preferentially expressed in seed-coat tissues is detectable within seed-coat tissues, but may exhibit some expression within other tissues such as root, stem.

By "seed-coat localized" or "localized onto the seed-coat" it is meant a gene product that, as a result of some property of the amino acid sequence of the gene product, is targeted within, or onto seed-coat tissues, respectively. Properties of an amino acid sequence that may direct the targeting of a protein within or onto seed-coat tissues include, but are not limited to, signal sequences that direct intracellular, and extracellular localization of a protein, and also hydrophobic regions within a protein, that results in localization of the protein onto the seed coat. An example, which is not to be considered limiting, of a protein that is localized onto the seed-coat, is the hydrophobic protein (HP). HP is localized on the outside of the seed-coat following its synthesis within the membranous endocarp, and appears to be involved with the adherence of the endocarp to the seed-coat (see FIG. 16).

Development of the Soybean Coat

The seed coat of *Glycine max* undergoes dramatic changes in the first two and a half weeks after anthesis (flowering). At six days after anthesis (DAF; see FIG. 12(*a*)), the seed coat has a distinct epidermis (10), consisting of thin-walled cuboidal cells; an outer integument (20), consisting of up to a dozen layers of thin-walled parenchyma, and containing vascular tissue (recurrent vascular bundle) in the subhilar region; an inner integument (30), consisting of up to 6 layers of deeply-staining thick-walled parenchyma; and an endothelium (40), consisting of thin-walled cuboidal cells.

At 12 days after anthesis (FIG. 12(*b*)), there is a distinct hypodermis (15) of thin-walled cuboidal cells directly beneath the epidermis (10); the outer integument (20) has differentiated into an upper layer of thin-walled parenchyma (25), and a lower layer of thick-walled parenchyma (27); the inner integument (30), while still having very thick, deeply staining cell walls, has become stretched, and is compressed to about 3 cells thick; the endothelium (40) is also retained. Also evident in FIG. 12(b) is the endosperm (50), and the developing cotyledons (60).

Figure 12C:
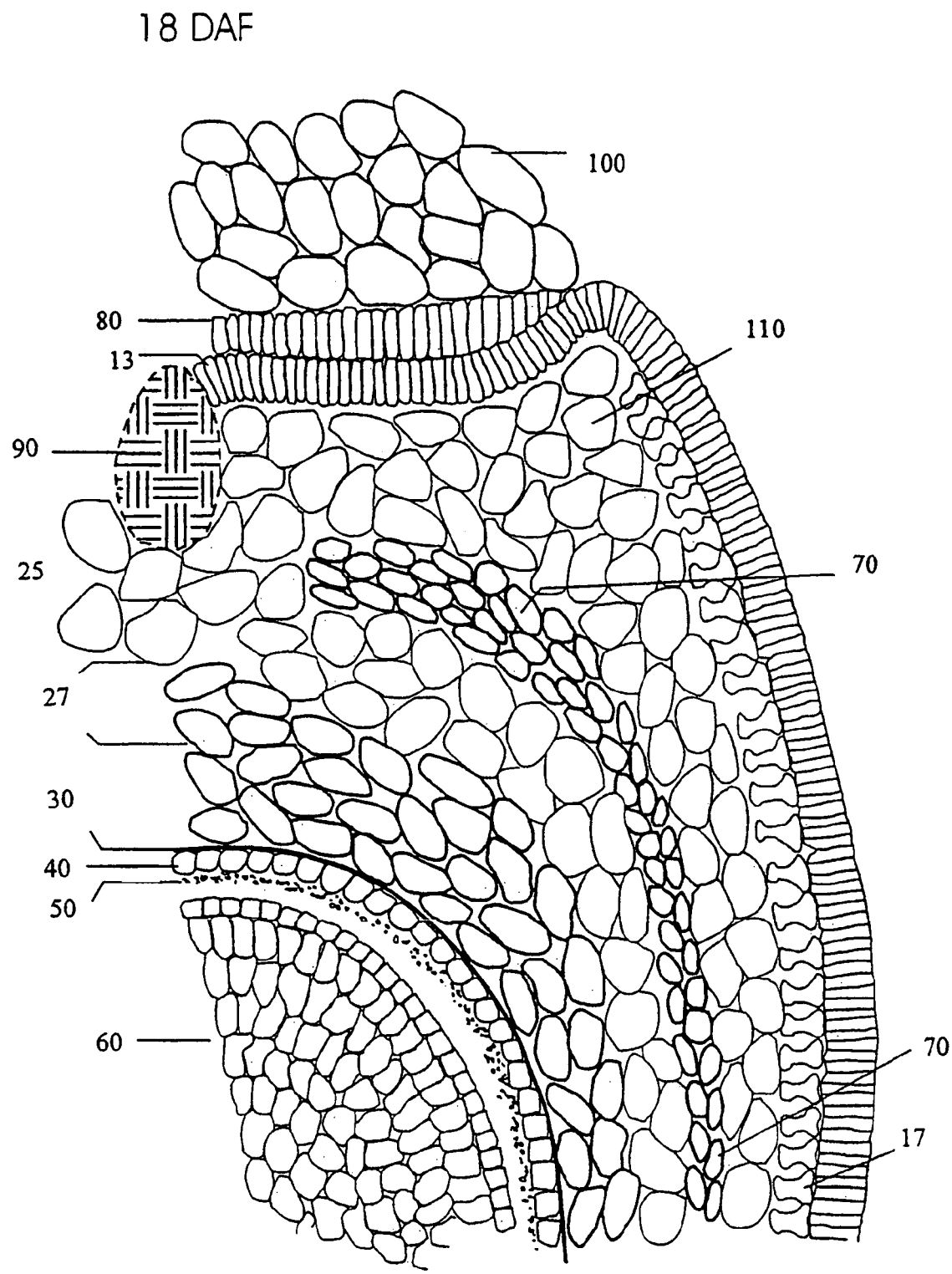

By 18 days after anthesis (FIG. 12(c)), the epidermal cells have divided and elongated to form thick-walled macrosclereids, forming a palisade layer (13). The hypodermis has differentiated into osteosclereids: thick walled cells with a characteristic I-shape (hourglass cells; 17). A prominent vascular region (70) has developed in the thin-walled parenchyma (25) of the outer integument which stops before reaching the region of the seed opposite the hilum; the thick-walled parenchyma (27) is retained. The inner integument (30) has become completely stretched and crushed, leaving a single, deeply staining wall layer directly above the endothelium (40). The hilum region contains a well-developed counter-palisade (80), and a tracheid bar (90). The seed coat remains attached to the funiculus (100). The sub-hilar region contains well-developed vascular tissue (recurrent vascular bundles; 70) and stellate parenchyma (110).

At maturity, the seed coat consists of the palisade layer (13), hourglass cells (17), a partially crushed layer of parenchyma (what remains of the outer integument), and an endothelium (40). The remnant of the inner integument (30) is often not distinguishable. The tissues of the hilum although compressed, are retained.

The stages of seed-coat development are also identified in Tables 1 and 2.

TABLE 1

Development of the Soybean Seed Coat

| | Epidermis | Hypodermis | Outer Integument | Inner Integument | Endothelium | Status of Embryo |
|---|---|---|---|---|---|---|
| 3 daf | simple cuboidal cells | — | simple parenchyma; no vascularization | 2-4 layers | simple cuboidal cells | undifferentiated proembryo |
| 6 daf | not elongated | — | simple parenchyma; recurrent vascular bundles in subhilar region | 5-6 layers; thick walled | simple cuboidal cells | endosperm starting to develop |
| 9 daf | starting to divide and elongate | cells starting to differentiate from parenchyma | upper, thinwalled parenchyma with developing vascular region; lower, thickwalled parenchyma; upper and lower parenchyma show some characteristics of aerenchyma | 2-3 cell layers, stretched, starting to compress | simple cuboidal cells | cotyledons starting to develop |
| 12 daf | division and elongation | hourglass cells developing | upper, thinwalled parenchyma with extending vascular region; lower, thickwalled parenchyma, more aerenchyma-like characteristics | 1-2 cell layers; more compression | cells starting to stretch | cotyledons shifting |
| 15 daf | cell walls thickening | hourglass cells | upper, thinwalled parenchyma with extending vascular region; lower, thickwalled parenchyma, more aerenchyma-like characteristics | layers of deeply staining wall visible | cells stretching | cotyledons expanding |
| 18 daf | palisade (macro-sclereids) | hourglass cells (I-shaped osteosclereids) | upper, thinwalled parenchyma with extending vascular region; lower, thickwalled parenchyma, more aerenchyma-like characteristics | compressed; one thick, deeply stained line | cells stretching | cotyledons expanding endosperm compressing; protein accumulation starting |
| 21 daf | palisade (macro-sclereids) | hourglass cells | upper, thinwalled parenchyma with vascular region completed; lower, thickwalled parenchyma, more aerenchyma-like characteristics | line is thinning | small, oblong, thickwalled cells | endosperm disappearing, protein and lipid accumulation in cotyledons |
| 24 daf | palisade (macro-sclereids) | hourglass cells | upper, thinwalled parenchyma with vascular region; lower, thickwalled parenchyma, more aerenchyma-like characteristics | thinning | small, oblong, thickwalled cells | endosperm no longer distinct, protein and lipid accumulation continue |
| 30 daf | palisade (macro-sclereids) | hourglass cells | upper and lower parenchyma starting to compress | thin, deeply stained line visible | small, oblong, thickwalled cells | protein and lipid accumulation slowing |
| 45 daf | palisade (macro-sclereids) | hourglass cells | parenchyma partially collapsed, upper and lower parenchyma not distinct, vascular tissue not distinguishable | not distinguishable | small, oblong, thickwalled cells | mature cotyledons |

TABLE 2

Position and Levels of Starch, Protein and Lipid in Relation to Seedcoat Development in Soybean

| | Developmental Information | Status of Embryo | Starch Accumulation |
|---|---|---|---|
| 1 daf | undifferentiated integument and endothelium distinguishable | | throughout seedcoat (also in pod, funiculus & senescing floral parts) |
| 3 daf | inner and outer integument, vascular bundles visible | | throughout seedcoat (> in outer integument) except epidermis & recurrent vascular bundles (also in funiculus & pod) |
| 6 daf | inner and outer integument, vascular bundles at hilum | embryo starting to expand | outer integument & stellate parenchyma (pod, trichomes & funiculus) |
| 9 daf | inner, integument stretched, vascular bundles expanding away from hilum; outer integument differentiating into an upper and lower region | cotyledons are small and beginning to shift | gradient in epidermis; very few granules in bottom half of seedcoat, stellate parenchyma, outer integument |

TABLE 2-continued

Position and Levels of Starch, Protein and Lipid in Relation to Seedcoat Development in Soybean

| | | | |
|---|---|---|---|
| 12 daf | inner integument is crushed, epidermis starting to differentiate into palisade and hypodermis, hypodermis starting to differentiate into hourglass cells | cotyledons have shifted, fill embryonic space | palisade (at hilum), stellate parenchyma, differentiating hourglass cells, outer (outer and inner) and inner integument (funiculus) (starting in cotyledons) |
| 15 daf | epidermis differentiated into palisade and hypodermis differentiated into hourglass cells, upper parenchyma differentiated into upper and lower region | | palisade, hourglass cells, stellate parenchyma, outer integument (outer region) (cotyledon epidermis) |
| 18 daf | palisade and hourglass cells fully developed, vascular region is very prominent, seed coat is fully expanded | cotyledons have fully expanded | palisade, hourglass, sparse in stellate, sparse in outer integument (outer and inner) (cotyledons) |
| 21 daf | same as in 18 | | palisade, sparse in stellate and lower potion of upper parenchyma & vascular parenchyma (*also in layer outside of palisade) (cotyledons) |
| 24 daf | same as in 18 | | palisade, sparse in lower region of upper parenchyma, starting in endothelium (*also in layer outside of palisade) (cotyledons) |
| 30 daf | outer parenchyma region has disappeared, stellate parenchyma present, vascular regions still present, endothelium prominent | | endothelium (also endothelium around hypocotyl) |
| 45 daf | outer parenchyma disappeared, stellate parenchyma present, inner integument collapsed, endothelium very prominent | | endothelium (also endothelium around hypocotyl) |

| | Protein Accumulation | Lipid accumulation |
|---|---|---|
| 1 daf | no distinct protein bodies | |
| 3 daf | no distinct protein bodies | few small lipid droplets in funiculus, nothing in seedcoat |
| 6 daf | no distinct protein bodies | few small droplets in outer integument |
| 9 daf | no distinct protein bodies | small droplets in funiculus and counter palisade, sparse in outer integument |
| 12 daf | no distinct protein bodies in seedcoat but starting in cotyledons | |
| 15 daf | protein bodies in cotyledons getting larger | |
| 18 daf | | |
| 21 daf | | |
| 24 daf | | |
| 30 daf | many large and small protein bodies filling cotyledons | |
| 45 daf | | |

Early Development of the Tobacco Seed Coat

At 6 days after anthesis, the tobacco seed coat consists of an epidermis of very large, thin walled cells; a layer of parenchyma cells up to 6 cells thick; and an endothelium of thin-walled, cuboidal cells. By 10 days after anthesis, the inner walls of the epidermis have thickened significantly, with 2-3 layers discernible; the thin-walled parenchyma has become reduced to 3-4 cells thick due to stretching of the layer as the seed expands; and the endothelial cells have become thinner and elongated. At 22 days after anthesis, the epidermal cells have stretched and elongated to accommodate the expanding seed, and the parenchyma and endothelium have elongated and fused into a crushed layer with few individual cells distinguishable.

Seed-coat Cryptic Promoter

There are several lines of evidence that suggest that the seed-coat expression of GUS activity in the plant T218 is regulated by a cryptic promoter. The region surrounding the promoter and transcriptional start site for the GUS gene are not transcribed in untransformed plants. Transcription was only observed in plant T218 when T-DNA was inserted in cis. DNA sequence analysis did not uncover a long open reading frame within the 3.3 kb region cloned. Moreover, the region is very AT rich and predicted to be noncoding (data not shown) by the Fickett algorithm (Fickett, 1982, *Nucleic Acids Res.* 10, 5303-5318) as implemented in DNASIS 7.0 (Hitachi). Southern blots revealed that the insertion site is within the *N.*

*tomentosiformis* genome and is not conserved among related species as would be expected for a region with an important gene.

As this is the first report of a cryptic promoter specific to seed-coat tissues in plants, it is impossible to estimate the degree to which cryptic promoters may contribute to the high frequencies of promoterless marker gene activation in plants. It is interesting to note that transcriptional GUS fusions in *Arabidopsis* occur at much greater frequencies (54%) than translational fusions (1.6%, Kertbundit et al., 1991, *Proc. Natl. Acad. Sci. USA* 88, 5212-5216). The possibility that cryptic promoters may account for some fusions was recognized by Lindsey et al. (1993, *Transgenic Res.* 2, 33-47).

The results disclosed herewith confirms others (Gheysen et al., 1987, *Proc. Natl. Acad. Sci. USA* 84, 6169-6173 and 1991, *Genes Dev.* 5, 287-297) that T-DNA may insert into A-T rich regions as do plant transposable elements (Capel et al., 1993, *Nucleic Acids Res.* 21, 2369-2373). We illustrate that promoters of plant genes are also A-T rich raising speculation that gene insertions into these regions could facilitate the rapid acquisition of new regulatory elements during gene evolution.

The insertion of functional genes into the nuclear genome and acquisition of new regulatory sequences has already played a major role in the diversification of certain genes and the endosymbiosis of organelles. In plants, most organellar proteins are nuclear encoded due to the ongoing transfer of their genes into the nucleus (Palmer, 1991, In Bogorad L and Vasil IK (eds) The Molecular Biology of Plastids, Academic Press, San Diego, pp 5-53). Recently, it has been shown that the cox 2 gene of cowpea (Nugent and Palmer, 1991, *Cell* 66, 473-481) and soybean (Covello and Gray, 1992, *EMBO J.* 11, 3815-3820) were transferred from mitochondria to nucleus without promoters by RNA intermediates. The results disclosed herewith, with T-DNA-mediated gene fusions reveal the facility with which promoters can be acquired by incoming genes. The presence of cryptic promoters and diverse regulatory elements in the intergenic regions may insure that genes rapidly achieve the features needed to meet the demands of complex multicellular organisms.

Other Seed-coat, and Seed-coat-associated Promoters

Transcripts encoding seed coat specific genes were isolated from seed-coat cDNA libraries. These cDNA transcripts were then used to identify the corresponding structural genes and associated promoters from genomic DNA libraries. These promoters, genes and gene products have been isolated and characterized Examples of such genes include, but are not limited to, SC4, SC20, SC21, a peroxidase cloned from the Ep locus, and HP (hydrophobic protein). It is to be understood that this seed-coat library comprises tissues typically found within the seed-coat and tissues adhering to the seed-coat such as the membranous endocarp and cells found in the funicular region such as arial cells (see above for full definition of seed-coat).

Ep Locus Peroxidase

The amount of peroxidase activity present in seed coats may vary substantially among different cultivars. The presence of a single dominant gene Ep causes a high seed coat peroxidase phenotype. Homozygous recessive epep plants are ~100-fold lower in seed coat peroxidase activity which results from a reduction in the amount of peroxidase enzyme present, primarily in the hourglass cells of the subepidermis (Gijzen et al., 1993). In plants carrying the Ep gene, peroxidase is heavily concentrated in the hourglass cells (osteosclereids; which form a highly differentiated cell layer with thick, elongated secondary walls and large intercellular spaces).

A seed-coat peroxidase gene, corresponding to the Ep locus, was obtained from a soybean seed-coat library. The genomic DNA sequence comprises four exons spanning bp 1533-1752 (exon 1), 2383-2574 (exon 2), 3605-3769 (exon 3) and 4033-4516 (exon 4) and three introns comprising 1752-2382 (intron 1), 2575-3604 (intron 2) and 3770-4516 (intron 3), of SEQ ID NO:2. Features of the upstream regulatory region of the genomic DNA include a TATA box centred on bp 1487; a cap signal 32 bp down stream centred on bp 1520. Also noted within the genomic sequence are three polyadenylation signals centred on bp 4520, 4598, 4663 and a polyadenylation site at bp 4700. The promoter region of the genomic sequence comprises nucleotides 1-1532 of SEQ ID NO:2 (see co-pending U.S. patent application Ser. Nos. 08/723,414 and 08/939,905, both of which are incorporated by reference).

Expression of Ep is first detected at 6 DPA in the thin-walled parenchyma of the outer integument, adjacent to the thick-walled parenchyma, and flanking the hilum region. By 9 DPA a thin band of expression extends around the entire seed coat, at the junction of the thin-and thick-walled parenchyma. Expression shifts to the hourglass cells as they begin to develop, at 12 DPA (see FIGS. 13(*e*), (*f*) and (*g*)).

Expression of a gene under the control of the Ep (peroxidase) promoter (nucleotides 1-1532 of SEQ ID NO:2, also see co-pending U.S. patent application Ser. No. 08/723,414 and 08/939,905, both of which are incorporated by reference) is observed within the seed-coat from 6 to 18 days after anthesis is shown in FIGS. 13(*d*) to (*g*).

Hydrophobic Protein (HP)

Soybean HP is an 8.3 kD protein consisting of 80 amino acids rich in hydrophobic residues and entirely lacking methionine, phenylalanine, tryptophan, lysine and histidine residues (see FIG. 15). The amino acid sequence shows no significant homology to any known proteins (Odani et al., 1987, *Eur J Biochem* 162, 485-491).

Figure 17A:
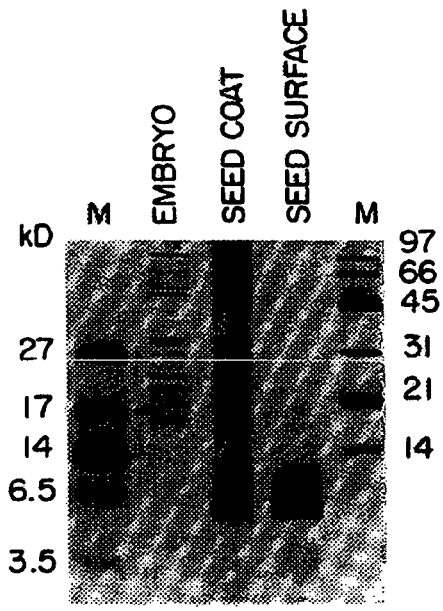
FIG. 17 shows a silver stained SDS-PAGE analysis of protein extracts from seed tissues and surface. Lanes marked 'M' indicate protein standards, and their corresponding mass in kilodaltons is also provided.
Figure 17B:
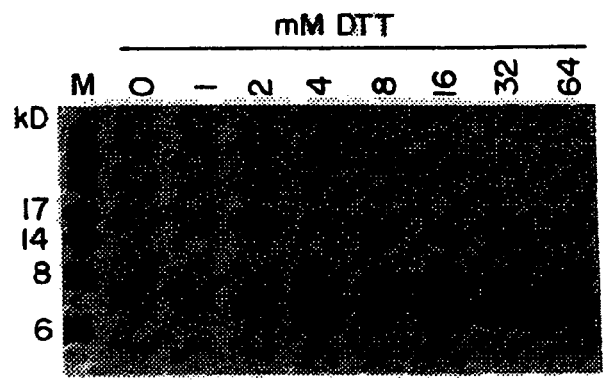

To determine the composition of proteins deposited on the soybean seed surface, seeds were washed with a detergent-buffer solution and the extracted peptides were separated by SDS-PAGE. Protein extracts from the seed coat and embryo were also prepared for comparison. These results are shown in FIG. 17 (*a*). The embryo and seed coat extracts contained many proteins covering a wide molecular mass range. In contrast, extracts from the seed surface were dominated by a few low molecular mass proteins. FIG. 17(*b*) demonstrates that HP extraction and separation by SDS-PAGE is dependant on dithiothreitol (DTT).

Even though HP is an abundant seed constituent and a potent allergen, there have been no studies on the expression or localization of the protein or any description of the corresponding gene. This is the first report on the isolation and characterization of HP cDNA (SEQ ID NO:6) and the corresponding genomic clone (SEQ ID NO:7), the pattern of gene expression (FIG. 10(*e*)), and the localization of the protein (FIG. 14(*b*)) and its effect on seed luster (FIG. 16). FIG. 14(*c*) shows that the presence of surface protein is related to the luster, or light reflective properties of the seed surface. Surface extracts from shiny seeded phenotypes usually contained far less protein than dull seeded extracts. Moreover, there were large differences in the amount of protein present on the seed surfaces of the two bloom phenotypes examined.

These results also show that the outermost components of the seed coat are in fact derived from the inner layer of the pod wall (see FIG. 14(*a*)).

The cDNA and genomic copies of the seed-coat associated HP gene were obtained from lambda libraries prepared from cultivar Harosoy 63. The genomic DNA sequence comprises a promoter region from 1-2526 of SEQ ID NO:7. Within this promoter region are located clustered direct repeats (between 1-586; see also FIG. 11 (*c*). and a TATA box located at position 2442-2447. The ORF for HP is between 2526-2881, with the translational start site at 2526, followed by a signal sequence from 2526-2642, and the mature protein from 2643-2881. Also noted within the genomic sequence are six polyadenylation signals and a polyadenylation site at bp 3193.

Figure 10E:
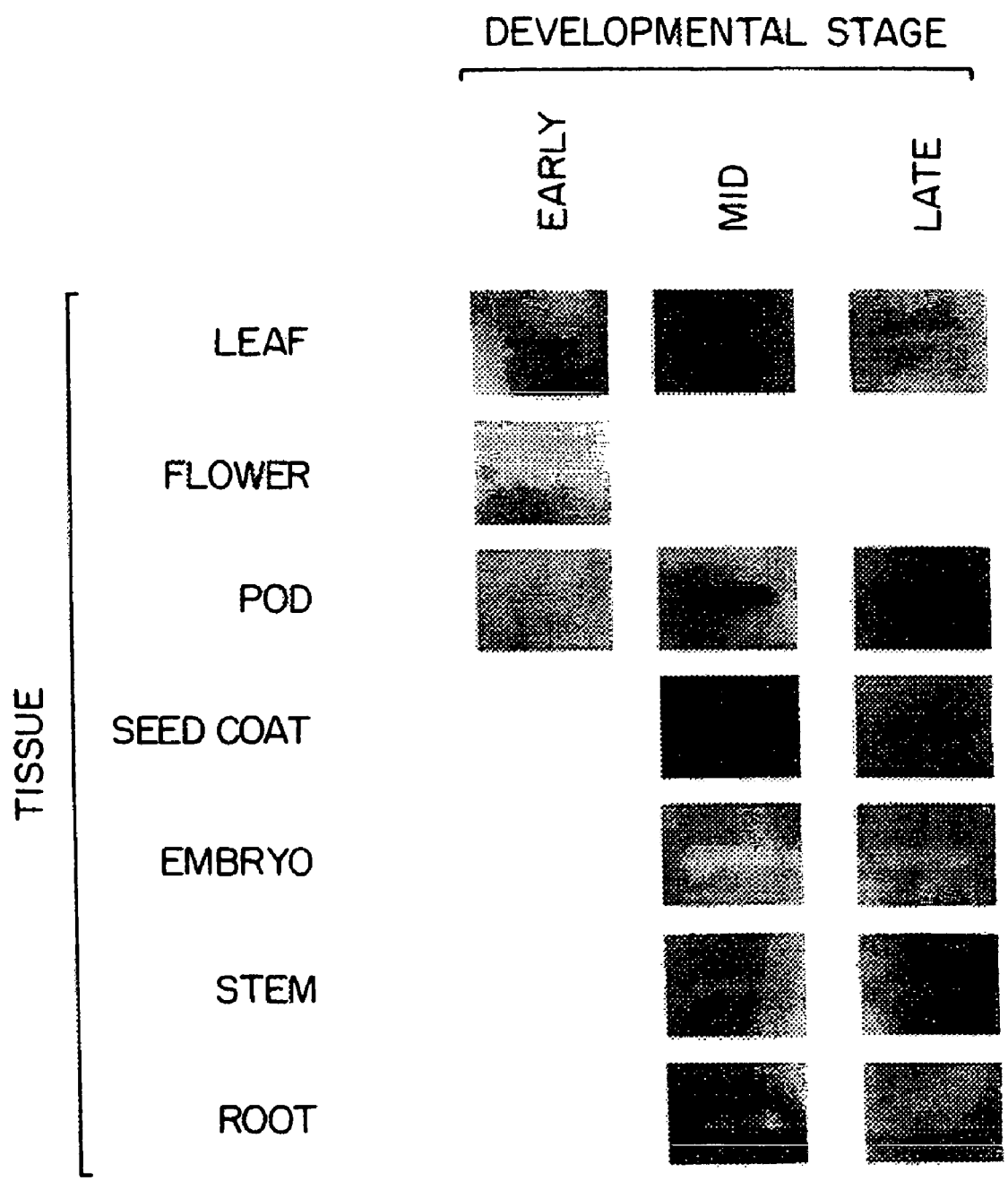
FIG. 10 shows a Northern analysis of the expression of several of the genes of the present invention within developing seed coats, embryo, pod, flower, root, stem and leaf tissues.
Figure 10F:
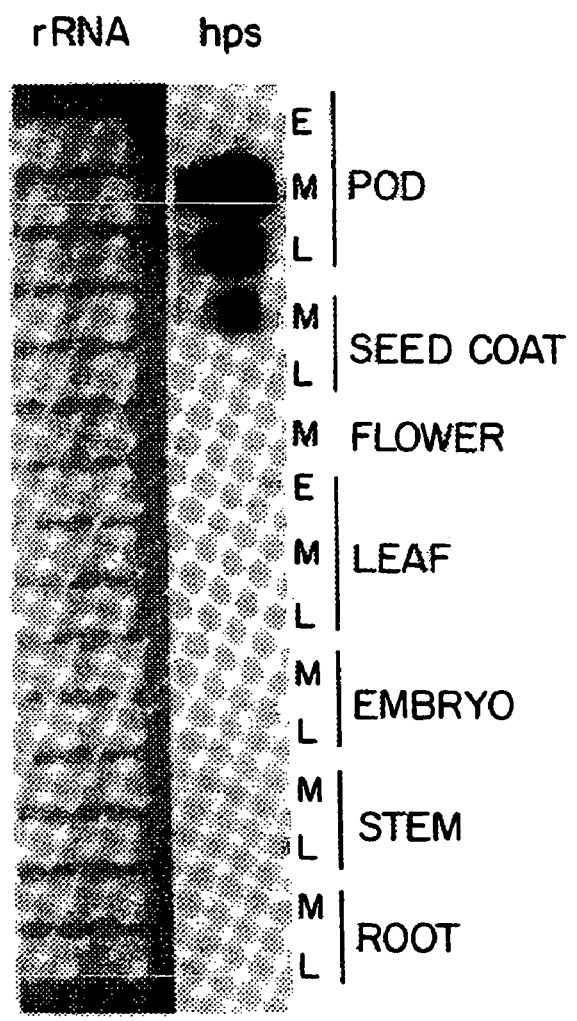
Figure 10G:
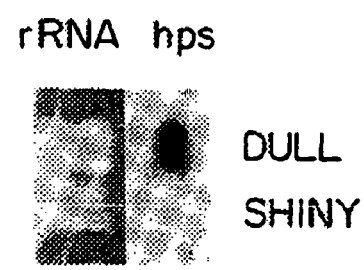

Developmental and tissue specific expression patterns for the HP gene were determined by RNA blot analysis and in situ hybridization. Representative RNA blots, probed with HP cDNA, are shown in FIGS. 10(*e*) and (*f*). These results show that HP is highly expressed in the pod during the mid to late stages of seed development. Hybridization signals were also observed in seed coat RNA samples. No expression was evident in the flower, leaf, embryo, stem, or root. We also compared HP transcript levels of two different seed luster phenotypes that differed in the amount of HP present on their seed surfaces. FIG. 10(*g*) shows that HP mRNA levels are several fold greater in dull seeded plants that accumulate large amounts of HP on the seed surface when compared to shiny seeded plants that have only trace amount of HP on the seed surface. Faint signals, corresponding to low. HP transcript levels, were detectable in shiny seeded phenotypes after prolonged exposure times (not shown).

Localization of HP gene expression by in situ hybridization is shown in FIGS. 14(*b*), (*c*) and (*d*). At six days post anthesis (DPA) expression of HP is limited to the membranous inner layer of the pericarp. By 12 DPA expression is very strong and the inner epidermis is showing signs of becoming detached from the rest of the pericarp and, in places, is adhering to the seed surface. Tissue sections from this stage of development also showed strong hybridization signals in the sclerenchyma, indicating that HP expression occurs throughout the endocarp. Portions of membranous endocarp adhere to the seed during the course of development (see FIGS. 14(*a*) and 16) and thus constitute a newly identified component of the seed coat of mature, fully developed soybeans. The deposition of this material alters the physical properties and the composition of the seed surface, as shown by SDS-PAGE analysis (FIGS. 17(*a*), (*b*) and (*c*)) and by scanning electron microscopy (FIG. 16). A comparison of dull- and shiny-seeded cultivars reveals that the HP gene controls this phenotypic trait in soybeans.

In FIG. 14(*b*) can be seen the expression of a gene under the control of the HP promoter, The promoter (nucleotides 1-2526 of SEQ ID NO:7) is active within the membranous endocarp associated with the outer seed-coat.

SC4, 20 and 21

Genes expressing specifically in seed coat tissue were isolated from a seed coat cDNA library obtained from seed coats in later stages of development.

SC4

Figure 19C:
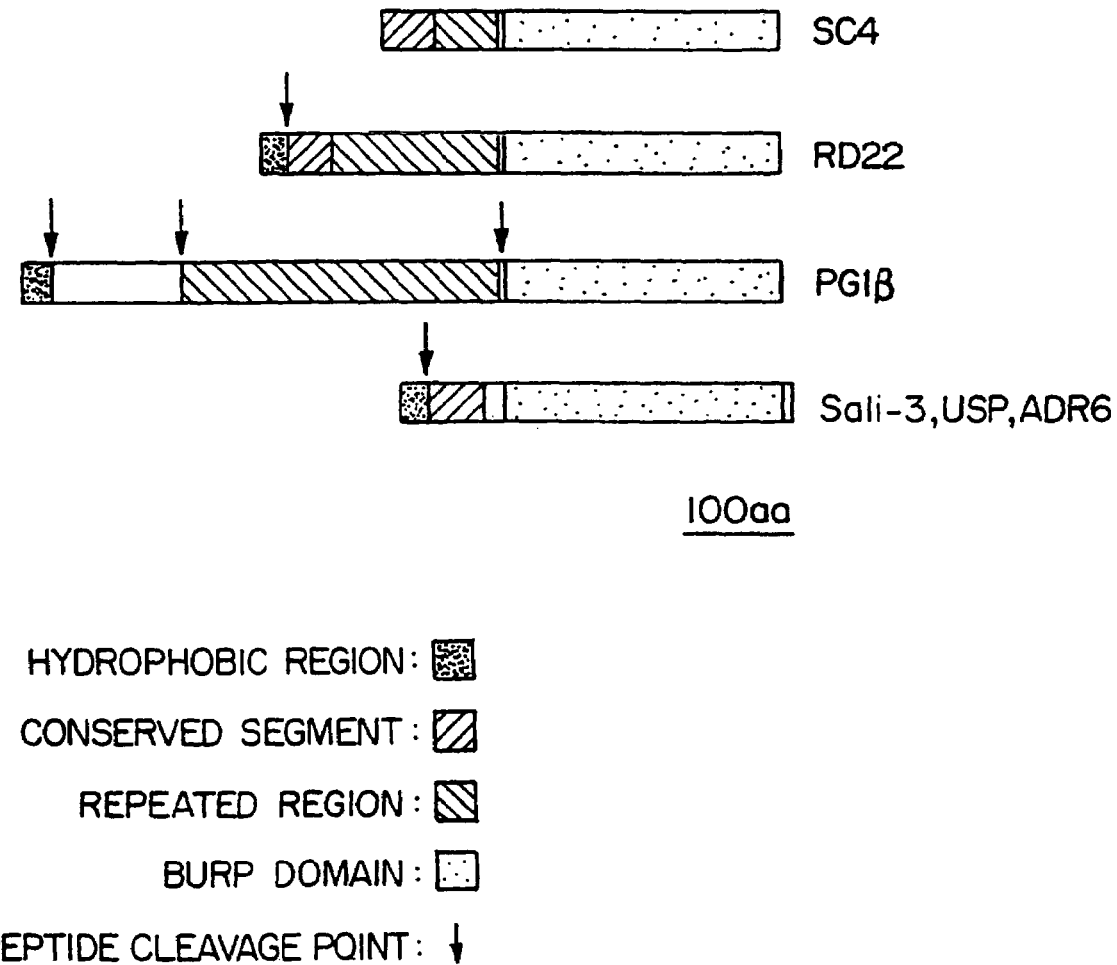
FIG. 19(c) shows the structual similarity between SC4 protein and the BURP domain proteins.

The deduced protein sequence from the SC4 cDNA (FIG. 19(*a*); SEQ ID NO:3) consists of 289 amino acids and has a molecular mass of 31.9 kDa and a predicted pI of 7.95. Three puatative glycosylation sites are present at positions 92, 128 and 269. The putative polypeptide encoded by SC4 exhibits similarity with proteins that comprises a BURP domain (see FIG. 19(*b*)). The BURP domain is a long carboxyl terminal domain containing a number of highly conserved amino acids (Hattori J. et al., 1998. Mol. Gen. Genet. 259: 424-428). The genomic sequence of sc4 is provided in SEQ ID NO:9 (also see Restriction map FIG. 11(*d*)) and comprises a promoter from nucleotides 1-5514 of SEQ ID NO:9.

The expression of a gene under control of the SC4 promoter (nucleotides 1-5514 of SEQ ID NO:9) within soybean seed coat at 3 days after anthesis is shown in FIG. 13(*a*). The activity of the promoter is localized within the inner integument (arrow). Other areas of brightness in this figure include the recurrent vascular bundles in the funiculus, and the trichomes of the pod (the bright areas are due to the birefringence of crystalline areas in the cell walls, and are also present in the negative control; data not shown).

RNA samples from seed coat, embryo, stem, root, leaf, pod and flower were hybridized with a radiolabelled SC4 cDNA probe (FIG. 10(*a*)) to determine organ specificity of the expression of SC4. The sc4 transcript was only expressed in the seed coat organ. It was estimated that the size sc4 mRNA was 1.2 kb (data not shown).

Figure 20:
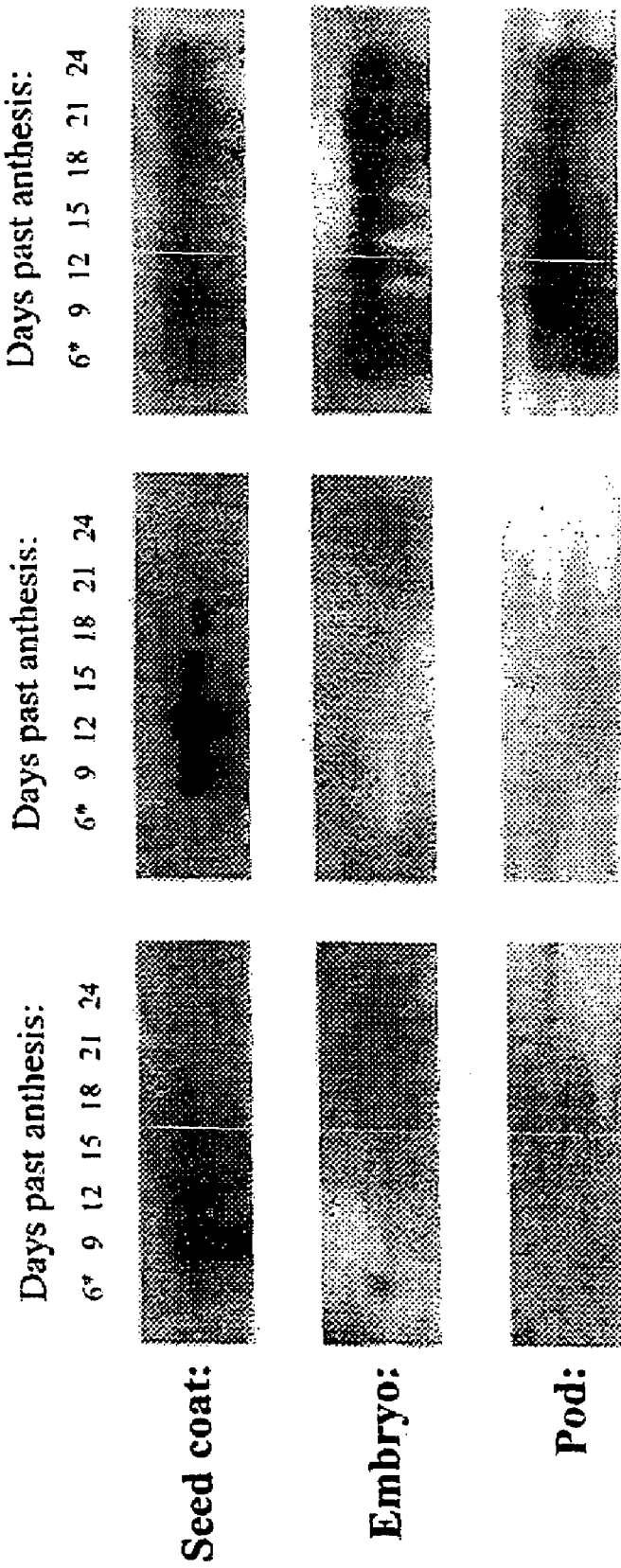
FIG. 20 shows Northern blot analysis of SC4 and SC20 mRNA accumulation in seed coat embryo and pod organs of soybean. 10 μg total RNA from seed coat, embryo and pod organs between 6-24 days past anthesis were hybridized with radiolabled probes. For day 6, total RNA was prepared from whole seeds. Each blot was hybridized with a SC4 cDNA probe, FIG. 20(a), a SC20 cDNA probe FIG. 20(b), and an 18S rRNA probe Figure (c).

Northern blot analysis was carried out to determine the temporal expression pattern of sc4. RNA from seed coat, embryo and pod organs between 6-24 dpa were hybridized with a radiolabelled SC4 cDNA probe. No gene expression was observed in any of the embryo development stages examined (FIG. 20(*a*)). sc4 expression was apparent in the seed by 6 dpa. After 6 dpa the expression of sc4 in the seed coat increased ~4-fold to its maximum detected level between 9-12 dpa. By 15 dpa sc4 expression had decreased by ~2.5-fold dpa and continued to decline to just detectable levels by 18 dpa (FIG. 3.7). Expression of sc4 could only be detected in the seed coat at 21-24 dpa when the filter was over-exposed. Gene expression of sc4 in the pod was detected from 12-21 dpa only after over-exposure of the filter (data not shown).

To analyse the distribution of sc4 expression with respect to cell differentiation during seed coat development in situ hybridization was performed on seed sections from 3-24 dpa seeds. sc4 was expressed throughout the inner integument of the seed coat at 3 dpa (FIGS. 13(*a*) and 21). By 6 dpa the expression pattern of sc4 had changed, and was localized to the outer integument parenchyma but not to the vascular tissue embedded within this layer. sc4 expression in the outer integument was maintained until 18 dpa after which time no further expression was detected (see Table 4 in Examples). In concurrence with northern blot analysis, the in situ hybridization results revealed that sc4 expression increased to a maximum between 9-12 dpa and decreased thereafter (Table 4, in Examples). In addition, expression of sc4 was not observed in the embryo of seed at 3-6 dpa.

Expression of a gene under the control of the SC4 promoter (1-5514 of SEQ ID NO:9) is seen in FIGS. 13(*a*) and 21.

Figure 22:
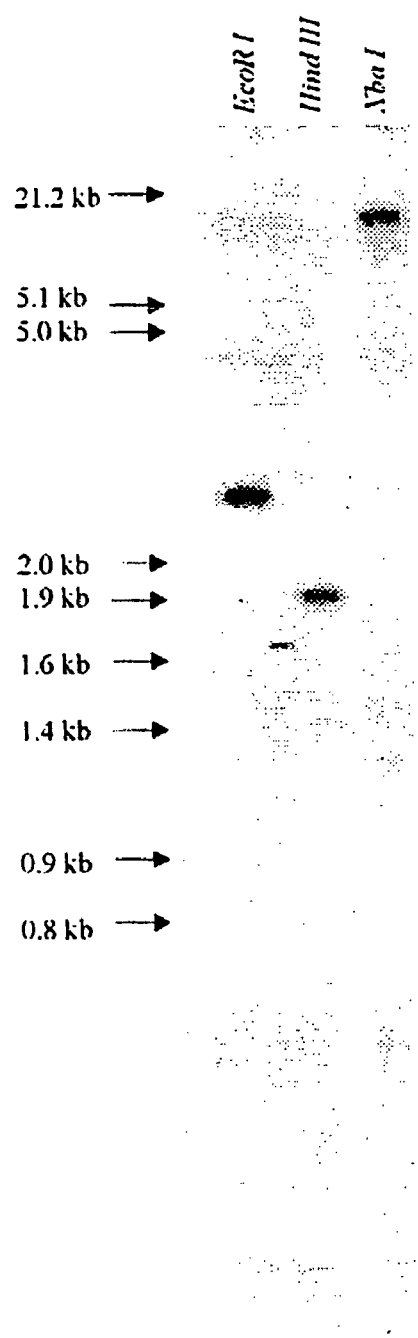
FIG. 22, shows Southern blot analysis of SC4.
Figure 22:
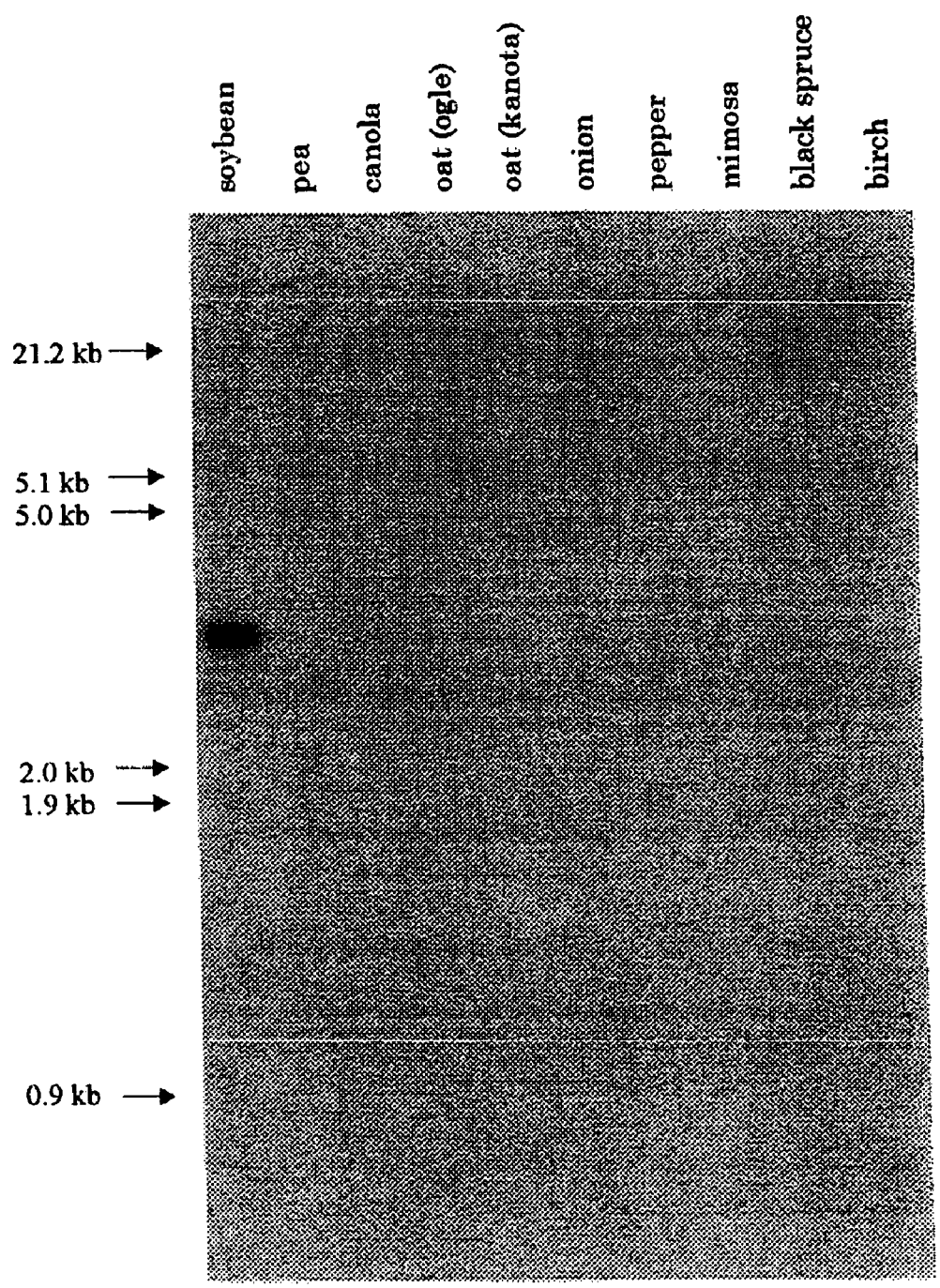

Southern blot analysis was carried out to examine the gene family composition of sc4. Soybean genomic DNA was cleaved with Eco RI, Hind III and Xba I. which do not have recognition sites in the SC4c cDNA sequence. Under conditions of low to high stringency (i.e., from 40-10° C. below Tm of the probe) the SC4 cDNA probe hybridized to a single band (FIG. 22) and therefore sc4 appears to be a single gene.

Southern blot analysis was also performed to determine the occurrence of sc4 within the following plant species: pea (*Pisum sativum*), canola (*Brassica napus*), oat (*Avena sativa*), onion (*Allium cepa*), pepper (*Capsicum annuum*), Mirnosa sp. (*Mimosa pudica*), black spruce (*Picea mariana* (Mill) B.S.P.), birch (*Betula pendula* Roth). The genomic DNA was digested with Eco RI. Under all stringency conditions it was observed that the radiolabelled SC4 cDNA probe hybridized to only soybean genomic DNA (FIG. 22(*b*)). Further analysis of more related species to soybean need to be carried out.

SC20

Figure 23A:
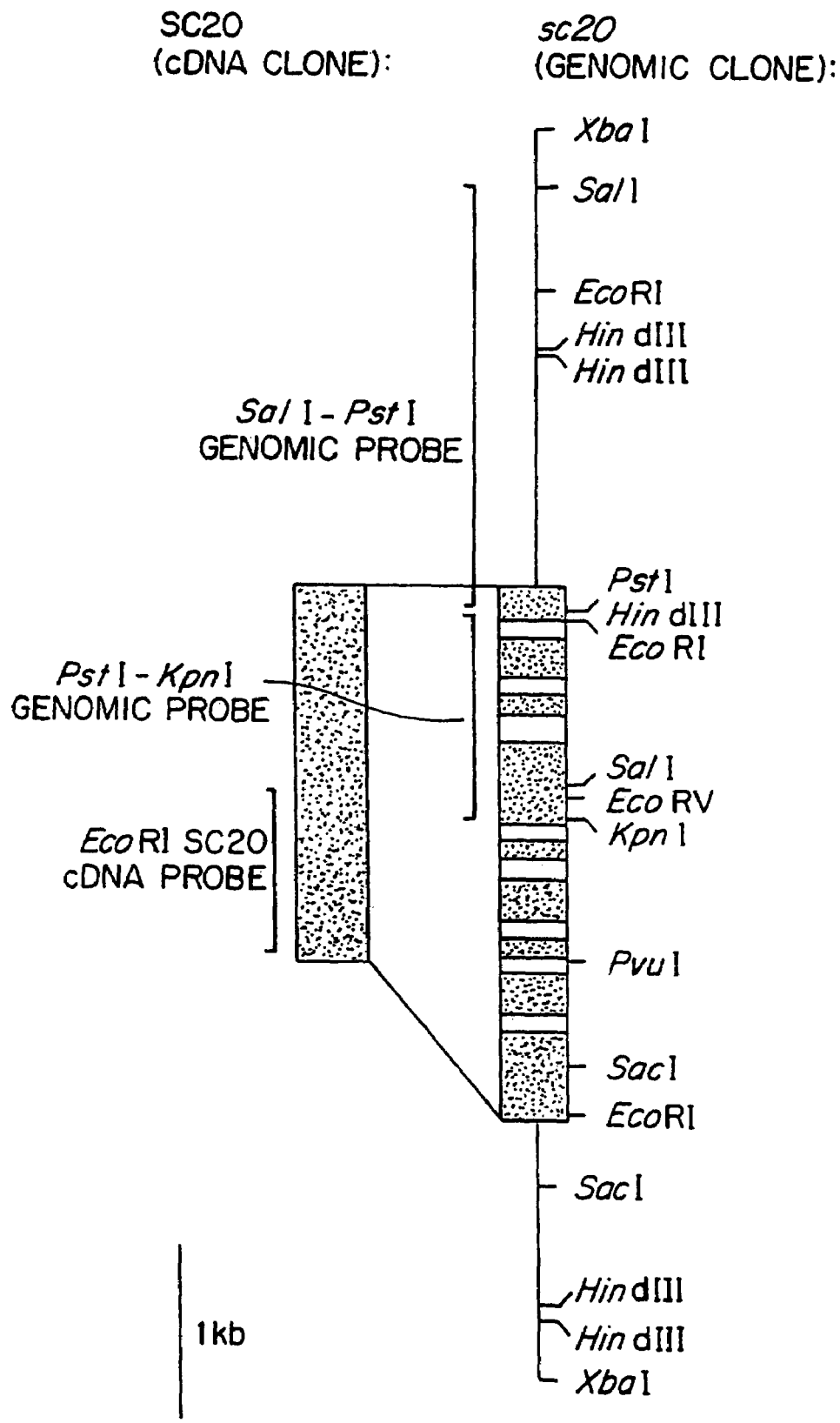
FIG. 23(a) is a restriction map of sc20.
Figure 23C:
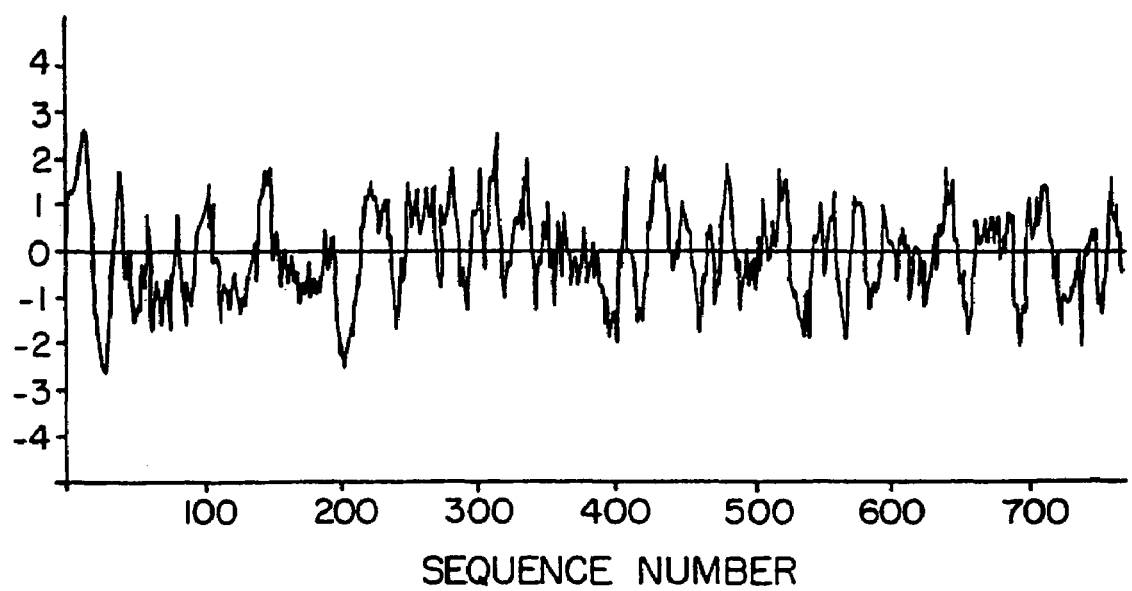
FIG. 23(c) shows the hydrophobic plot of SC20 protein, where hydrophobic regions possess a positive sign, and hydrophilic regions possess a negative sign.

The open reading frame of SC20 encodes a putative protein of 770 amino acid residues with a calculated molecular mass of 82.688 kDa and a predicted pI of 6.93. The predicted protein has ten potential N-glycosylation sites (FIG. 23(*b*)). The hydropathy profile (FIG. 23(*c*)) of SC20 protein revealed that the first 23 amino acids constitute a hydrophobic region typical of an eukaryotic signal peptide. From northern blot analysis, the SC20 cDNA clone hybridizes to a ~2.5 kb transcript.

The genomic sc20 clone is 7235 bp in length (see FIG. 23(*a*) for restriction map, and SEQ ID NO:8). Alignment of sc20 genomic and SC20 cDNA sequences revealed that sc20 contained eight introns of 94 bp, 101 bp, 185 bp, 80 bp, 154 bp, 112 bp, 110 bp and 93 bp respectively (FIG. 23(*a*)). A search of the 5' upstream region of sc20 revealed three potential transcription start sites at positions 1085, 1156 and 2272. The promoter region of sc20 spans nucleotides 1-2450 of SEQ ID NO:8.

Sequence comparisons (FIG. 23(*d*)) revealed that the putative polypeptide encoded by SC20 was similar to plant proteins belonging to the Pyrolysin family in the clan of serine proteases known as the subtilases (Barrett A. J. and Rawlings N. D., 1995. Arch. Biochem. Biophys. 318:247-250; Siezen, R. J. and Leunissen, J. A. M. 1997. Protein Sci. 6: 501-523.). The SC20 protein comprises 3 domains: a signal peptide of 23 residues followed by a prosequence of 93 residues and a mature domain of 654 residues. The predicted mature domain of SC20 has a calculated molecular weight of 69.918 kDa and an isoelectric point of 6.34.

Northern blot analysis was carried out to determine specificity of sc20 expression in various soybean organs i.e., seed coat, embryo, stem, root, leaf, pod and flower (FIG. 10(b)). sc20 has seed coat-specific expression as its mRNA was detected only in the seed coat organ. The sc20 transcript was determined to be approximately 2.5 kb (data not shown). Even after prolonged exposure of the filter, no sc20 transcripts was detected in any of the other plant organs.

Figure 24A:
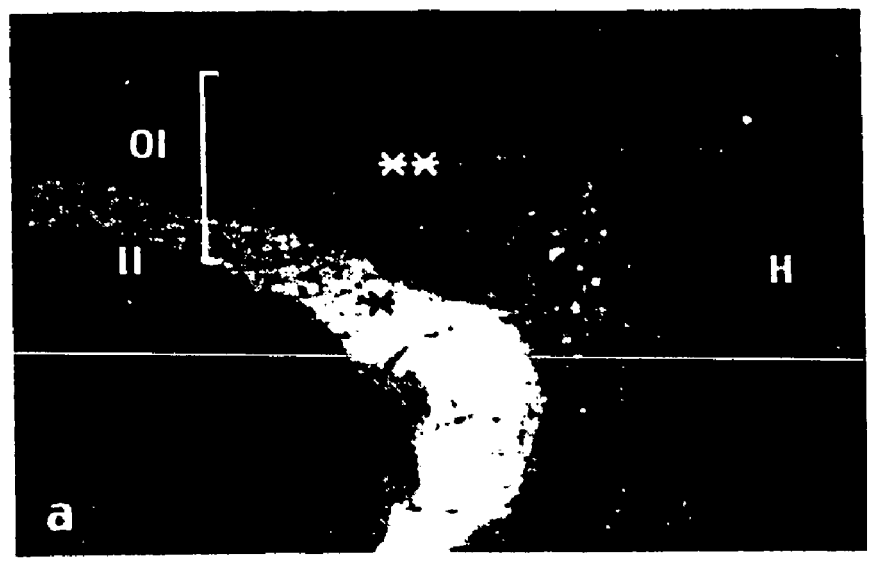
FIG. 24 shows localization of SC20 mRNA in seed coats of soybean by in situ hybridization. Transection of seed coats at 12 days past anthesis hybridized to Antisense, FIG. 24(a), and Sense, FIG. 24(b), SC20 radiolabelled RNA probes. Abbreviations: H Hilumi, II inner integument, OI outer integument, * thick walled parenchyma, ** thin walled parenchyma. Bar equals 100 μm.
Figure 24B:

Northern blot analysis was performed to determine the temporal gene expression pattern of sc20 in seed coat, embryo and pod organs of soybean. Total RNA prepared from organs between 6-24 dpa were probed with a radiolabelled SC20 cDNA probe. sc20 expression was detected at 9 dpa and rose 1.5 fold to its maximum observed level at 12 dpa (FIG. 24). By 18 dpa accumulation of sc20 mRNA had decreased 4-fold. Prolonged exposure of the filter enabled detection of sc20 expression at 6 dpa and 21-24 dpa. No gene expression was observed at any stage of embryo or pod development examined even after prolonged exposure of the filters. This confirmed that sc20 expression was seed coat-specific.

In situ hybridization was carried out to analyse the spatial gene expression pattern of sc20 within the seed coat between 3-24 dpa. Seed sections were hybridized with radiolabelled sense and anti-sense SC20 RNA probes. No birefringent cell structures were evident in the seed sections used (FIG. 24).

Figure 13A:
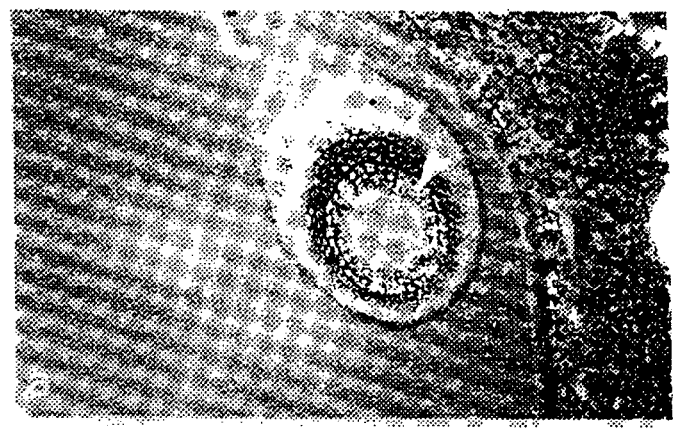
FIG. 13 shows in situ hybridization results obtained with seed coats of *Glycine max* at different developmental stages, and probed as follows.
Figure 13B:
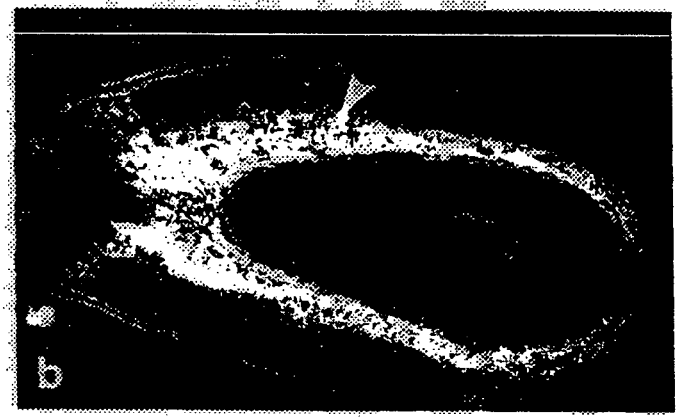

Gene expression of sc20 was localized to the thick-walled parenchyma of the outer integument (see FIGS. 13(b) and 24). The temporal expression pattern of 9-21 dpa expression with an observed peak at 12 dpa was almost identical to that determined by northern blot analysis (Table 4, in Examples). sc20 transcripts were not detected in the embryo between 3-6 dpa. The in situ hybridization results of the seed sections concur with the northern blot analysis that within the seed organ sc20 is expressed only in the seed coat organs.

Expression of gene under control of the SC20 promoter (1-245 of SEQ ID NO:8) is seen in FIGS. 13(b) and 24.

Figure 25:
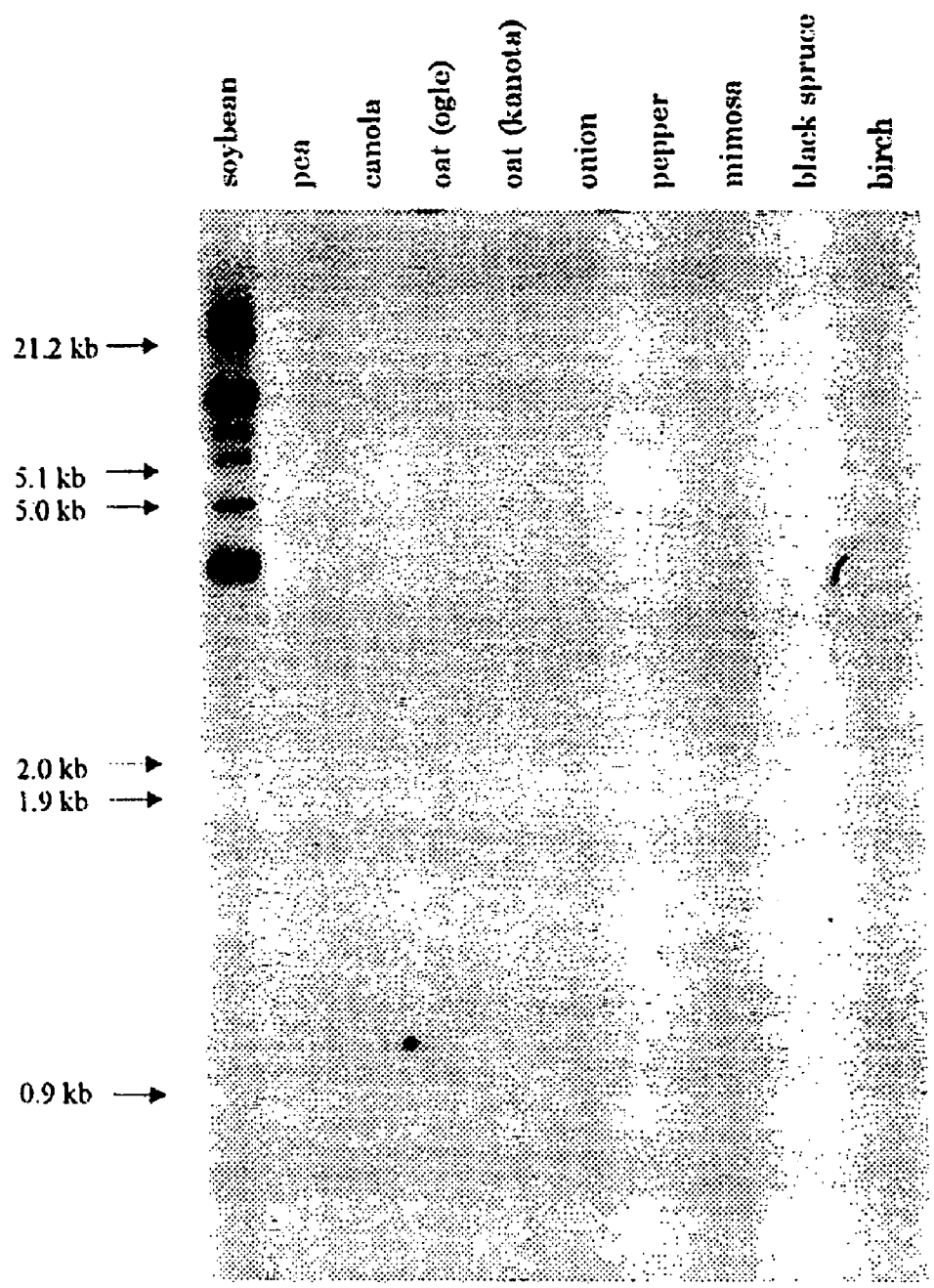
FIG. 25 shows Southern blot analysis of sc20.

Southern blot analysis was performed to ascertain whether sc20 is a single gene or a member of a gene family. Soybean genomic DNA was cleaved with Eco RI, Hind III, Xba I and Eco RV which have three, four, two and one recognition site(s) respectively in the sc20 clone (see FIG. 23(a)). Under conditions of high stringency to detect genes with at least 90% similarity to sc20 the probe hybridized to a single band (FIG. 25(b)). Under medium stringency conditions to observe genes with 80% similarity to sc20 it was observed that the SC20 probe annealed to 2-3 bands for each digest (FIG. 25(a)). Under conditions of low stringency i.e., 40° C. below Tm the SC20 probe hybridized to several more bands from each digest (data not shown). This suggested that sc20 is a member of a small gene family composed of 2-3 members and that the soybean genome contains several genes which are more distantly related to sc20.

Southern blot analysis was also performed to determine the distribution of sc20 among a number of diverse plant species i.e., pea (*Pisum sativum*), canola (*Brassica napus*), oat (*Avena sativa*), onion (*Allium cepa*), pepper (*Capsicum annuum*), Mimosa sp. (*Mimosa pudica*), black spruce (*Picea mariana* (Mill) B.S.P.), birch (*Betula pendula* Roth). The genomic DNA was restricted with Eco RI. The SC20 cDNA probe hybridized to only the genomic DNA of soybean (FIG. 25(c)) irrespective of stringency conditions utilized. It is possible that the gene may exist in more species more closely related to soybean.

SC21

Figure 11A:
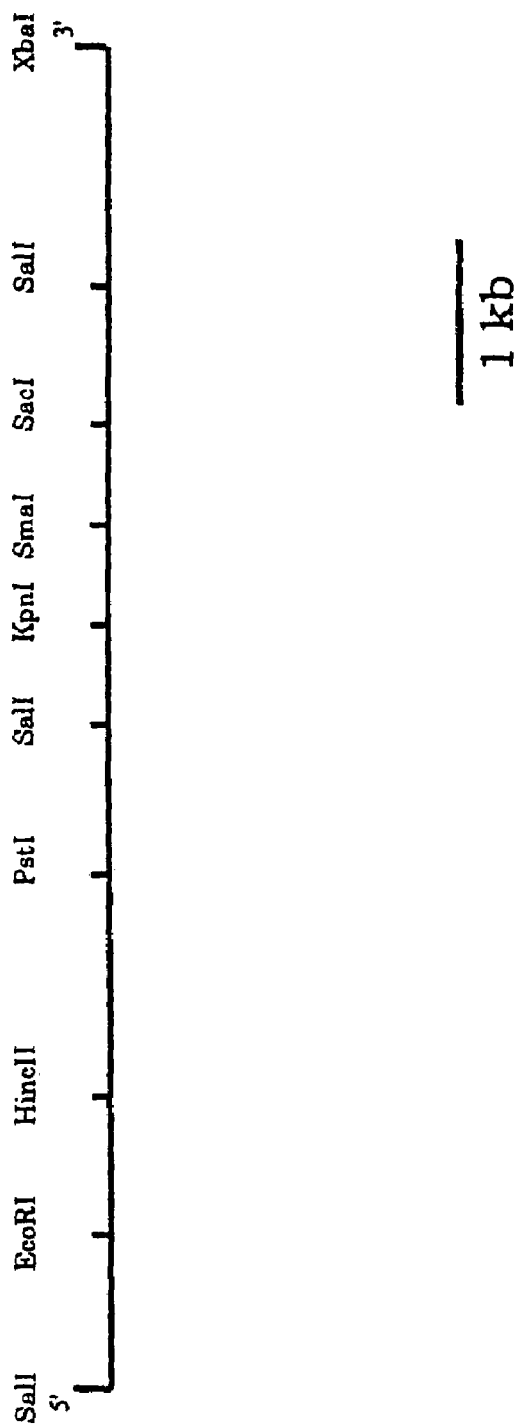
FIG. 11 shows the restriction maps obtained from FIG. 11(*a*) SC20.
Figure 11B:
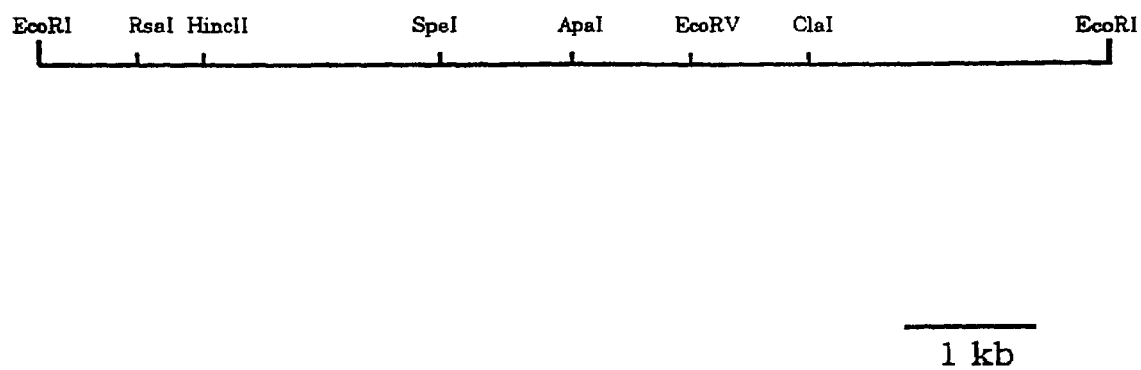
Figure 13C:
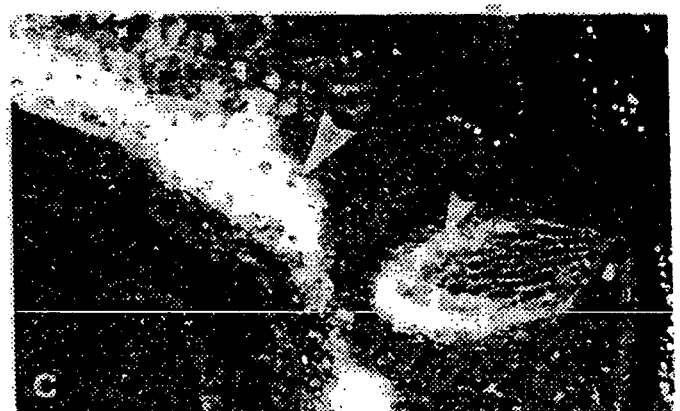

The expression of a gene under the control of SC21 promoter (see FIG. 11(b)) within seed coat tissues at 15 days after anthesis is shown in FIG. 13(c). Note specific localization of the probe in the thin-walled parenchyma of the outer integument, including the area immediately surrounding the tracheid bar (arrow).

The nucleotide sequences of SC21 (SEQ ID NO:5) and SC17 were identical apart from the position of the poly (A) tail and were just less than 65% similar to a *Cicer arientinum* (chickpea) mRNA for an unknown protein.

The expression of genes under the control of seed-coat promoters of this invention are shown in FIGS. 10, 13, 14, 21 and 24.

The results of these and other experiments indicating the expression patterns of these genes is summarized in Table 4 within the Examples section.

The promoters of the present invention can be used to control the expression of any given gene spatially and developmentally within developing seed coats, or seed-coat associated tissues. Some examples of such uses, which are not to be considered limiting, include:

1. Modification of storage reserve yields in seed coats, such as starch by the expression of yeast invertase to mobilize the starch, or increasing starch levels by increasing the sink strength by enhancing carbon unloading into seeds, by expressing invertase in specific seed coat tissues, or reduce starch levels by inhibit starch biosynthesis through the expression of the antisense transcript of ADP-glucose pyrophosphorylase.
2. Modification of seed colour contributed by anthocyanin pigments or condensed tannins in the seed coats by expression of antisense transcripts of the phenylalanine ammonia lyase or chalcone synthase genes.
3. Modification of fibre content in seed-derived meal by expression of antisense transcripts of the caffeic acid-o-methyl transferase or cinnamoyl alcohol dehydrogenase genes.
4. Inhibition of seed coat maturation by expression of ribonuclease genes to allow for increased seed size, and to reduce the relative biomass of seed coats, and to aid in dehulling of seeds.
5. Expression of genes in seed coats coding for insecticidal proteins such as α-amylase inhibitor or protease inhibitor.
6. Partitioning of seed metabolites such as glucosinolates into seed coats for fungal or insect resistance.
7. Production of high value proteins in seed coats for use as pharmaceuticals or for use in industrial processes.
8. Control of seed borne diseases by expressing antifungal antiviral, or anti-bacterial proteins within the seed coat Furthermore, modifications of the nucleotide, or amino acid, sequence of HP, or the preparation of chimeric gene constructs comprising the regulatory region of HP associated with a gene of interest will result in:

alterations in the textural, visual, chemical or other properties of the seed coat, including the seed surface;
 the production of plants that are less susceptible to seed borne and pod diseases by expressing heterologous proteins in tissues of the ovary wall;
 lessening the health hazard of seed dust exposure by genetic selection or transformation, to produce plants with reduced allergenic protein expression on the seed surface Thus this invention is directed to such promoter and gene combinations. Further this invention is directed to such promoter and gene combinations in a cloning vector, wherein the gene is under the control of a seed coat specific promoter and is capable of being expressed in a plant cell transformed with the vector. This invention further relates to transformed plant cells and transgenic plants regenerated from such plant cells. The promoter and promoter gene combination of the present invention can be used to transform any plant cell for the production of any transgenic plant. The present invention is not limited to any plant species.

The following list summarises the nucleotide sequence data in the SEQUENCE LISTING of the present application:
pT218 genomic DNA sequence is found in SEQ ID NO:1;
Ep genomic DNA sequence is listed in SEQ ID NO:2;
SC4 cDNA sequence is presented in SEQ ID NO:3;
SC20 cDNA sequence is in SEQ ID NO:4;
SC21 cDNA sequence is presented in SEQ ID NO:5;
HP cDNA is listed in SEQ ID NO:6;
HP genomic DNA sequence is found in SEQ ID NO:7;
SC20 genomic DNA sequence is listed in SEQ ID NO:8; and
SC4 genomic DNA sequence is presented in SEQ ID NO:9.

While this invention is described in detail with particular reference to preferred embodiments thereof, said embodiments are offered to illustrate but not limit the invention.

EXAMPLES

Characterization of a Seed Coat-Specific GUS Fusion

Transfer of binary constructs to *Agrobacterium* and leaf disc transformation of *Nicotiana tabacum* SR1 were performed as described by Fobert et al. (1991, *Plant Mol. Biol.* 17, 837-851). Plant tissue was maintained on 100 µg/ml kanamycin sulfate (Sigma) throughout in vitro culture.

Nine-hundred and forty transgenic plants were produced. Several hundred independent transformants were screened for GUS activity in developing seeds using the fluorogenic assay. One of these, T218, was chosen for detailed study because of its unique pattern of GUS expression.

Fluorogenic and histological GUS assays were performed according to Jefferson (*Plant Mol. Biol. Rep.*, 1987, 5, 387405), as modified by Fobert et al. (*Plant Mol. Biol.*, 1991, 17, 837-851). For initial screening, leaves were harvested from in vitro grown plantlets. Later flowers corresponding to developmental stages 4 and 5 of Koltunow et al. (*Plant Cell*, 1990, 2, 1201-1224) and beige seeds, approximately 12-16 dpa (Chen et al., 1988, *EMBO J.* 7, 297-302), were collected from plants grown in the greenhouse. For detailed, quantitative analysis of GUS activity, leaf, stem and root tissues were collected from kanamycin resistant F1 progeny of the different transgenic lines grown in vitro. Floral tissues were harvested at developmental stages 8-10 (Koltunow et al., 1990, *Plant Cell* 2, 1201-1224) from the original transgenic plants. Flowers of these plants were also tagged and developing seeds were collected from capsules at 10 and 20 dpa. In all cases, tissue was weighed, immediately frozen in liquid nitrogen, and stored at –80° C.

Tissues analyzed by histological assay were at the same developmental stages as those listed above. Different hand-cut sections were analyzed for each organ. For each plant, histological assays were performed on at least two different occasions to ensure reproducibility. Except for floral organs, all tissues were assayed in phosphate buffer according to Jefferson (1987, *Plant Mol. Biol. Rep.* 5, 387405), with 1 mM X-Gluc (Sigma) as substrate. Flowers were assayed in the same buffer containing 20% (v/v) methanol (Kosugi et al., 1990, *Plant Sci.* 70, 133-140).

Figure 1:
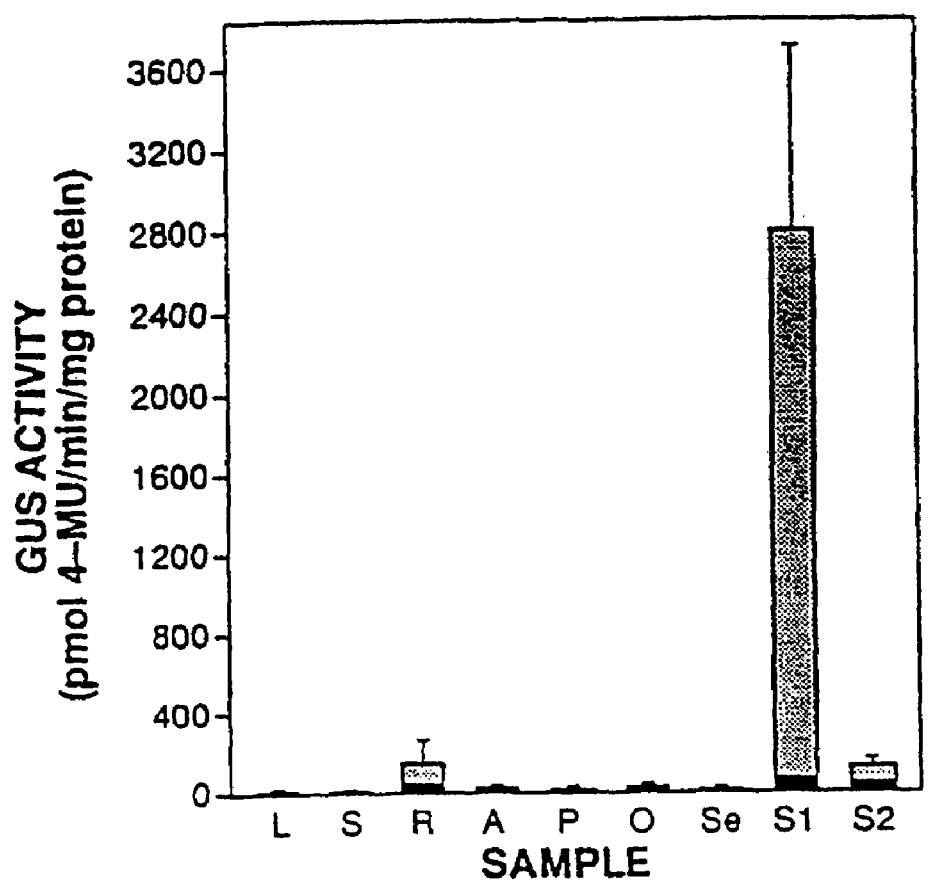
FIG. 1 depicts the fluorogenic analyses of GUS expression in the plant T218. Each bar represents the average±one standard deviation of three samples. Nine different tissues were analyzed: leaf (L), stem (S), root (R), anther (A), petal (P), ovary (O), sepal (Se), seeds 10 days post anthesis (S1) and seeds 20 days post-anthesis (S2). For all measurements of GUS activity, the fraction attributed to intrinsic fluorescence, as determined by analysis of untransformed tissues, is shaded black on the graph. Absence of a black area at the bottom of a histogram indicates that the relative contribution of the background fluorescence is too small to be apparent.

Tissue-specific patterns of GUS expression were only found in seeds. For instance, GUS activity in plant. T218 (FIG. 1) was localized in seeds from 9 to 17 days postanthesis (dpa). GUS activity was not detected in seeds at other stages of development or in any other tissue analyzed which included leaf, stem, root, anther, ovary, petal and sepal (FIG. 1). Histological staining with X-Gluc revealed that GUS expression in seeds at 14 dpa was localized in seed coats but was absent from the embryo, endosperm, vegetative organs and floral organs. (results not shown).

The seed coat-specificity of GUS expression was confirmed with the more sensitive fluorogenic assay of seeds derived from reciprocal crosses with untransformed plants. The seed coat differentiates from maternal tissues called the integuments which do not participate in double fertilization (Esau, 1977, *Anatomy of Seed Plants*. New York: John Wiley and Sons). If GUS activity is strictly regulated, it must originate from GUS fusions transmitted to seeds maternally and not by pollen. As shown in Table 3, this is indeed the case. As a control, GUS fusions expressed in embryo and endosperm, which are the products of double fertilization, should be transmitted through both gametes. This is illustrated in Table 3 for GUS expression driven by the napin promoter (Bng-NAPI, Baszczynki and Fallis, 1990, *Plant Mol. Biol.* 14, 633-635) which is active in both embryo and endosperm (data not shown).

TABLE 3

| GUS activity in seeds at 14 days post anthesis. | | |
|---|---|---|
| Cross | | GUS Activity |
| ♀ | ♂ | nmole MU/min/mg Protein |
| T218 | T218 | 1.09 ± 0.39 |
| T218 | WT[a] | 3.02 ± 0.19 |
| WT | T218 | 0.04 ± 0.005 |
| WT | WT | 0.04 ± 0.005 |
| NAP-5[b] | NAP-5 | 14.6 ± 7.9 |
| NAP-5 | WT | 3.42 ± 1.60 |
| WT | NAP-5 | 2.91 ± 1.97 |

[a]WT, untransformed plants
[b]Transgenic tobacco plants with the GUS gene fused to the napin, Bng-NAP1, promoter (Baszczynski and Fallis, 1990, Plant Mol. Biol. 14, 633–635).

Cloning and Analysis of the Seed Coat-Specific GUS Fusion

Genomic DNA was isolated from freeze-dried leaves using the protocol of Sanders et al. (1987, *Nucleic Acid Res.* 15, 1543-1558). Ten micrograms of T218 DNA was digested for several hours with EcoRI using the appropriate manufacturer-supplied buffer supplemented with 2.5 mM spermidine. After electrophoresis through a 0.8% TAE agarose gel, the DNA size fraction around 4-6 kb was isolated, purified using the GeneClean kit (BIO 101 Inc., LaJolla, Calif.), ligated to phosphatase-treated EcoRI-digested Lambda GEM-2 arms (Promega) and packaged in vitro as suggested by the supplier. Approximately 125,000 plaques were transferred to nylon filters (Nytran, Schleicher and Schuell) and screened by plaque hybridization (Rutledge et al., 1991, *Mol. Gen. Genet.* 229, 31-40), using the 3' (termination signal) of the nos gene as probe (probe #1, FIG. 2). This sequence, contained in a 260 bp SstI/EcoRI restriction fragment from pPRF-101 (Fobert et al., 1991, *Plant Mol. Biol.* 17, 837-851), was labelled with [α-$^{32}$P]-dCTP (NEN) using random priming (Stratagene). After plaque purification, phage DNA was isolated (Sambrook et al., 1989, A Laboratory Manual. New York: Cold Spring Harbor Laboratory Press), mapped and subcloned into pGEM-4Z (Promega). The EcoRI fragment and deletions shown in FIG. 2 were inserted into pBIN19 (Bevan, 1984, *Nucl. Acid Res.* 12, 8711-8721). Restriction mapping was used to determine the orientation of the fusion in pBIN19 and to confirm plasmid integrity. Plants were transformed with a derivative which contained the 5' end of the GUS gene distal to the left border repeat. This orientation is the same as that of the GUS gene in the binary vector pB1101 (Jefferson, 1987, *Plant Mol. Biol. Rep.* 5, 387-405).

Figure 2:
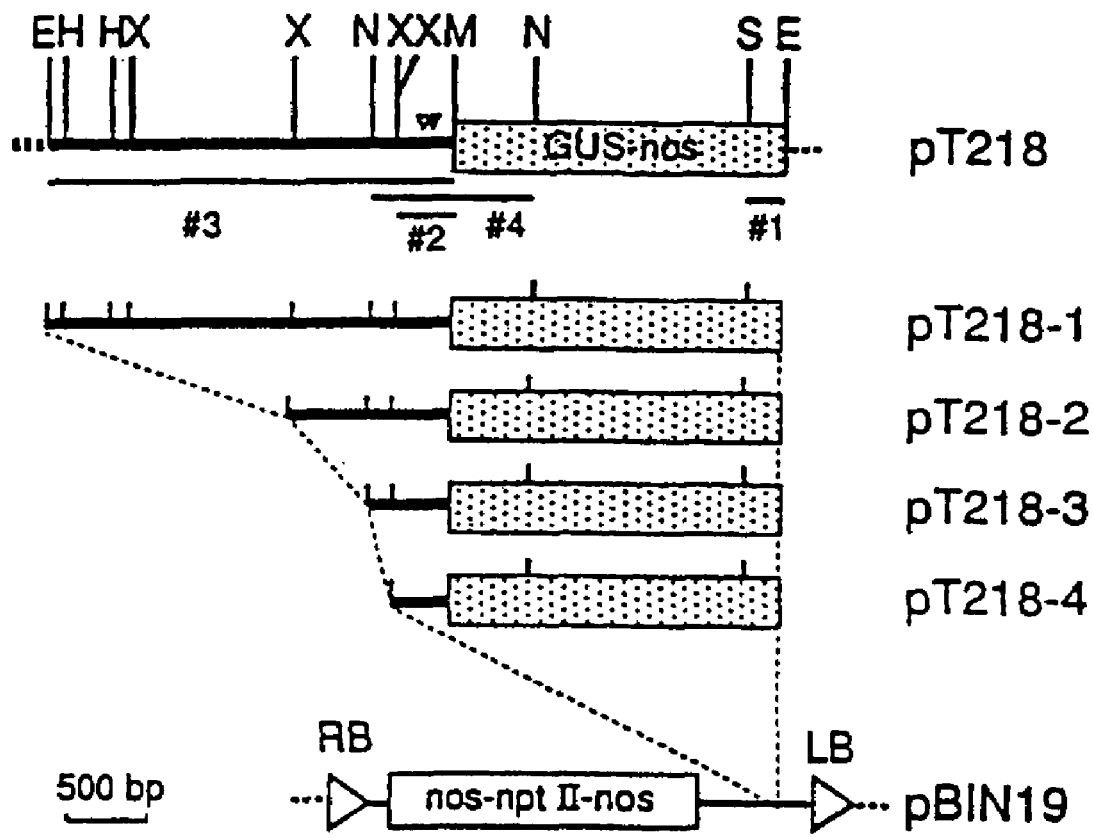
FIG. 2 shows the cloning of the GUS fusion in plant T218 (pT218) and construction of transformation vectors. Plant DNA is indicated by the solid line and the promoterless GUS-nos gene is indicated by the open box. The transcriptional start site and presumptive TATA box are located by the closed and open arrow heads respectively. DNA probes #1, 2, 3 and RNA probe #4 are shown. The EcoRI fragment in pT218 was subcloned in the pBIN19 polylinker to create pT218-1. Fragments truncated at the XbaI SnaBI and XbaI sites were also subcloned to create pT218-2, pT218-3 and pT2184. Abbreviations for the endonuclease restriction sites are as follows: EcoRI (E), HindIII (H), XbaI (X), SnaBI (N), SmaI (M), SstI (S).

The GUS fusion in plant T218 was isolated as a 4.7 kb EcoRI fragment containing the 2.2 kb promoterless GUS-nos gene at the T-DNA border of pPRF120 and 2.5 kb of 5' flanking tobacco DNA (pT218, FIG. 2), using the nos 3' fragment as probe (probe #1, FIG. 2). To confirm the ability of the flanking DNA to activate the GUS coding region, the entire 4.7 kb fragment was inserted into the binary transformation vector pBIN19 (Bevan, 1984, *Nucl. Acid Res.* 12, 8711-8721), as shown in FIG. 2. Several transgenic plants were produced by *Agrobacterium*-mediated transformation of leaf discs. Southern blots indicated that each plant contained 1-4 T-DNA insertions at unique sites. The spatial patterns of GUS activity were identical to that of plant T218. Histologically, GUS staining was restricted to the seed coats of 14 dpa seeds and was absent in embryos and 20 dpa seeds (results not shown). Fluorogenic assays of GUS activity in developing seeds showed that expression was restricted to seeds between 10 and 17 dpa, reaching a maximum at 12 dpa (FIGS. 3(*a*) and 3(*b*)). The 4.7 kb fragment therefore contained all of the elements required for the tissue-specific and developmental regulation of GUS expression.

Figures 3A, 3B:
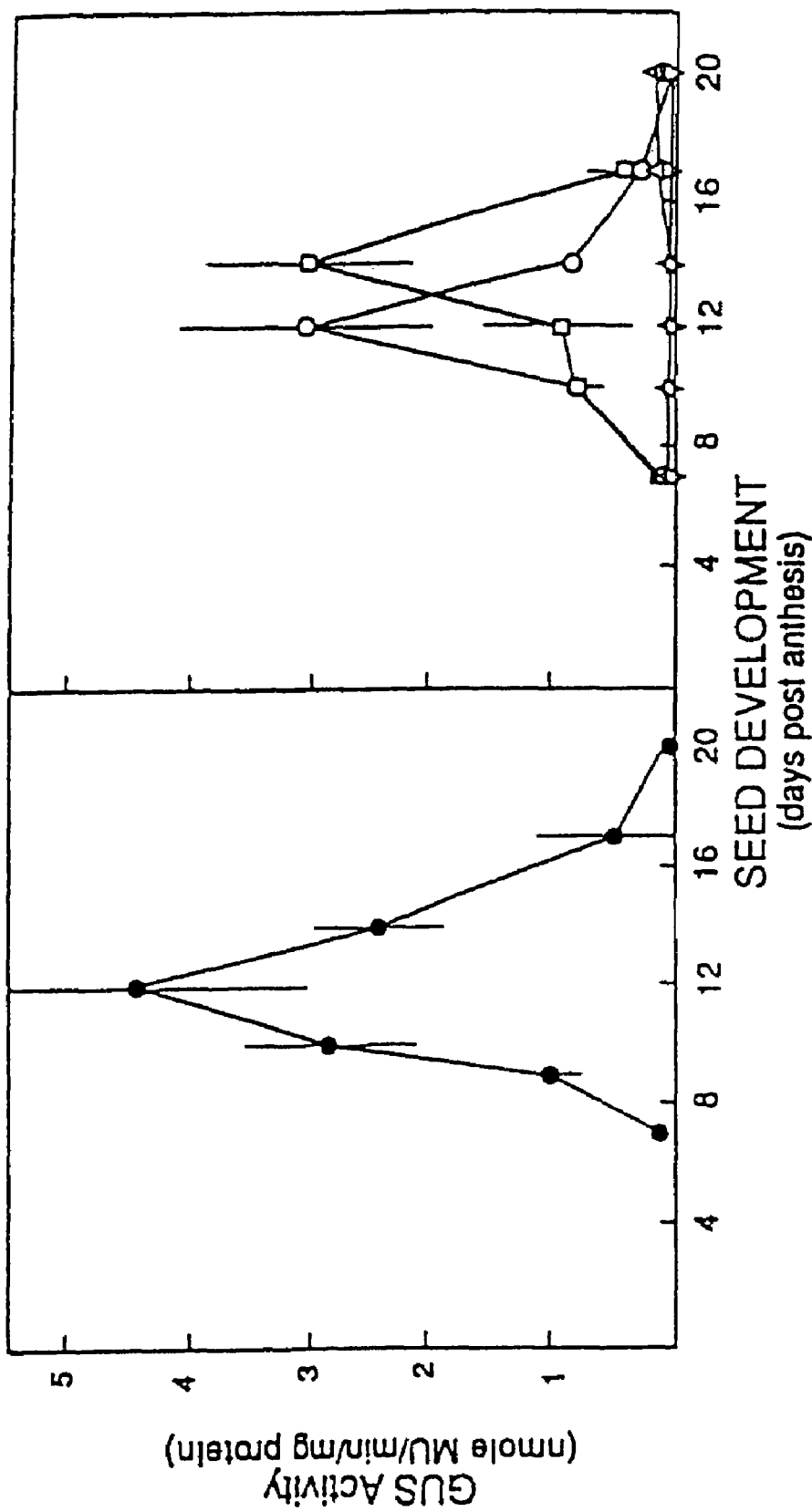
(FIG. 3b) plants transformed with vectors pT218-1 (○-○), pT218-2 (□-□), pT218-3 (∇-∇) and pT2184 (Δ-Δ) which are illustrated in FIG. 2. The 2 day delay in the peak of GUS activity during seed development, seen with the pT218-2 transformant, likely reflects greenhouse variation conditions.
Figure 4:
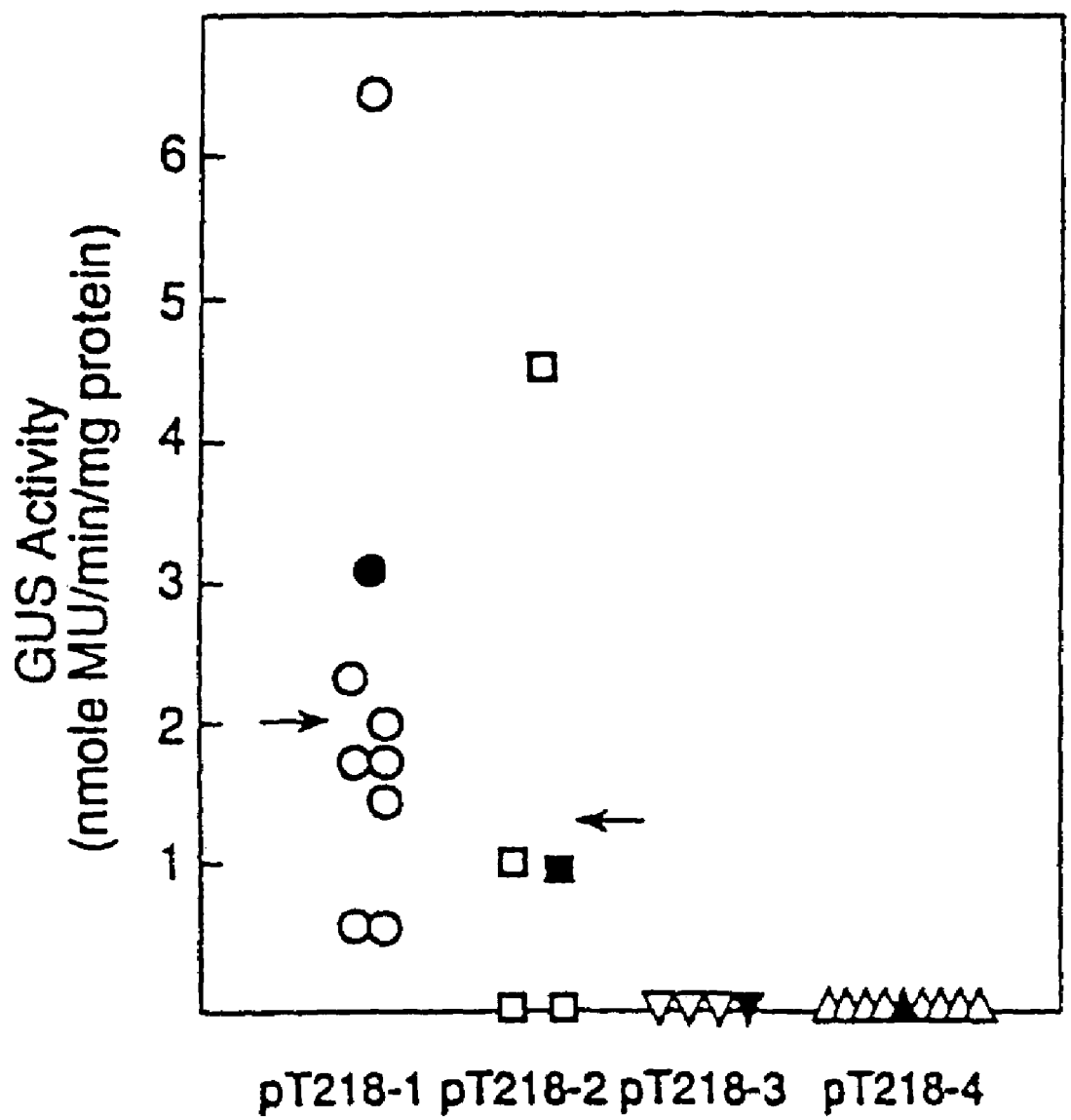
FIG. 4 shows GUS activity in 12 dpa seeds of independent transformants produced with vectors pT218-1 (○), pT218-2 (□), pT218-3 (∇) and pT2184 (Δ). The solid markers indicate the plants shown in FIG. 3 (b) and the arrows indicate the average values for plants transformed with pT218-1 or pT218-2.

To locate regions within the flanking plant DNA responsible for seed coat-specificity, truncated derivatives of the GUS fusion were generated (FIG. 2) and introduced into tobacco plants. Deletion of the region approximately between 2.5 and 1.0 kb, 5' of the insertion site (pT218-2, FIG. 2) did not alter expression compared with the entire 4.7 kb GUS fusion (FIGS. 3*b* and 4). Further deletion of the DNA, to the SnaBI restriction site approximately 0.5 kb, 5' of the insertion site (pT218-3, FIG. 2), resulted in the complete loss of GUS activity in developing seeds (FIGS. 3*b* and 4). This suggests that the region approximately between 1.0 and 0.5 kb, 5' of the insertion site contains elements essential to gene activation. GUS activity in seeds remained absent with more extensive deletion of plant DNA (pT218-4, FIGS. 2, 3*b* and 4) and was not found in other organs including leaf, stem, root, anther, petal, ovary or sepal from plants transformed with any of the vectors (data not shown).

Figure 5A:
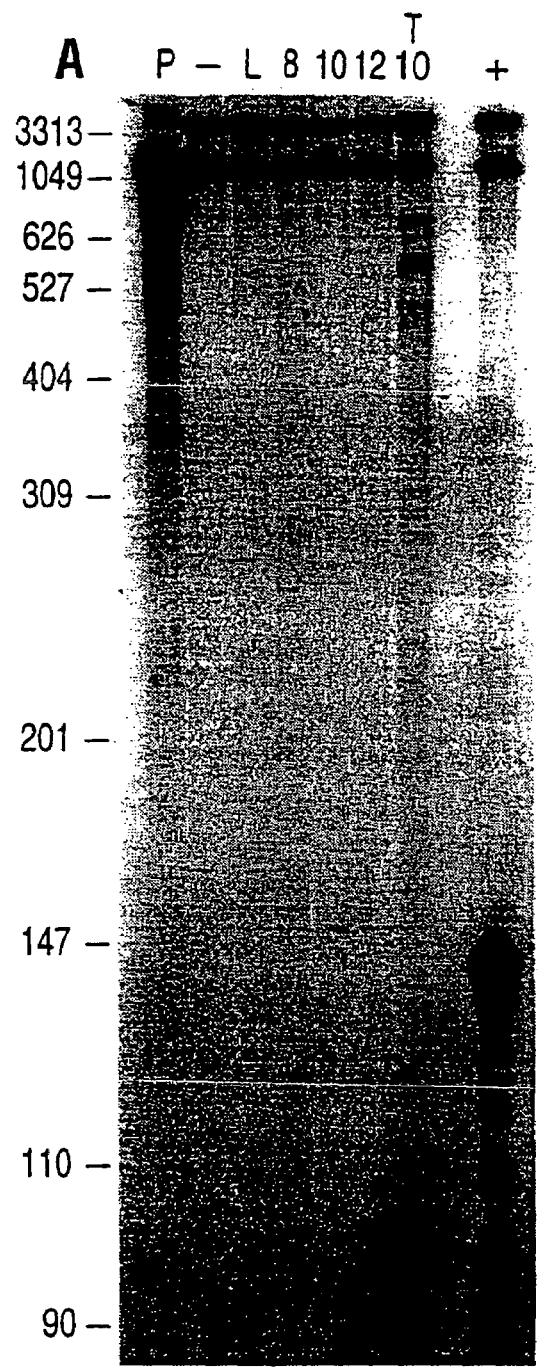
FIG. 5(a) shows the mapping of the GUS mRNA termini in plant T218. The antisense RNA probe from subclone #4 (FIG. 2) was used for hybridization with total RNA of tissues from untransformed plants (10 µg) and from plant T218 (30 µg). Arrowheads indicate the anticipated position of protected fragments if transcripts were initiated at the same sites as the T218 GUS fusion.
Figure 5B:
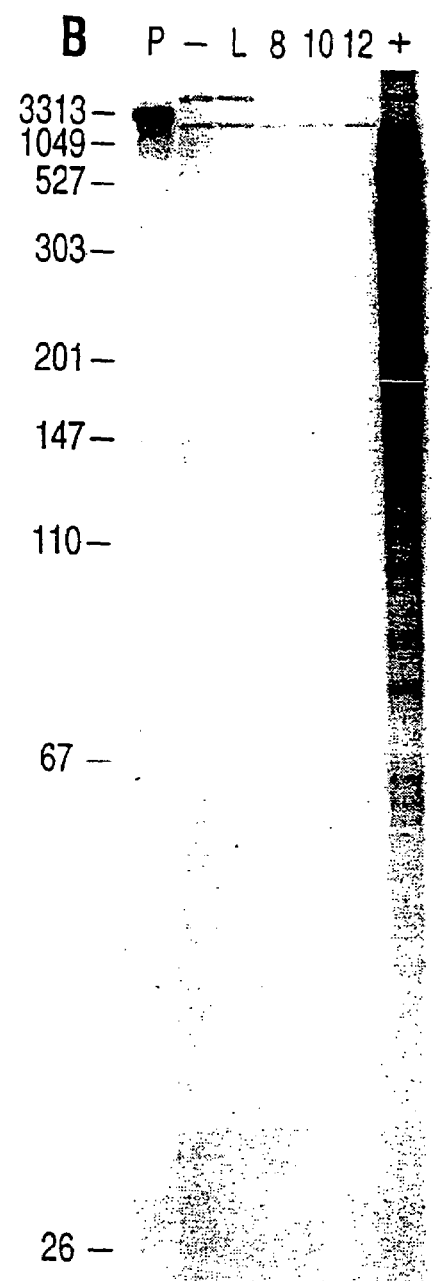
FIG. 5(b) shows the, RNase protection assay using the antisense (relative to the orientation of the GUS coding region) RNA probe from subclone e (FIG. 7) against 30 µg total RNA of tissues from untransformed plants. P, untreated RNA probe; –, control assay using the probe and tRNA only; L, leaves from untransformed plants; 8, 10, 12, seeds from untransformed plants at 8, 10, and 12 dpa, respectively; T10, seeds of plant T218 at 10 dpa; +, control hybridization against unlabelled in vitro-synthesized sense RNA from subclone c (panel a) or subclone e (panel b). The two hybridizing bands near the top of the gel are end-labelled DNA fragment of 3313 and 1049 bp, included in all assays to monitor losses during processing. Molecular weight markers are in number of bases.
Figure 7:
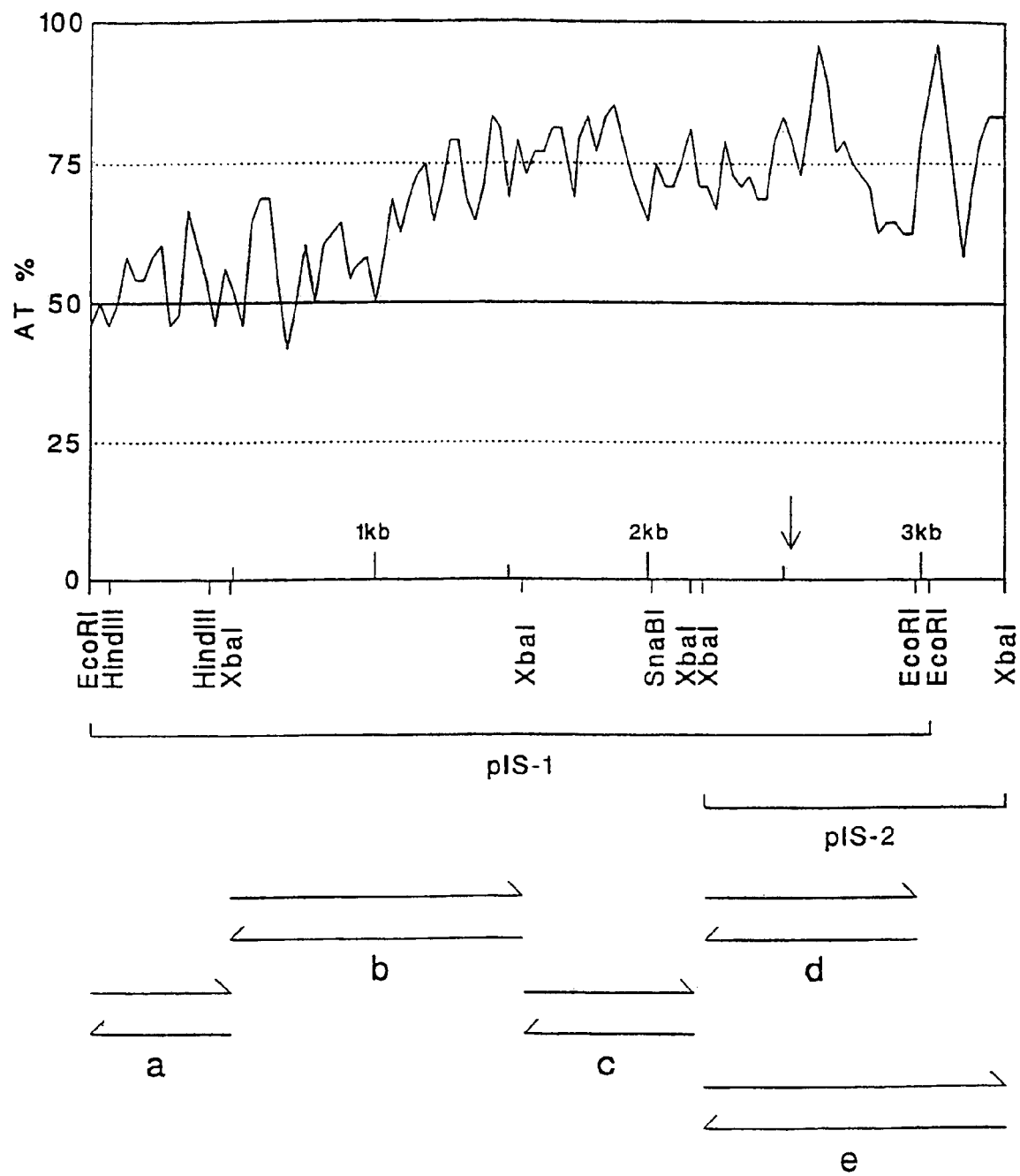
FIG. 7 shows the base composition of region surrounding the T218 insertion site cloned from untransformed plants. The site of T-DNA insertion in plant T218 is indicated by the vertical arrow. The position of the 2 genomic clones pIS-1 and pIS-2, and of the various RNA probes (a-e) used in RNase protection assays are indicated beneath the graph.

The transcriptional start site for the GUS gene in plant T218 was determined by RNase protection assays with RNA probe #4 (FIG. 2) which spans the T-DNA/plant DNA junction. For RNase protection assays, various restriction fragments from pIS-1, pIS-2 and pT218 were subcloned into the transcription vector pGEM4Z as shown in FIGS. 7 and 2, respectively. A 440 bp HindIII fragment of the tobacco acetohydroxyacid synthase SURA gene was used to detect SURA and SURB mRNA. DNA templates were linearized and transcribed in vitro with either T7 or SP6 polymerases to generate strand-specific RNA probes using the Promega transcription kit and [$\alpha$-$^{32}$P]CTP as labelled nucleotide. RNA probes were further processed as described in Ouellet et al. (1992, *Plant J.* 2, 321-330). RNase protection assays were performed as described in Ouellet et al., (1992, *Plant J.* 2, 321-330), using 10-30 µg of total RNA per assay. Probe digestion was done at 30° C. for 15 min using 30 µg ml$^{-1}$ RNase A (Boehringer Mannheim) and 100 units ml$^{-1}$ RNase T1 (Boehringer Mannheim). FIG. 5 shows that two termini were mapped in the plant DNA. The major 5' terminus is situated at an adenine residue, 122 bp upstream of the T-DNA insertion site (FIG. 6). The sequence at this transcriptional start site is similar to the consensus sequence for plant genes (C/TTC↓ATCA; Joshi, 1987 *Nucleic Acids Res.* 15, 6643-6653). A TATA box consensus sequence is present 37 bp upstream of this start site (FIG. 6). The second, minor terminus mapped 254 bp from the insertion site in an area where no obvious consensus motifs could be identified (FIG. 6).

The tobacco DNA upstream of the insertion site is very AT-rich (>75%, see FIG. 7). A search for promoter-like motifs and scaffold attachment regions (SAR), which are often associated with promoters (Breyne et al., 1992, *Plant Cell* 4, 463-471; Gasser and Laemmli, 1986, *Cell* 46, 521-530), identified several putative regulatory elements in the first 1.0 kb of tobacco DNA flanking the promoterless GUS gene (data not shown). However, the functional significance of these sequences remains to be determined.

Cloning and Analysis of the Insertion Site from Untransformed Plants

A lambda DASH genomic library was prepared from DNA of untransformed *N. tabacum* SR1 plants by Stratagene for cloning of the insertion site corresponding to the gene fusion in plant T218. The screening of 500,000 plaques with probe #2 (FIG. 2) yielded a single lambda clone. The EcoRI and XbaI fragments were subcloned in pGEM4Z to generate pIS-1 and pIS-2. FIG. 7 shows these two overlapping subclones, pIS-1 (3.0 kb) and pIS-2 (1.1 kb), which contain tobacco DNA spanning the insertion site (marked with a vertical arrow). DNA sequence analysis (using dideoxy nucleotides in both directions) revealed that the clones, pT218 and pIS-1, were identical over a length of more than 2.5 kb, from the insertion site to their 5' ends, except for a 12 bp filler DNA insert of unknown origin at the T-DNA border (FIG. 6 and data not shown). The presence of filler DNA is a common feature of T-DNA/plant DNA junctions (Gheysen et al., 1991, *Gene* 94, 155-163). Gross rearrangements that sometimes accompany T-DNA insertions (Gheysen et al., 1990, *Gene* 94, 155-163; and 1991, *Genes Dev.* 5, 287-297) were not found (FIG. 6) and therefore could not account for the promoter activity associated with this region. The region of pIS-1 and pIS-2,3' of the insertion site is also very AT-rich (FIG. 7).

To determine whether there was a gene associated with the pT218 promoter, more than 3.3 kb of sequence contained with pIS-1 and pIS-2 was analyzed for the presence of long open reading frames (ORFs). However, none were detected in this region (data not shown). To determine whether the region surrounding the insertion site was transcribed in untransformed plants, Northern blots were performed with RNA from leaf, stem, root, flower and seeds at 4, 8, 12, 14, 16, 20 and 24 dpa. Total RNA from leaves was isolated as described in Ouellet et al., (1992, *Plant J.* 2, 321-330). To isolate total RNA from developing seeds, 0.5 g of frozen tissue was pulverized by grinding with dry ice using a mortar and pestle. The powder was homogenized in a 50 ml conical tube containing 5 ml of buffer (1 M Tris HCl, pH 9.0, 1% SDS) using a Polytron homogenizer. After two extractions with equal volumes of phenol:chloroform:isoamyl alcohol (25:24:1), nucleic acids were collected by ethanol precipitation and resuspended in water. The RNA was precipitated overnight in 2M LiCl at 0° C., collected by centrifugation, washed in 70% ethanol and resuspended in water. Northern blot hybridization was performed as described in Gottlob-McHugh et al. (1992, *Plant Physiol.* 100, 820-825). Probe #3 (FIG. 2) which spans the entire region of pT218 5' of the insertion did not detect hybridizing RNA bands (data not shown). To extend the sensitivity of RNA detection and to include the region 3' of the insertion site within the analysis, RNase protection assays were performed with 10 different RNA probes that spanned both strands of pIS-1 and pIS-2 (FIG. 7). Even after lengthy exposures, protected fragments could not be detected with RNA from 8, 10, 12 dpa seeds or leaves of untransformed plants (see FIG. 5 for examples with two of the probes tested). The specific conditions used allowed the resolution of protected RNA fragments as small as 10 bases (data not shown). Failure to detect protected fragments was not due to problems of RNA quality, as control experiments using the same samples detected acetohydroxyacid synthase (AHLS) SURA and SURB mRNA which are expressed at relatively low abundance (data not shown). Conditions used in the present work were estimated to be sensitive enough to detect low-abundance messages representing 0.001-0.01% of total mRNA levels (Ouellet et al., 1992, Plant J. 2, 321-330). Therefore, the region flanking the site of T-DNA insertion does not appear to be transcribed in untransformed plants.

Genomic Origins of the Insertion Site

Figure 8:
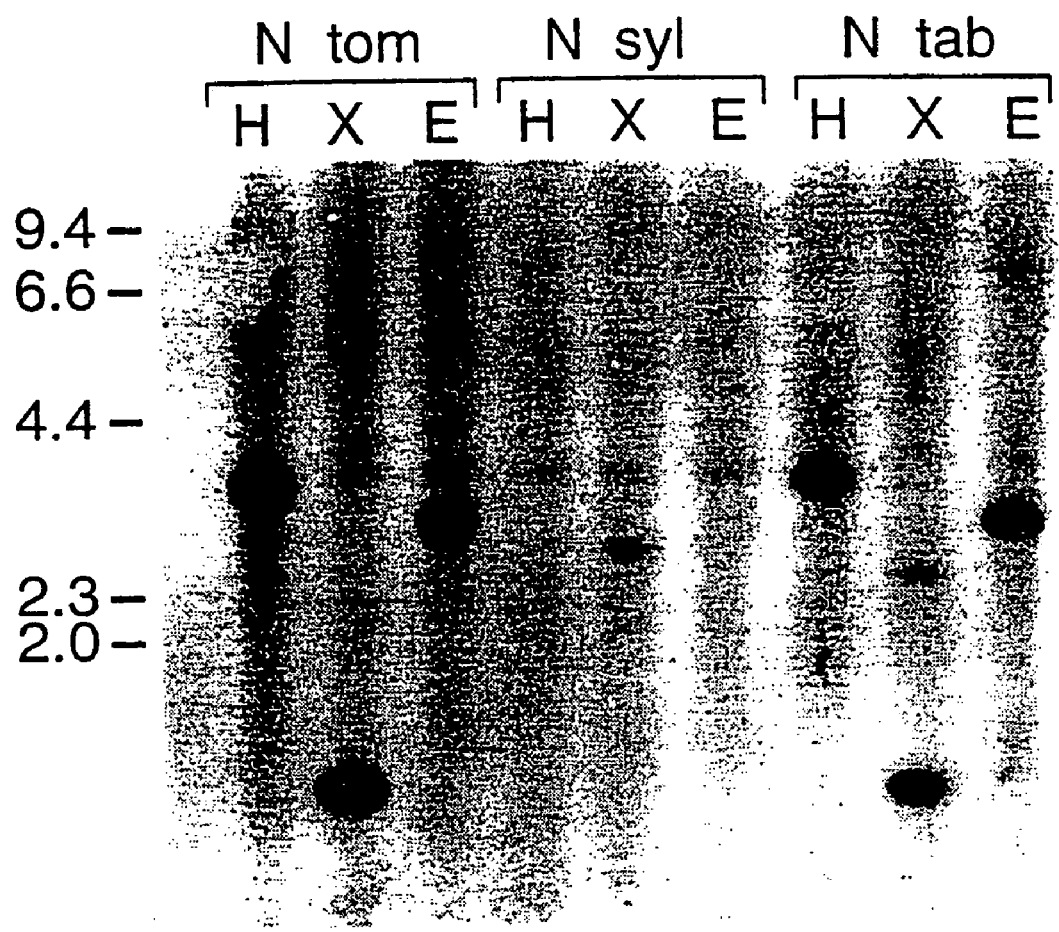
FIG. 8 shows the Southern blot analyses of the insertion site in *Nicotiana* species. DNA from *N. tomentosiformis* (N tom), *N. sylvestris* (N syl), and *N. tabacum* (N tab) were digested with HindIII (H), XbaI (X) and EcoRI (E) and hybridized using probe #2 (FIG. 2). Lambda HindIII markers (kb) are indicated.
Figure 9:
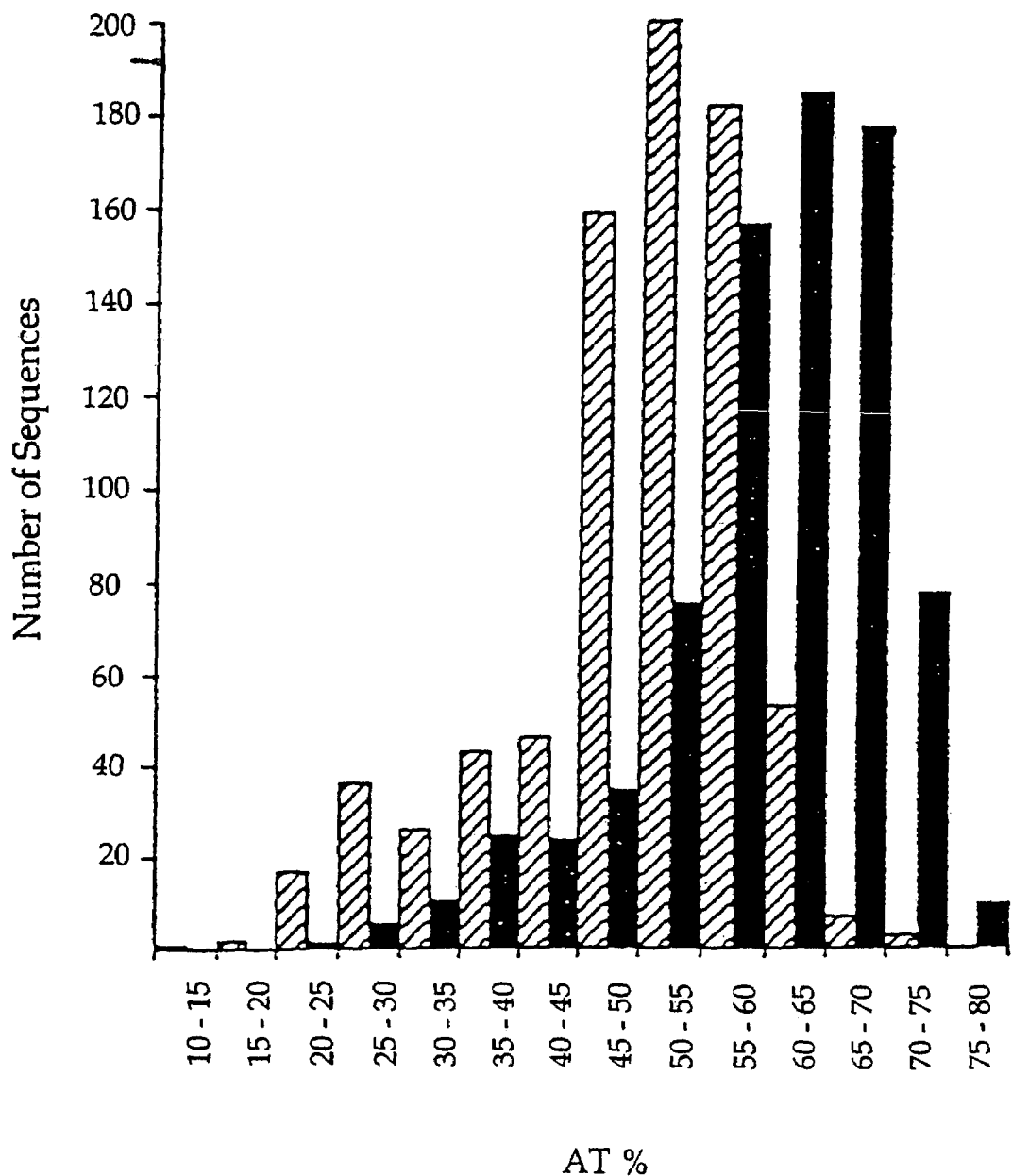
FIG. 9 shows the AT content of 5' non-coding regions of plant genes. A program was written in PASCAL to scan GenBank release 75.0 and to calculate the AT contents of the 5' non-coding (solid bars) and the coding regions (hatched bars) of all plant genes identified as "Magnoliophyta" (flowering plants). The region −200 to −1 and +1 to +200 were compared. Shorter sequences were also accepted if they were at least 190 bp long. The horizontal axis shows the ratio of the AT content (%). The vertical axis shows the number of the sequences having the specified AT content ratios

Southern blots were performed to determine if the insertion site is conserved among Nicotiana species. Genomic DNA (5 μg) was isolated, digested and separated by agarose gel electrophoresis as described above. After capillary transfer on to nylon filters, DNA was hybridized, and probes were labelled, essentially as described in Rutledge et al. (1991, Mol. Gen. Genet. 229, 31-40). High-stringency washes were in 0.2× SSC at 65° C. while low-stringency washes were in 2×SSC at room temperature. In FIG. 8, DNA of the allotetraploid species N. tabacum and the presumptive progenitor diploid species N. tomentosiformis and N. sylvestris (Okamuro and Goldberg, 1985, Mol. Gen. Genet., 198, 290-298) were hybridized with probe #2 (FIG. 2). Single hybridizing fragments of identical size were detected in N. tabacum and N. tomentosiformis DNA digested with HindIII, XbaI and EcoRI, but not in N. sylvestris. Hybridizations with pIS-2 (FIG. 8) which spans the same region but includes DNA 3' of the insertion site yielded the same results. They did not reveal hybridizing bands, even under conditions of reduced stringency, in additional Nicotiana species including N. rustica, N. glutinosa, N. megalosiphon and N. debneyi (data not shown). Probe #3 (FIG. 2) revealed the presence of moderately repetitive DNA specific to the N. tomentosiformis genome (data not shown). These results suggest that the region flanking the insertion site is unique to the N. tomentosiformis genome and is not conserved among related species as might be expected for regions that encode essential genes.

Cloning of Seed-coat Genes from Soybean:

a) Isolation of Seed-coat cDNA Clones

A seed coat cDNA library was constructed in Lambda GEM4 from poly(A)+ mRNA isolated from soybean [Glycine max (L.) Merrill] seed coats. A sample of the total amplified library was used to sub-clone inserts from the original lambda vector into PBK-CMV (Stratagene). Random clones were selected from this mass excision for plasmid purification and single-run DNA sequencing to construct an expressed sequence tag (EST) database.

For differential screening, an additional cDNA library was constructed from cultivar Maple Presto (EpEp) seed coats. The seed coats were harvested from seeds of four fresh weight groups: <50 mg, 50-100 mg, 150-250 mg and >250 mg, to represent all developmental stages. Total RNA was isolated from the seed coats using Trizole reagent (BRL) from which poly (A)+ RNA was isolated using Oligotex resin (Qiagen). First and second strand cDNAs were synthesized using the Riboclone cDNA synthesis kit and then cloned into a lambda GEM-4 vector (Promega). This seed coat library was differentially screened with positive and negative cDNA probes to identify genes preferentially expressed in the seed coat. The positive probe was derived from poly (A)+ mRNA isolated from seed coat tissues while the negative probe was made from poly (A)+ mRNA from seedling, flower bud, leaf, pod and root tissue. The cDNA library was screened with cDNA synthesized from RNA using oligo(dT)$_{15}$ primer, and hybridizations were carried out in Denhardt's solution (Sambrook et al. (1989) Molecular Cloning, Second Edition) at 65° C.; wash 4×30 minutes 0.1×SSC 0.1% SDS at 65° C.

Twenty-one positive clones were identified after plaque purification. The Lambda vector GEM-4 contains a complete pGEM1 plasmid. During the cloning procedure the cDNA is inserted into the Lambda vector at the multicloning site of this plasmid. The entire pGEM1 plasmid, containing the cDNA insert, can be removed from the Lambda vector by digestion with Spe1 and then can be relegated to form a functional plasmid. Except for SC11 and SC19, the insert was removed from pGEM1 by digestion with Xba1 and EcoR1 and ligated into an alternative plasmid vector pGEM4-Z. Following this protocol 21 seed coat clones were used to transform E. coli DH5α. No transformants were obtained with seed coat clones SC7 and SC10 and so these clones were not processed further.

Seed surface proteins were obtained from soybean. A single seed was placed in a 2 mL plastic capped test tube and surface proteins were extracted by adding 0.5 mL of a buffer-detergent solution containing 10 mM Tris-Cl (pH 7.5) 0.5% SDS, and 20 mM DTT, and placing the tube in a boiling water bath for 2 min. The contents of the tube were mixed and an aliquot was withdrawn and centrifuged for 5 min at 14,000 g. Freshly prepared loading buffer containing 20 mM DTT was added to the sample and proteins were electrophoretically separated on 15% acrylamide gels in the presence of SDS (see FIG. 17) using a modified Laemmli system, as described by Fling and Gregerson (1986, Anal Biochem 155:83-88). Fixation and visualization of the proteins by silver staining followed the method of Blum et al., (1987 Electrophoresis 8: 93-99). The amino terminal of the major peptides (indicated as HPS in FIG. 17(b)) were micro-sequenced from the blotted proteins according to Moos et al., (1988 J. Biol. Chem 263: 6005-6008). The resulting amino acid sequences were identical and matched existing sequences in the GenBank protein database for HP (Odani et al., 1987 Eur J. Biochem 162, 485-491). Both peptides had alternative N-terminal residues of Ala or Ile, as has been previously noted for HP. The different electrophoretic mobilities of the two peptides could not be accounted for from the microsequencing analysis, but may be due to differences in glycosylation.

Figure 17C:
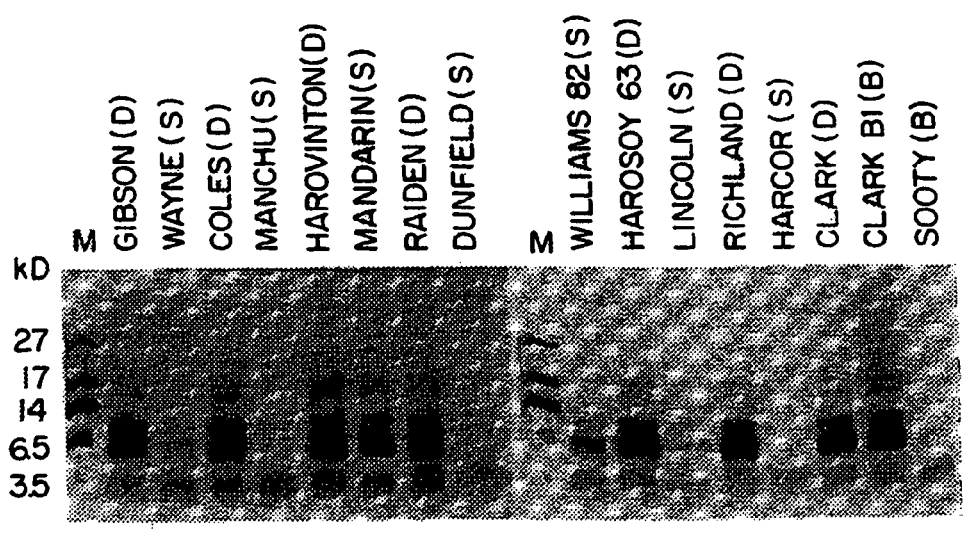

Several different soybean varieties were also compared by SDS-PAGE analysis (see FIG. 17(c)).

To obtain the cDNA transcript of HP, sequences in the seed coat expressed sequence tag database were searched for reading frames corresponding to the HP amino acid sequence. Using this strategy, several identical cDNA transcripts were isolated from the cDNA library obtained from Harosoy 63 seeds described above that included in their reading frames peptide sequences exactly matching HP. The encoded products of these DNA sequences were identified using the BLASTX program at the NCBI site.

b) Characterization of cDNA Clones

Sequence Analysis

Agarose gel electrophoresis of Xba1/EcoR1 digests of the 19 remaining plasmid clones indicated that the inserts ranged in size from approximately 350 bp to 1600 bp, including the poly A tail. Inserts of the seed-coat clones were characterized by double stranded dideoxy sequencing of the 5' and 3' ends of the clones. A preliminary classification of the seed coat cDNA clones was made on the basis of sequence homology in the 3' and 5' ends of the clones. Based on sequence similarity with each other these 19 clones were grouped into 7 groups of clones. Sequence similarity was found between four of these groups and GenBank (with proline rich protein and three peroxidase groups). The three remaining groups had no sequence similarity with GenBank. SC4, SEQ ID NO:3 (found to be the same as SC1), SC20, SEQ ID NO:4 (found to be the same as SC15), and SC21, SEQ ID NO:5, each represent one clone of each of the three groups which did not exhibit similarity with anything in the GenBank database.

SC4

Figure 11D:
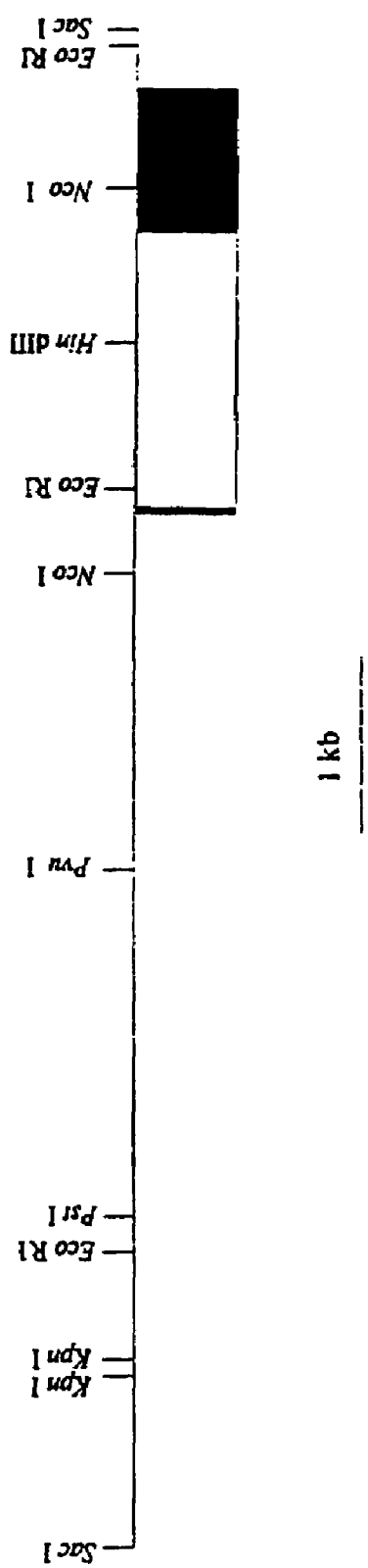

The 1119 bp nucleotide sequence of SC4 (SEQ ID 3, FIG. 19(a); also see Restriction Map FIG. 11(d)) does not represent the full-length cDNA clone as it does not contain an ATG codon for translation initiation. Two typical polyadenylation signals (AATAAA) are located at positions 1096 and 1102. The deduced protein sequence from the SC4 cDNA (FIG. 19(a)) consists of 289 amino acids and has a molecular mass of 31.9 kDa and a predicted pI of 7.95. Three puatative glycosylation sites are present at positions 92, 128 and 269.

The putative polypeptide encoded by SC4 exhibits similarity with proteins that comprises a BURP domain (e.g. RD22, an *Arabidopsis thaliana* dehydration-responsive protein (Yamaguchi-Shinozaki K. and Shinozaki, K. 1993. Mol. Gen. Genet. 238: 17-25); PG1β, a *Lycopersicon esculentum* polygalacturonase isoenzyme 1 β subunit (Zheng L. et al., 1992. Plant Cell. 4: 1147-1156); Sali3-2, a *Glycine max* L aluminium-induced protein (Ragland M. and Soliman, K. M. 1997. Plant Physiol. 114: 395); USP, a Viciafaba unknown seed protein (Baumlein H. et al., 1991. Mol. Gen. Genet. 225: 459-467) and ADR6, a *Glycine max* L auxin-induced protein (Datta N. et al., 1993. Plant Mol. Biol. 21: 859-869); see FIG. 19(b)). The BURP domain is a long carboxyl terminal domain containing a number of highly conserved amino acids (Hattori J. et al., 1998. Mol. Gen. Genet. 259: 424-428). The carboxyl terminal of the conceptual SC4 protein sequence contains the following conserved amino acids which are typical of the BURP domain proteins: two phenylalanine residues, two cysteine residues and four cysteine-histidine motifs which are also in the conserved alignment of CHX10CHX25-27CHX25-26 CH, where X is any amino acid (FIG. 19(b)). This BURP domain proteins also share a similar structural make-up of 3-4 domains (FIG. 19(c)) i.e., an amino-terminal domain containing a hydrophobic sequence, a second domain which may or may not be conserved, a third domain consisting of tandem repeats of a short amino acid sequence (not all BURP domain proteins have this domain) and a long carboxyl-terminal BURP domain (Hattori J. et al., 1998. Mol. Gen. Genet. 259: 424-428). The tandem repeats which make up the third domain do not appear to have a common concensus sequence between the different BURP domain proteins. In addition to the BURP domain, the putative SC4 protein shares sequence similarity between its amino terminus and the conserved segment of the second domain possessed by several of the BURP domain proteins (FIG. 19(b)). It was also determined that the SC4 protein has a region containing two copies of the repeated sequence ESRSIXXYAG where X is any amino acid (FIG. 19(a)) which is similar to the structural organization of the third domain of several BURP domain proteins. Due to the extent of structural and sequence similarity between the SC4 protein and the BURP domain proteins it is likely that SC4 also contains a hydrophobic amino terminal if it was full-length.

SC20

The SC20 cDNA clone was sequenced (FIG. 23 (b)) and found to consist of 2447 bp with one 2310 bp open reading frame starting at nucleotide position 13 and ending at 2322. The TAG stop codon may be leaky as plants have tRNAs capable of misreading it. However, any readthrough will be terminated by a second stop codon TGA which is immediately adjacent to UAG. The 3' untranslated region contains one putative polyadenylation signal (AATAAA) located 21 nt after the stop codon.

The open reading frame of SC20 encodes a putative protein of 770 amino acid residues with a calculated molecular mass of 82.688 kDa and a predicted pI of 6.93. The predicted protein has ten potential N-glycosylation sites (FIG. 23(b)). The hydropathy profile (FIG. 23(c)) of SC20 protein revealed that the first 23 amino acids constitute a hydrophobic region typical of an eukaryotic signal peptide. From northern blot analysis, the SC20 cDNA clone hybridizes to a ~2.5 kb transcript (data not shown). SC20 was used to obtain the genomic clone which was from a soybean cv. Harovinton genomic library.

Sequence comparisons (FIG. 23(d)) revealed that the putative polypeptide encoded by SC20 was similar to a *Picea abies* (black spruce) AF70 protein (Sabala et al., 1997. Physiol. Plant. 99: 316-322); cucumisin, (Yamagata Y. et al. 1994 J. Biol. Chem. 269: 32725-32731) from *Cucumis melo* L. (musk melon); a pathogen-induced protein, P69B, (Tornero P. et al., 1997 J. Biol. Chem. 272: 14412-12219) from *Lycopersicon esculentum* (tomato) and a nodule-specific protein, Agl2, (Ribeiro A. et al., 1995 Plant Cell. 7: 785-794) from *Alnus glutinosa* (black alder). These plant proteins belong to the Pyrolysin family in the clan of serine proteases known as the subtilases (Barrett A. J. and Rawlings N. D., 1995. Arch. Biochem. Biophys. 318:247-250; Siezen, R. J. and Leunissen, J. A. M. 1997. Protein Sci. 6: 501-523.). The SC20 protein contains the conserved catalytic residues aspartate, histidine and serine as well as the highly conserved asparagine residue which is involved in stabilizing substrate binding. Moreover, the order of these four conserved residues in the SC20 protein is also a characteristic feature of subtilases. The SC20 protein also has a large sequence insertion between the conserved asparagine and serine residues found in plant subtilases but not in other subtilase members such as subtilisin BPN' (Power S. D. et al., 1986 PNAS. 83:3096-3100), kex2 (Mizuno K. et al., 1988 Biochem. Biophys. Res. Comm. 156: 246-254) or furin (van de Ven W. J. M. et al., 1990 Mol. Biol. Rep. 14: 265-275). Based on sequence similarity between the N-termini of mature plant subtilases and the SC20 protein (data not shown) it was predicted that the SC20 protein had a mature domain starting from residue 117. Therefore the SC20 protein appears to be composed of 3 domains: a signal peptide of 23 residues followed by a prosequence of 93 residues and a mature domain of 654 residues. The predicted mature domain of SC20 has a calculated molecular weight of 69.918 kDa and an isoelectric point of 6.34.

HP

The cDNA sequence for HP (pHPScDNA1) is (SEQ ID NO:6) shown in FIG. 15. The 700 bp transcript includes 30 bp of 5' untranslated region (UTR), an open reading frame (ORF) of 119 amino acids, and 313 bp of 3' UTR. Several polyadenylation signals were identified in the 3' UTR. The final 80 residues of deduced amino acid sequence exactly match the peptide sequence reported for the hydrophobic protein (Odani et al., 1987, *Eur J Biochem* 162, 485-491).

Thus, the HP cDNA transcript indicates that hydrophobic protein is translated with a leader sequence of 39 amino acids.

Northern Blot Analysis

Northern analysis, using the cDNA inserts of each clone as a probe, was performed to investigate the expression pattern of the 19 seed coat clones.

RNA isolation from leaf, stem, pod and flower tissue was optimized based on a protocol adapted from Tripure Isolation reagent kit (Boehringer Mannheim). Plant tissue was frozen in liquid nitrogen and homogenized with the Tripure reagent (a monophasic solution of phenol and guanidine thiocyanate). After the addition of chloroform the sample is centrifuged so that it separates into three phases. RNA is recovered from the upper aqueous phase by isopropanol precipitation. Due to the problem of polysaccharide contamination which increases with seed maturity, the isopropanol precipitation step was carried out in the presence of high salt which effectively maintains the polysaccharides in a soluble form whilst the RNA is precipitated.

Total RNA from seed-coat, embryo and root tissue was isolated as described by Fobert et al. (Plant J. 1994 6:567-577). Plant tissue was frozen in liquid nitrogen and homogenized in 1M Tris-HCl, pH9, 1% SDS buffer. The sample was extracted twice with equal volume phenol:chloroform:isoamyl alcohol (25:24:1), nucleic acids were collected by ethanol precipitation, collected by ethanol precipitation and resuspended in water. The RNA was precipitated overnight in 2M LiCl at 0° C., collected by centrifugation and resuspended in water.

RNA was denatured and size fractionated by formaldehyde gel electrophoresis and transferred onto nylon filters. Northern hybridization was carried out using radioactively labeled cDNA probes with hybridization in modified Church's buffer (Church and Gilbert (1994) PNAS USA 81: 1991-1995) at 65° C.; wash 2×30 minutes 0.1×SSC 0.1% SDS at 65° C. From this analysis, it was observed that SC4, and SC20 have seed coat specific expression. Ep locus peroxidase has preferential expression within seed-coat tissues, and SC21 was only expressed in seed coat, stem, root and flower tissues. The results are shown in FIGS. 10(*a*)-(*d*).

HP

For the analysis of HP expression, total RNA was isolated from roots, stems, leaves, flowers, pods, seed coats, and embryos dissected from soybean plants at various stages of development, according to published methods (Wang and Vodkin (1994) *Plant Mol Biol Rep* 12, 132-145). The RNA samples were quantitated by measuring absorbence at 260 nm, and by electrophoretic separation in formaldehyde gels and comparison to known standards. Samples of total RNA (10 μg each) were blotted to nylon membrane using a vacuum manifold apparatus and fixed by UV cross-linking. Digoxigenin-labelled cDNA was prepared according to instructions of the manufacturer (Boehringer) and used to probe the RNA blots. Results, FIGS. 10(*e*) and (*f*) show that the HP gene is highly expressed in the pod tissues during the later stages of development. Hybridization signals were also noted in RNA samples derived from seed coat tissue, but not in RNA samples from the leaf, flower, embryo, stem or root. These results, together with the data from the in situ hybridizations (see below) and the scanning electron microscopy analysis, indicate the HP gene is specifically expressed in the endocarp of the ovary wall. Pieces of this tissue detach from the pod wall and adhere to the seed surface during development, thus becoming a component of the mature seed coat (see FIG. 14(*a*).

SC4

RNA samples from seed coat, embryo, stem, root, leaf, pod and flower were hybridized with a radiolabelled SC4 cDNA probe (FIG. 10(*a*)) to determine organ specificity of the expression of SC4. The sc4 transcript was only expressed in the seed coat organ. It was estimated that the size sc4 mRNA was 1.2 kb (data not shown).

Northern blot analysis was carried out to determine the temporal expression pattern of sc4. RNA from seed coat, embryo and pod organs between 6-24 dpa were hybridized with a radiolabelled SC4 cDNA probe. At 6 dpa the seed is too small to separate the seed coat and embryo organs and so total RNA was isolated from an entire seed. sc4 expression was already apparent in the seed by 6 dpa. No gene expression was observed in any of the embryo development stages examined (FIG. 20(*a*)). sc4 mRNA transcripts were not observed in the embryo of 3-6 dpa seed sections examined by in situ hybridization using a radiolabelled SC4 antisense RNA probe (data not shown). Therefore the sc4 expression observed at 6 dpa in the seed tissue is likely to be seed coat derived. After 6 dpa the expression of sc4 in the seed coat increased ~4-fold to its maximum detected level between 9-12 dpa. By 15 dpa sc4 expression had decreased by ~2.5-fold dpa and continued to decline to just detectable levels by 18 dpa (FIG. 3.7). Expression of sc4 could only be detected in the seed coat at 21-24 dpa when the filter was over-exposed. Gene expression of sc4 in the pod was detected from 12-21 dpa only after over-exposure of the filter (data not shown).

SC20

Northern blot analysis was carried out to determine specificity of sc20 expression in various soybean organs i.e., seed coat, embryo, stem, root, leaf, pod and flower (FIG. 10(*b*)). sc20 has seed coat-specific expression as its mRNA was detected only in the seed coat organ. The sc20 transcript was determined to be approximately 2.5 kb (data not shown). Even after prolonged exposure of the filter, no sc20 transcripts was detected in any of the other plant organs.

Northern blot analysis was performed to determine the temporal gene expression pattern of sc20 in seed coat, embryo and pod organs of soybean. Total RNA prepared from organs between 6-24 dpa were probed with a radiolabelled SC20 cDNA probe. sc20 expression was detected at 9 dpa and rose 1.5 fold to its maximum observed level at 12 dpa (FIG. 24). By 18 dpa accumulation of sc20 mRNA had decreased fold. Prolonged exposure of the filter enabled detection of sc20 expression at 6 dpa and 21-24 dpa. No gene expression was observed at any stage of embryo or pod development examined even after prolonged exposure of the filters. This confirmed that sc20 expression was seed coat-specific.

b) In Situ Hybridization

To analyze the distribution of the clones mRNA expression with respect to cell differentiation during development, in situ hybridization, on sections from 3, 6, 9, 12, 15, 18, 21 and 24 DAF seeds was used. Seeds or parts of seeds were fixed in FAA fixative (50% ethanol, 5% acetic acid and 3.7% formaldehyde), dehydrated in an ethanol/tertiary butyl alcohol series and infiltrated and embedded in paraplast plus. Sections (5-10 μm) were cut on a microtome, transferred onto Superfrost slides which are positively charged to allow better adherence of the sections to the slide surface. Prior to in situ hybridization the samples were dewaxed in a xylene/ethanol series. In situ hybridization was carried out with $^{35}$S-labelled cDNA sense and anti-sense probes following the method of Cox and Goldberg (1998).

Ep

For the in situ analysis of Ep expression, flowers were tagged on days of full anthesis when the banner petal was fully extended and harvested at three day intervals from 1-30 days post anthesis (DPA), and at 45 DPA [19]. Tissue samples were fixed in a solution of 3.7% formaldehyde, 50% ethanol, and 5% acetic acid for 3 h at room temperature, dehydrated in an ethanol series (50, 60, 70, 80, 90, 95, 100%) then infiltrated with t-butyl alcohol (TBA) in ethanol in a stepwise series (25, 50, 75, and 100%), followed by infiltration with Paraplast and several changes of pure melted Paraplast at 57° C. After infiltration, samples were placed in blocks and allowed to harden. Sections of 8-10:m were cut on a rotary microtome and affixed to glass slides. Prior to hybridization, sections were de-waxed in xylene, and re-hydrated in an ethanol series (100, 95, 85, 70, 50, 30, 15, 0% ethanol in distilled RNAse free water).

Figure 13D:
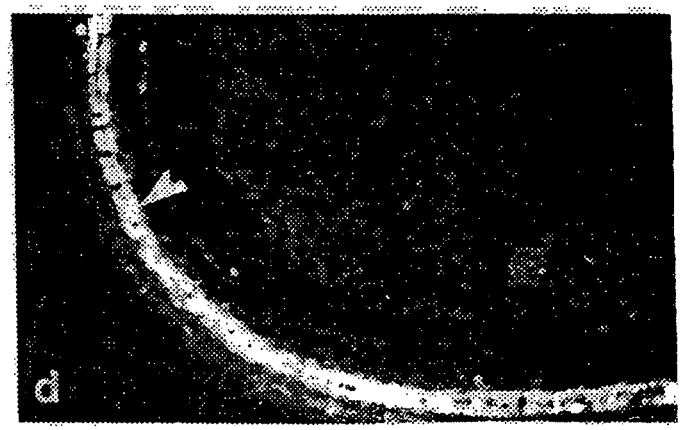
Figure 13E:
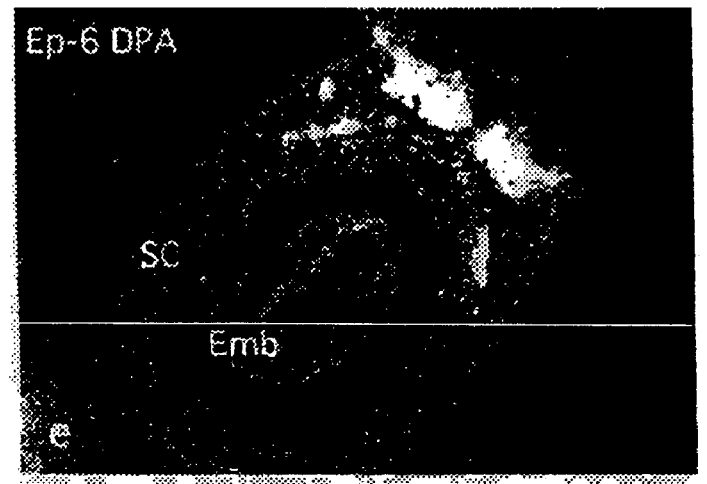
Figure 13F:
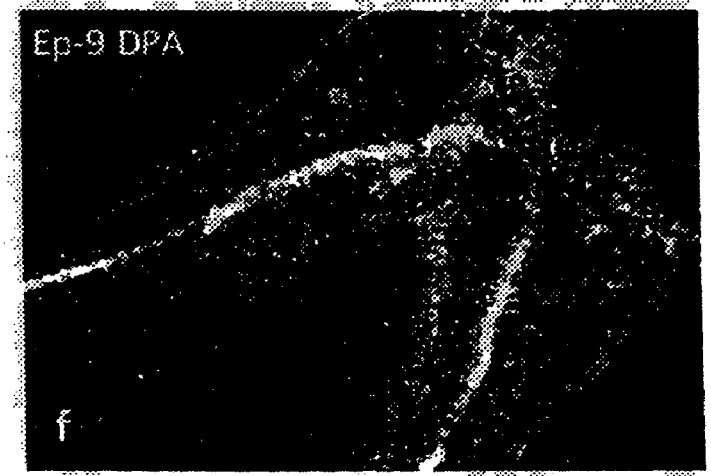
Figure 13G:
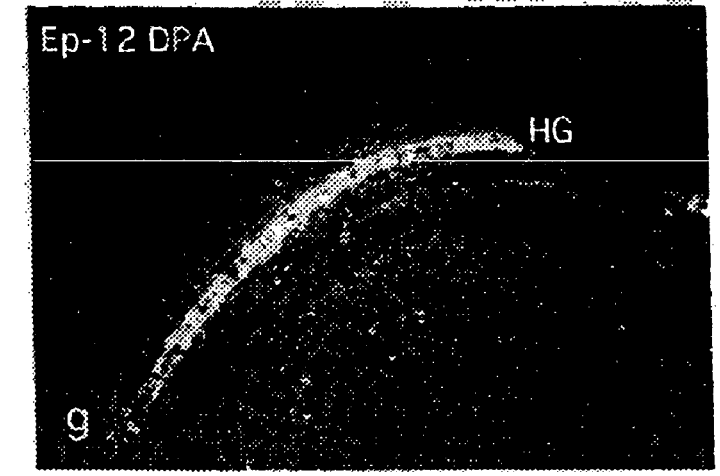

Localization of RNA was performed with $^{35}$S-labelled RNA probes generated from Ep cDNA clones. The prehybridization, hybridization, and wash conditions followed published methods (Cox K. H., and Goldberg R. B. 1988, Analysis of plant gene expression. In Shaw CH (ed), Plant Molecular Biology: A Practical Approach, pp. 1-35. IRL Press, Oxford). Briefly, sections were treated with Proteinase K and acetylated with acetic anhydride in triethanolamine. The sections were then hybridized with $^{35}$S—RNA probes overnight at 42° C., washed, and dehydrated in an ethanol series before application of Kodak NTB-2 track emulsion. After 1 week at 4° C., slides were developed in Kodak D-19 developer, fixed in Kodak Fix, and stained in Toluidine Blue O (0.05% in 50 mM Acetate buffer, pH 4.5). Slides were then dehydrated in an ethanol and xylene series, and mounted in Permount. Slides were photographed on Kodak EPL 400 slide film, using dark field optics The expression of a gene under the control of the Ep (peroxidase) promoter (nucleotides 1-1532 of SEQ ID NO:2, also see co-pending U.S. patent application Ser. No. 08/723,414 and 08/939,905, both of which are incorporated by reference) is localized within the hourglass cells (arrow; FIG. 13(d)) within the seed-coat at 18 days after anthesis. Expression of Ep is first detected at 6 DPA in the thin-walled parenchyma of the outer integument, adjacent to the thick-walled parenchyma, and flanking the hilum region (FIG. 13(e)). By 9 DPA a thin band of expression extends around the entire seed coat, at the junction of the thin-and thick-walled parenchyma (FIG. 13(f)). Expression shifts to the hourglass cells as they begin to develop, at 12 DPA (FIG. 13(g)).

HP

Figure 14A:
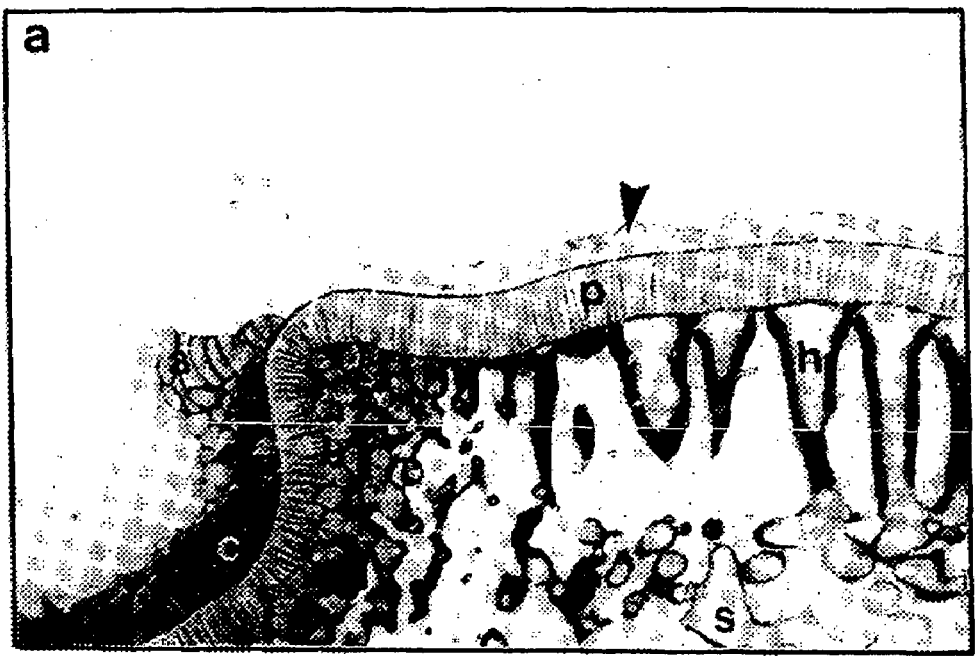
FIG. 14 shows light micrographs of a seed-coat obtained from soybean.
Figure 14B:
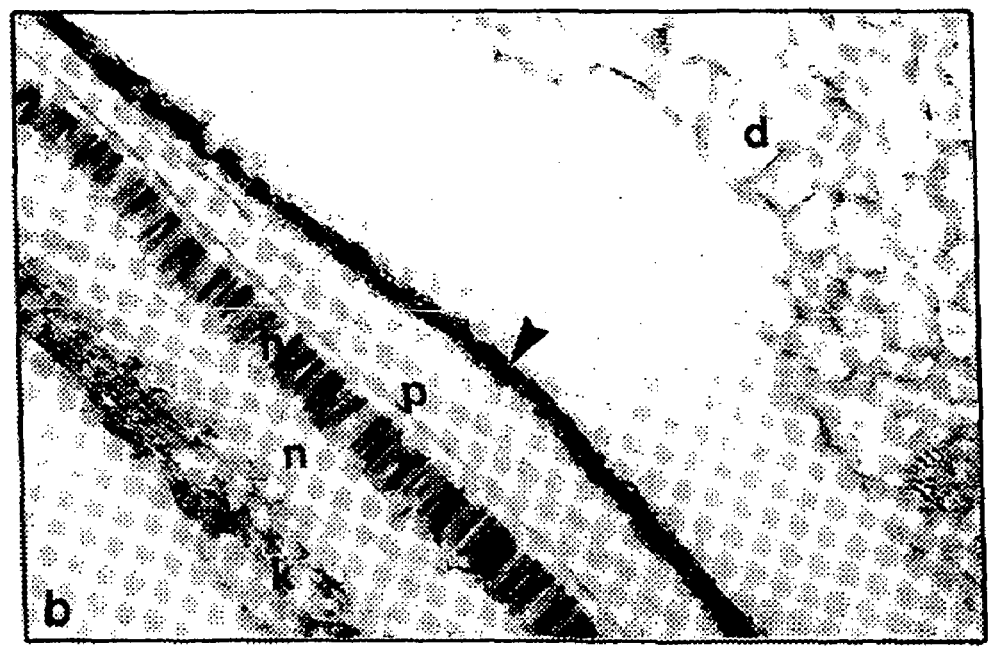
Figure 14C:
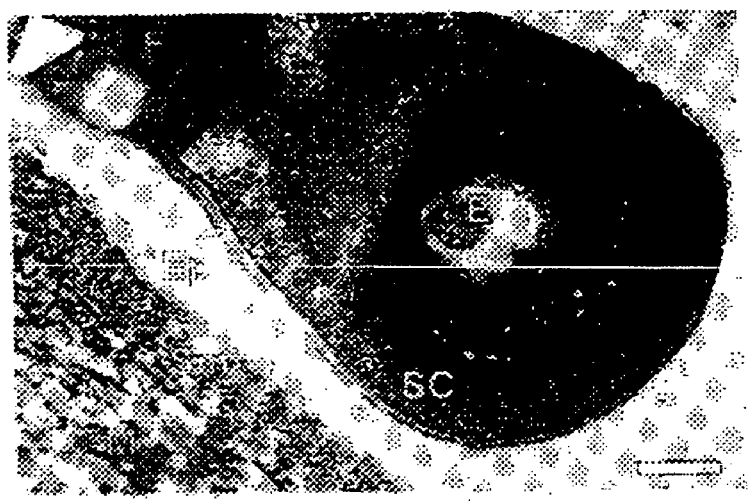
Figure 14D:
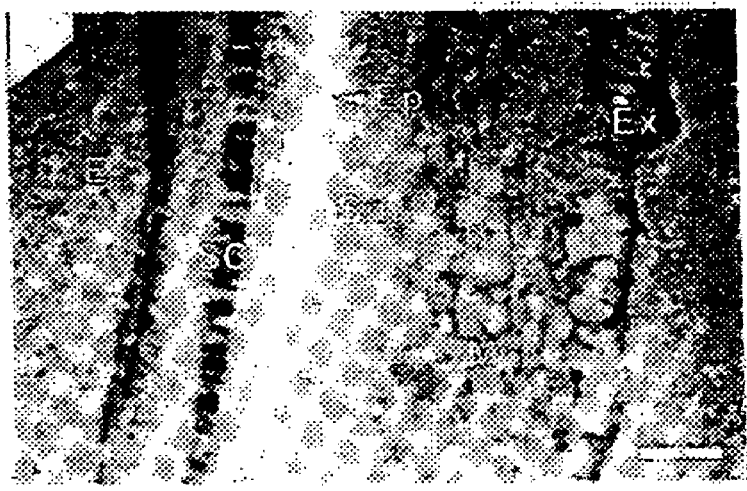

For the analysis of HP (FIGS. 14(c) and (d)), tissue samples were fixed in a solution of 50% ethanol, 5% acetic acid, 3.7% formaldehyde for 3 h at room temperature, dehydrated in an ethanol series (50, 60, 70, 80, 90, 95, 100%) then infiltrated with t-butyl alcohol (TBA) in a stepwise series (25, 50, 75, and 100% TBA in ethanol), followed by infiltration with Paraplast by gradual addition of increasing amounts of Paraplast to 100% TBA, followed by several changes of pure melted Paraplast at 57° C. After infiltration, samples were placed in blocks and allowed to harden. Sections of 8 to 10 um were cut on a rotary microtome and affixed to glass slides. Prior to hybridization, sections were de-waxed in xylene, and re-hydrated in an ethanol series (100, 95, 85, 70, 50, 30, 15, 0% ethanol in distilled RNAse free water). Sections were then treated with Proteinase K and acetylated with acetic anhydride in triethanolamine. Sections were hybridized with $^{35}$S—RNA probes overnight at 42° C., then washed and dehydrated in an ethanol series before application of Kodak NTB-2 track emulsion. After 1 week at 4° C., slides were developed in Kodak D-19 developer, fixed in Kodak Fix, and briefly stained in Toluidine Blue O before dehydrating in an ethanol and xylene series, then mounting in Permount. Slides were photographed on Kodak EPL 400 slide film, using dark field optics.

The expression of a gene under the control of the HP promoter (nucleotides 1-2526 of SEQ ID NO:7) is localized within the membranous endocarp (arrow, FIG. 14(b)) at 12 days after anthesis. At six days post anthesis (DPA) expression of HPS is limited to the membranous inner layer of the pericarp. By 12 DPA expression is very strong and the inner epidermis is showing signs of becoming detached from the rest of the pericarp and, in places, is adhering to the seed surface. Tissue sections from this stage of development also showed strong hybridization signals in the sclerenchyma, indicating that HP expression occurs throughout the endocarp.

SC4

Figure 21B:
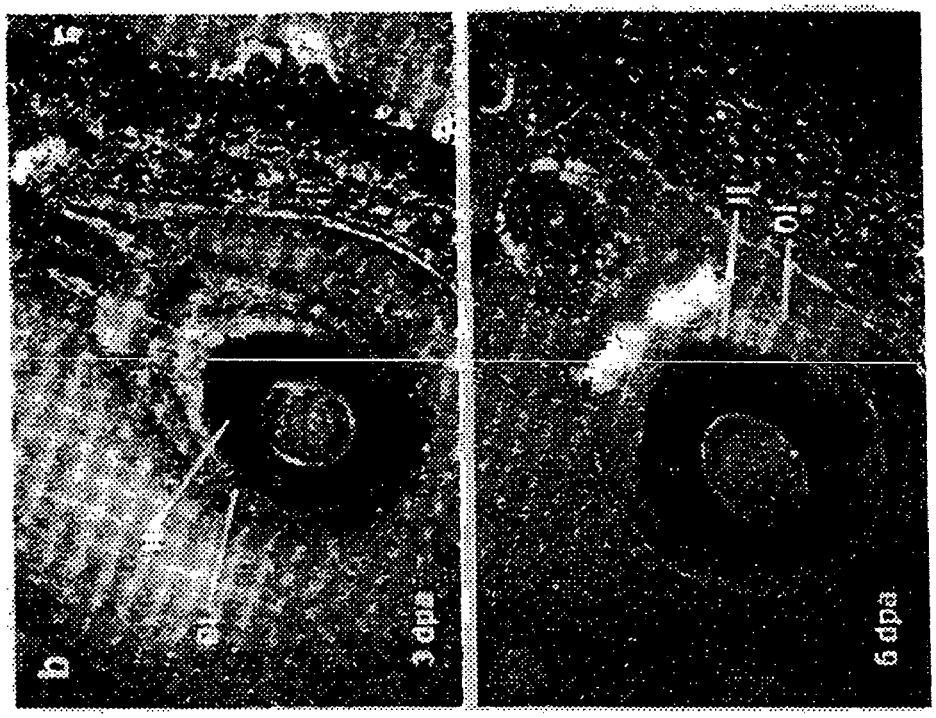
FIG. 21, shows the localization of SC4 mRNA in Seed coat organs of soybean by in situ hybridization. Transections of seed coats at 3 days past anthesis (dpa) and 6 dpa. Hybridization to Antisense, FIG. 21(a), and sense, FIG. 21(b) SC4 labelled RNA probes. Abbreviations, II—inner integument, OI outer integument, P pod. Bar equals 100 μm.
Figure 21A:
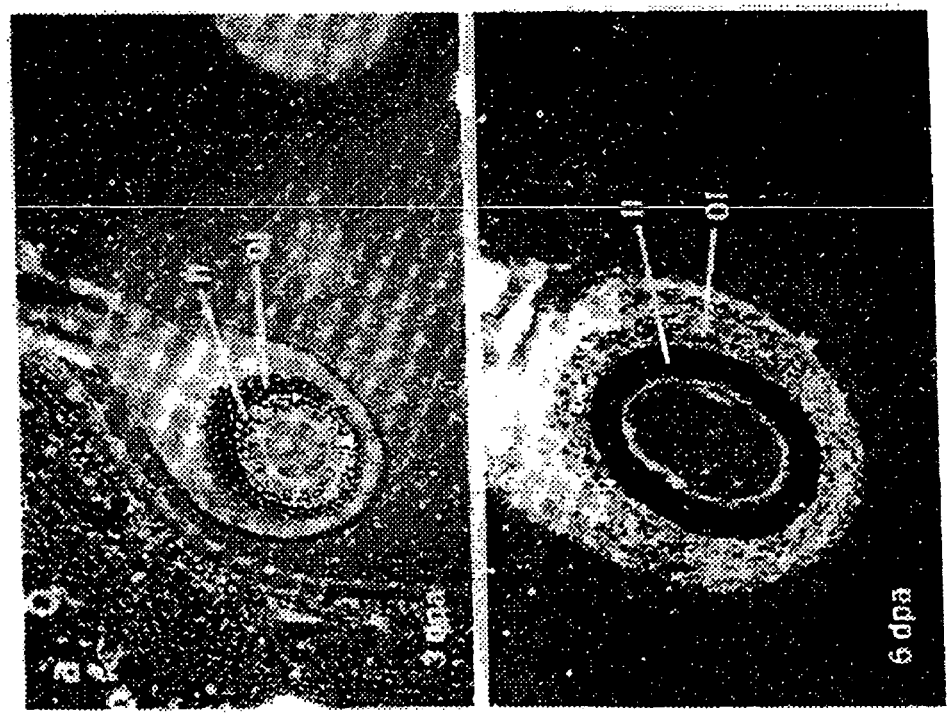

To analyse the distribution of sc4 expression with respect to cell differentiation during seed coat development in situ hybridization was performed on seed sections from 3-24 dpa seeds. The seed sections were hybridized with radiolabelled sense and antisense SC4 RNA probes which were detected by exposure of the sections to photographic emulsion. Within the seed sections the antisense or sense RNA probes can be localized by observing the accumulation of silver grains (produced in the emulsion by the emitted β-particles) under dark-field illumination with a light microscope. Cell walls of some plant structures can be birefringent (i.e., reflect light) under dark-field illumination. Two birefringent areas can be observed in both the hilum and the funiculus of the seed sections in FIG. 21 therefore any expression or lack there-of by sc4 will be masked in these locations.

sc4 was expressed throughout the inner integument of the seed coat at 3 dpa (FIG. 21). By 6 dpa the expression pattern of sc4 had changed, and was localized to the outer integument parenchyma but not to the vascular tissue embedded within this layer. sc4 expression in the outer integument was maintained until 18 dpa after which time no further expression was detected (see Table 4 below). In concurrence with northern blot analysis, the in situ hybridization results revealed that sc4 expression increased to a maximum between 9-12 dpa and decreased thereafter (Table 4). In addition, expression of sc4 was not observed in the embryo of seed at 3-6 dpa.

The expression of a gene under control of the SC4 promoter (nucleotides 1-5514 SEQ ID NO:9) within soybean seed coat at 3 days after anthesis is also shown in FIG. 13(a). Expression is localized within the inner integument (arrow; FIG. 13(a)). Other areas of brightness in this figure include the recurrent vascular bundles in the funiculus, and the trichomes of the pod (the bright areas are due to the birefringence of crystalline areas in the cell walls, and are also present in the negative control; data not shown).

SC20

In situ hybridization was carried out to analyse the spatial gene expression pattern of sc20 within the seed coat between 3-24 dpa. Seed sections were hybridized with radiolabelled sense and anti-sense SC20 RNA probes. No birefringent cell structures were evident in the seed sections used (FIG. 24).

Gene expression of sc20 was localized to the thick-walled parenchyma of the outer integument (see FIGS. 13(b) and 24). The temporal expression pattern of 9-21 dpa expression with an observed peak at 12 dpa was almost identical to that determined by northern blot analysis (Table 4, in Examples). sc20 transcripts were not detected in the embryo between 3-6 dpa. The in situ hybridization results of the seed sections concur with the northern blot analysis that within the seed organ sc20 is expressed only in the seed coat organs.

Expression of gene under control of the SC20 promoter (1-2450 of SEQ ID NO:8) is seen in FIGS. 13(b) and 24.

SC21

The expression of a gene under the control of SC21 (see FIG. 11(b)) within seed coat tissues at 15 days after anthesis is localized in the thin-walled parenchyma of the outer integument, including the area immediately surrounding the tracheid bar (arrow; FIG. 13(c)).

c) Construction of Genomic Libraries

In order to characterise the gene corresponding to seed coat cDNA clone(s), several genomic libraries were constructed in λ vectors from total DNA isolated from etiolated seedlings of various soybean cultivars. Two soybean genomic libraries were constructed in ILambda FixII (Stratagene, La Jolla, Calif.) from the total DNA isolated from etiolated seedlings of soybean [Glycine max (L.) Merrill] cvs. Harosoy 63 and Harovinton. The DNA was partially digested with Bgl II prior to ligation into the cloning vector.

Genomic clones corresponding to the cDNA clone SC4 and SC20 were obtained. Lambda DNA was isolated from each plaque. An ~8 kb Xba I fragment from the SC20 lambda clone and an ~8 kb Sac I fragment from the SC4 lambda clone, identified by southern blotting, were ligated into pBlueScript-SK (Stratagene, La Jolla, Calif.) and transformed into E. coli TOP. 10 cells.

Southern blot analysis of genomic soybean DNA, was carried out with 7 seed coat cDNA probes to determine similarities between clones and whether the clones represent a single gene or a gene family. Southerns were also performed to determine the occurrence of the seed-coat specific genes within other dicotyledonous and monocotyledonous plant species. Soybean genomic DNA was cleaved with several restriction enzymes and the resulting DNA fragments were size fractionated using agarose gel electrophoresis, denatured and transferred to nylon filters. Hybridization was carried out with radiolabelled cDNA probes.

Isolation of Genomic Clones

Initially, soybean genomic libraries were screened for the presence of the seed coat clone using the polymerase chain reaction with primers specifically designed from each cDNA sequence. This helped to target potential libraries for the isolation of genomic clones. The chosen genomic library was then screened using nucleic acid hybridization with cDNA probes. For genomic library screening hybridization conditions involved using modified Church's buffer (Church and Gilbert (1994) PNAS USA 81: 1991-1995) at 65° C.; wash 0.1×SSC 0.1% SDS at 52-55° C. Probes were random primed in presence of $^{32}$PdCTP using standard protocols.

Ep

A seed-coat peroxidase gene, corresponding to the Ep locus, was obtained from a soybean seed-coat library. The genomic DNA sequence comprises four exons spanning bp 1533-1752 (exon I), 2383-2574 (exon 2), 3605-3769 (exon 3) and 4033-4516 (exon 4) and three introns comprising 1752-2382 (intron 1), 2575-3604 (intron 2) and 3770-4516 (intron 3), of SEQ ID NO:2. Features of the upstream regulatory region of the genomic DNA include a TATA box centred on bp 1487; a cap signal 32 bp down stream centred on bp 1520. Also noted within the genomic sequence are three polyadenylation signals centred on bp 4520, 4598, 4663 and a polyadenylation site at bp 4700. The promoter region of the genomic sequence comprises nucleotides 1-1532 of SEQ ID NO:2 (see co-pending U.S. patent application Ser. Nos. 08/723,414 and 08/939,905, both of which are incorporated by reference).

HP

For the isolation of the genomic HP gene, a genomic library was constructed from DNA isolated from the soybean cultivar Harosoy 63. The DNA was purified and partially digested with Bgl II prior to ligation into the cloning vector lambda FixII (Stratagene). The resulting library was amplified and screened with the hydrophobic protein cDNA probe (pHPScDNA1). A positive clone was identified, purified, and found to contain a 14 kb insert. The entire insert was subcloned into pBluescript KS(+) and named pHPS1. The HP gene was determined by PCR analysis to lie near one end of the 14 kb Bgl II fragment (for restriction map see FIG. 11(c)). This region of the pHPS1 insert was sequenced by primer walking, and 3368 bp of this sequence data is disclosed here (SEQ ID NO:7). Aside from the polyadenylation site, the cDNA sequence (pHPScDNA1) exactly matches a stretch of sequence encoded on the genomic clone (pHPS1), indicating that this gene contains no introns. Additionally, a TATA box consensus signal was identified 81 bp upstream from the ATG translation start site.

SC4

A genomic clone corresponding to SC4 cDNA clone was isolated from the soybean genomic library Harosoy 63 (Bgl II digest). The genomic sc4 clone is 8310 bp in length (SEQ ID NO:9). The promoter region is found between nucleotides 1-5514 of SEQ ID NO:9. The restriction map is provided in FIG. 11(d).

SC20

A genomic clone corresponding to SC20 cDNA clone was isolated from soybean genomic library prepared from cv Harovinton (GigapackGold packaging). The genomic sc20 clone is 7235 bp in length (see FIG. 23(a), SEQ ID NO:8). Alignment of sc20 genomic and SC20:2 cDNA sequences revealed that sc20 contained eight introns of 94 bp, 101 bp, 185 bp, 80 bp, 154 bp, 112 bp, 110 bp and 93 bp respectively (FIG. 23(a)). A search (www.hgc.lbl.gov/cgi-bin/promoter.pl) of the 5' upstream region of sc20 revealed three potential transcription start sites at positions 1085, 1156 and 2272. The promoter region is found between nucleotides 1-2450 of SEQ ID NO:8. The restriction map of SC20 is presented in FIGS. 11(a) and 23(a).

SC21

A genomic clone corresponding to SC21 cDNA clone was isolated from the soybean genomic library prepared from Harosoy 63 (EcoR1 digest). The DNA of the SC21 genomic clone was digested with several restriction enzymes, fractionated by agarose gel electrophoresis and transferred onto nylon membrane. Hybridizations were carried out using radiolabelled cDNA. A restriction map of this clone is presented in FIG. 11(b).

Southern Analysis

SC4

Southern blot analysis was carried out to examine the gene family composition of sc4. Soybean genomic DNA was cleaved with Eco RI, Hind III and Xba I, which do not have recognition sites in the SC4c cDNA sequence. Under conditions of low to high stringency (i.e., from 40-10° C. below Tm of the probe) the SC4 cDNA probe hybridized to a single band (FIG. 22) and therefore sc4 appears to be a single gene.

SC20

Southern blot analysis was performed to ascertain whether sc20 is a single gene or a member of a gene family. Soybean genomic DNA was cleaved with Eco RI, Hind III, Xba I and Eco RV which have three, four, two and one recognition site(s) respectively in the sc20 clone (see FIG. 23(a)). Hybridization was carried out with radiolabelled SC20 cDNA probe which could anneal from the middle of exon 6 to the Eco RI site on exon 9. For each digest the probe was expected bind to only one of the resulting sc20 restriction fragments. Under conditions of high stringency to detect genes with at least 90% similarity to sc20 the probe hybridized to a single band (FIG. 25(b)). Under medium stringency conditions to observe genes with 80% similarity to sc20 it was observed that the SC20 probe annealed to 2-3 bands for each digest (FIG. 25(a)). Under conditions of low stringency i.e., 40° C. below Tm the SC20 probe hybridized to several more bands from each digest (data not shown). This suggested that sc20 is a member of a small gene family composed of 2-3 members and that the soybean genome contains several genes which are more distantly related to sc20.

Southern blot analysis was performed to determine the occurrence of the seed-coat genes within the following plant species: pea (*Pisum sativum*), canola (*Brassica napus*), oat (*Avena sativa*), onion (*Allium cepa*), pepper (*Capsicum annuum*), mimosa (*Mimosa pudica*), black spruce (*Picea mariana* (Mill B.S.P.), birch (*Betula pendula* Roth). Genomic DNA was cleaved with EcoRI and the resulting DNA fragments were fractionated using agarose gel electrophoresis, denatured and transferred to nylon filters. Hybridization was carried out with radiolabelled SC4 (FIG. 22(b)), SC20 (FIG. 25(c)), SC21, Ep locus peroxidase, and HP cDNA probes, using modified Church's buffer at 65° C. The filters were washed with 2×SSC, 0.1% SDS at 42° C. for 30 minutes, followed by 0.1×SSC, 0.1% SDS at 65° C. for 30 minutes. SC4, SC20 and Ep locus peroxidase cDNA hybridized to the genomic DNA of soybean only. SC21 cDNA hybridized to the genomic DNA of both soybean and oat. HP cDNA hybridized to the genomic DNA of soybean.

Analysis of Promoter Activity

The developmental expression of genes under the control of SC4, SC20 SC21 and the peroxidase promoter were further characterized during development of the seed coat by in situ hybridization as described above. The results are summarized in Table 4.

Developmental analysis of SC20 indicates that the promoter is highly active at 12 DAF within the outer integument and thick walled parenchyma, however, activity of the SC20 promoter is detectable from about 9 DAF (as per FIG. 13(b)) to about 18 DAF, and is partially detected at 21 DAF.

The SC4 promoter is active from about 3 daf (also see FIG. 13(a)) to about 6 DAF within the inner integument, and then is highly active at 9 DAF within the outer integument and stellate parenchyma, and strongly active at 12 DAF in these same tissues. The SC4 promoter is still active within the outer integument up to 18 DAF.

The SC21 promoter is active throughout seed coat development during all stages examined, from 3 about DAF to about 24 DAF, with strongest activity noted from about 9 DAF to about 15 DAF (also see FIG. 14(c)). The gene under the control of the SC21 promoter is expressed primarily within the outer integument and derived tissues.

The Ep (peroxidase, see co-pending U.S. patent application Ser. Nos. 08/723,414 and 08/939,905, both of which are incorporated by reference) promoter is active from about 6 DAF to about 24 DAF. Expression of the peroxidase gene, from about 12 DAF to about 24 DAF, is predominantly within cells of the outer integument, and the hourglass cells (see also FIG. 13(d)).

The HP promoter is active from about 9 daf through to about 24 daf. The promoter is active within the membranous endocarp throughout this period of time (see also FIG. 14(b)).

TABLE 4

Radioactive in situ Hybridization ($^{35}$S) of Soybean Seed Coat Tissue (Glycine max var. Maple Presto):
Developmental study with seed coat specific clones and peroxidase clones

| | SC 20 | SC 4 | SC 21 | Ep | HP |
|---|---|---|---|---|---|
| 3 daf | − | ++ (inner integument) | + (outer integument, subhilum region) | − | − |
| 6 daf | − | ++ (outer integument) | + (thin-walled outer integument except vascular layer; gradient from hilum to bottom of seed) | + (localized beneath recurrent vascular bundles) | − |
| 9 daf | + (outer integument, thick walled parenchyma) | +++ (outer integument except vascular layer) | ++ (thin-walled outer integument except vascular layer; gradient from hilum to bottom of seed) | + (outer integument; thin walled parenchyma beneath vascular tissue) | ++ membranous endocarp of the pod |
| 12 daf | ++ (outer integument, thick walled parenchyma) | +++ (outer integument except vascular layer) | ++ (thin-walled outer integument except vascular layer) | ++ (outer integument except vascular layer; hourglass cells) | +++ membranous endocarp of the pod |
| 15 daf | + (outer integument; thick & thin walled parenchyma except vascular layer) | + (outer integument except vascular layer) | ++ (thin-walled outer integument except vascular layer) | ++ (outer integument except vascular layer; hourglass cells) | +++ membranous endocarp of the pod |
| 18 daf | + (outer integument; thick & thin walled parenchyma except vascular layer) | (+) | ++ (thick & thin walled parenchyma of outer integument except vascular layer) | ++ (outer integument except vascular layer; hourglass cells) | +++ membranous endocarp of the pod |
| 21 daf | (+) | − | ++ (thick & thin walled parenchyma of outer integument except vascular layer) | ++ (outer integument except vascular layer; hourglass cells) | +++ membranous endocarp of the pod |

TABLE 4-continued

Radioactive in situ Hybridization ($^{35}$S) of Soybean Seed Coat Tissue (Glycine max var. Maple Presto):
Developmental study with seed coat specific clones and peroxidase clones

| | SC 20 | SC 4 | SC 21 | Ep | HP |
|---|---|---|---|---|---|
| 24 daf | – | – | ++ (thick & thin walled parenchyma of outer integument except vascular layer) | ++ (outer integument except vascular layer; hourglass cells) | +++ membranous endocarp of the pod |

+++ highly expressed, many silver grains;
++ moderate expression;
+ low expression;
(+) fading expression;
– no expression distinguishable Seed Surface Analysis of Dull and Shiny Soybean Varieties Seed surface proteins of several different soybean varieties were compared by SDS-PAGE analysis. A single seed was placed in a 2 ML plastic capped test tube and surface proteins were extracted by adding 0.5 mL of a buffer-detergent solution (10 mM Tris-Cl (pH 7.5) 0.5% SDS, 20 mM DTT) and placing the tube in a boiling water bath for 2 min. The contents of the tube were mixed and a sample was withdrawn and centrifuged for 5 min at 14,000 g. The proteins in the supernatant were electrophoretically separated on 15% acrylamide gels in the presence of SDS (Fling and Gregerson (1986) *Anal Biochem* 155, 83-88) and detected by silver staining. This analysis revealed that the 8.3 kD hydrophobic protein is by far the most abundant protein molecule occurring on the seed surface of 'Dull' seeded varieties. Only trace amounts of hydrophobic protein was detected on the surface of 'Shiny' seeded soybean varieties (results not shown).

Analysis of seed coat tissues using light microscopy indicated that the membranous endocarp of the pod wall remains in association with the seed-coat (FIG. 14(*a*). Scanning electron microscopy (SEM) of the seed surface of soybeans also showed obvious differences between 'Dull' (e.g. cultivar Clark) and 'Shiny' (e.g. cultivar Williams 82) varieties (see FIG. 16). Whole seeds were sputter coated with gold and examined by SEM at several magnifications. When viewed with the naked eye, 'Dull' varieties present a surface with a powder-like coating whereas 'Shiny' types appear to have a smoother and more light-reflective surface. Examination by SEM at low magnification (18x) reveals that the surface of 'Dull' types is uniformly covered with small, dimple-like indentations and bits of adhering material. These indentations are also visible on 'Shiny' types, but the surface is virtually free of adhering material. At higher SEM magnifications, the surface of 'Dull' types appears rough and ragged whereas the 'Shiny' seeded soybeans have a relatively smooth and undulating surface.

Without wishing to be bound by theory, it appears that the adhering material on the 'Dull' seeded types are remnants of the membranous endocarp tissue and is rich in hydrophobic protein. The expression of the hydrophobic protein in the endocarp causes bits of this tissue to stick to the seed surface, resulting in the 'Dull' phenotype. Lack of expression similarly may result in the 'Shiny' phenotype. The hydrophobic protein may be involved in the adherence of the endocarp to the seed surface.

Analysis of 'Dull' and 'Shiny' Seeded Varieties

Total genomic DNA was extracted from 'Dull' or 'Shiny' seeded varieties and amplified by PCR using primers targeted to the HP gene. The resulting amplification products were clearly polymorphic between the two genotypes. Good amplification of target segments of DNA were regularly observed when template DNA was from 'Dull' types whereas DNA from 'Shiny' types produced multiple products or products that were shorter or longer than expected, depending on the primer combination. These results indicate that different alleles the HP gene occurs in 'Dull' and 'Shiny' types of soybean. This allelic variation causes profound differences in seed surface morphology and composition.

To compare HP gene structure in two different seed luster phenotypes that were also different in the amount of HP present on the seed surfaces, we hybridized genomic DNA blots with probes derived from the HP cDNA sequence under high stringency conditions.

Soybean genomic DNA was isolated from frozen, lyophilized tissue according to the method of Dellaporta et al., (1983). Restriction enzyme digestion of 30 µg DNA, separation on 0.5% agarose gels and blotting to nylon membranes followed standard protocols (Sambrook et al., 1989). Digoxigenin labelled cDNA was prepared and used to probe DNA blots according to the instructions provided by the manufacturer (Boehringer Mannheim). Hybridization was carried out at 65° C. for 16 h in 0.25 M $Na_2HPO_4$ (pH 7.2), 20% SDS, 1 mM EDTA and 0.5% blocking reagent (Boehringer Mannheim). Filters were then washed 4x15 min at 22° C. in high stringency wash solution (20 mM $Na_2HPO_4$ (pH 7.2), 1% SDS and 1 mM EDTA), followed by 3x15 min washes in the same solution at 68° C.

Figure 18:
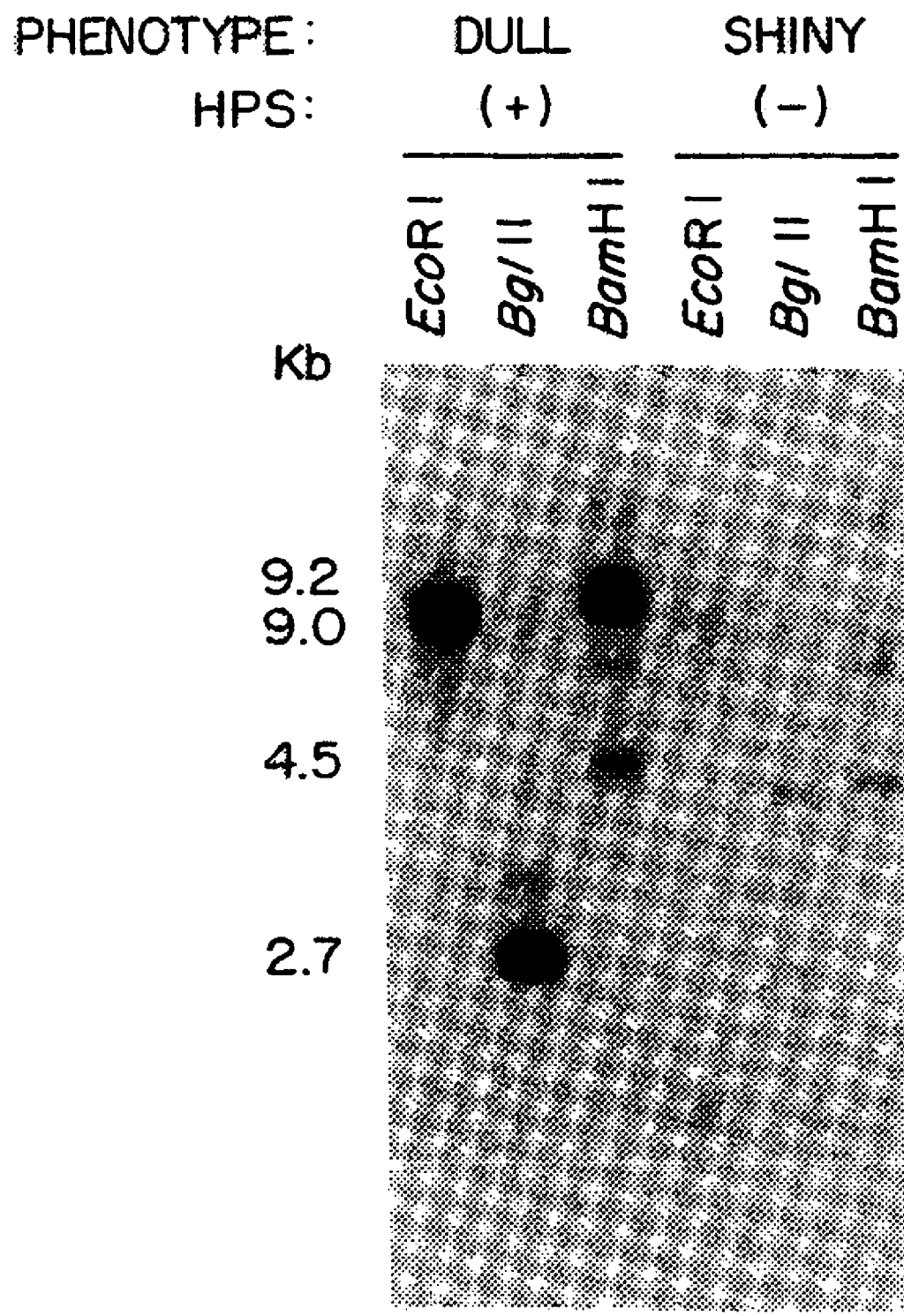
FIG. 18 shows restriction fragment length polymorphisms between dull and shiny phenotypes. Genomic DNA from dull (cv Harosoy 63) and shiny (cv Williams 82) soybeans with abundant (+) or trace (−) amounts of HPS on the seed surface, was digested with restriction enzymes, electrophoretically separated, blotted, and hybridized to HP cDNA probe. The size of hybridizing fragments was estimated by comparison with standards and is shown on the left.

A typical result from such a Southern analysis is shown in FIG. 18. Genomic DNA blots from cultivars that accumulated large amounts of HP on the seed surface produced strong hybridization signals. These intensely hybridizing fragments are not present in genomic DNA from plants that have only trace amounts of HP on the seed surface. However, several fainter signals are also present in DNA blots from both types of plants. These results indicate that sequences related to the HP cDNA are prevalent in the soybean genome, and that the HP gene structure is polymorphic among soybean cultivars. Soybean types that accumulate large amounts of HP on the seed surface possess additional copies of this gene.

All scientific publications and patent documents are incorporated herein by reference.

The present invention has been described with regard to preferred embodiments. However, it will be obvious to persons skilled in the art that a number of variations and modifications can be made without departing form the scope of the invention as described in the following claims.

We claim:

1. An isolated nucleotide sequence comprising the nucleic acid sequence defined by nucleotides 149-387 of SEQ ID NO:6, or nucleotides 2643-2881 of SEQ ID NO:7.

2. The isolated nucleotide sequence of claim 1 comprising nucleotides 32-387 of SEQ ID NO:6, or nucleotides 2526-2881 of SEQ ID NO:7.

3. A vector comprising the nucleotide sequence as defined in claim 2 under the control of a promoter.

4. A plant cell which has been transformed with the nucleotide sequence defined in claim 2, operatively linked to a promoter, and progeny thereof, wherein the progeny comprise the nucleotide sequence used to transform the plant cell.

5. A transgenic plant which has been transformed with the nucleotide sequence defined in claim 2, operatively linked to a promoter, and progeny thereof, wherein the progeny comprise the nucleotide sequence used to transform the plant.

6. A transgenic seed which has been transformed with the nucleotide sequence defined in claim 2, operatively linked to a promoter, and progeny thereof, wherein the progeny comprise the nucleotide sequence used to transform the seed.

7. A method for modifying luster of a seed coat comprising, introducing the nucleotide sequence of claim 2 under the control of a seed coat promoter, into a plant, and producing seed from the plant, wherein the luster of the seed of the plant, when compared to a similar plant that does not comprise the nucleotide sequence, is reduced.

8. A method for imparting a dull luster to a seed comprising, introducing the nucleotide sequence of claim 2 under the control of a seed coat promoter into a plant, and producing seed from the plant, wherein the luster of the seed of the plant, when compared to a similar plant that does not comprise the nucleotide sequence, is dull.

9. A vector comprising the nucleotide sequence as defined in claim 1 under the control of a promoter.

10. A plant cell which has been transformed with the nucleotide sequence defined in claim 9, operatively linked to a promoter, and progeny thereof, wherein the progeny comprise the nucleotide sequence used to transform the plant cell.

11. A transgenic plant which has been transformed with the nucleotide sequence defined in claim 9, operatively linked to a promoter, and progeny thereof, wherein the progeny comprise the nucleotide sequence used to transform the plant.

12. A transgenic seed which has been transformed with the nucleotide sequence defined-in claim 9, operatively linked to a promoter, and progeny thereof, wherein the progeny comprise the nucleotide sequence used to transform the seed.

* * * * *

SEQUENCE LISTING

<160> NUMBER OF SEQ ID NOS: 12

<210> SEQ ID NO 1
<211> LENGTH: 1070
<212> TYPE: DNA
<213> ORGANISM: Nicotiana tabacum

<400> SEQUENCE: 1

```
tctagacttg tcttttcttt acataatcct cttcttcttt tttttgttag tttcttctgt     60
tttatccaaa aaacgaatta ttgattaaga aatacaccag acaagttttt tacttctttt    120
tcttttttt tttgtggtaa aaaattacac ctggacaagt ttatcacgaa aatgaaaatt     180
gctatttaag ggatgtagtt ccggactatt tggaagataa gtgttaacaa aataaataaa    240
taaaaagttt atacagttag atctctctat aacagtcatc cttatttata acaatacttt    300
actataaccg tcaaatttat tttgaaacaa aattttcatg ttatgttact ataacagtat    360
tttattatag caaccaaaaa atatcgaaac agatacgatt gttatagagc gatttgattg    420
tatcattatc cacatatttt cgtaagccca attactcctc ctacgtacga tgaaagtaaa    480
ccaatttaaa gttgcaaaaa tccaatagat ttcaatactt cttcaactgg cgttatgtta    540
ggtaatgact cctttttaac ttttcatctt taatttgaag tttctttcat aaaagaaag    600
tttctagaag agaagtgttt taacacttct agctctacta ttatctgtgt ttctagaaga    660
aaaatagaaa atgtgtccac ctcaaaaaca actaaaggtg ggcaaatctc cacctattta    720
ttttattttg gattaattaa gatatagtaa agatcagtta taaacggagt tttgagttga    780
tacagtgaat tttaagatgt gtaccgattt aactttattt acatttatgt ttcgcacata    840
taagaagtcc gatttggaaa tactagattt tgtcaatcag gcaattcatg tggttgaaga    900
atttaagtta tatacaatga tgatataaag aatttttata ctattagtgc aaattaatcg    960
attactaaaa attattattc tattaattta tgctatcgtg cctccccaac ccgtcgaccg   1020
cggtacccgg tggtcagtcc cttatgttac gtcctgtaga aaccccaacc              1070
```

<210> SEQ ID NO 2
<211> LENGTH: 4700
<212> TYPE: DNA
<213> ORGANISM: Glycine max

<400> SEQUENCE: 2

```
tagataaaaa aatgggatat aattttttctc agatgttgtt tatactgttt ttttaatcag     60
aattaaaatt cctctttaat tatcgacata atttttttg gtgaatatta tcgacataat      120
tatttaatac aaatttttat tgtacataga agtgatactt caattttaat attggagaac    180
agtacgaaaa cataaaaaaa ctgttattag aagaaaaaaa tatatggaaa aggttagcta    240
catatattag ctaaattagt tgttctaatt ggctatataa accctattgt actctttgta    300
atctcacctt tttcatttaa atacatttct acttttttaag ttctatattt tctctcaatt   360
ttcttcgata aaccatgaaa tttaacatgg tatatcagcg ataccaccca ctttgaaagc    420
catgtatggc tagtatgggc agccaaaatt tgccctggtt caagcaaagc aagtgtttat    480
atagatgtga ctttgttga ggaactcatg ccaatggtac tgattgtgaa actgagaaaa     540
ctaatttgga gaatttgaat tatgatcatt aaatactcct ctcctgacta ccttcgtccc    600
tcaaatttgt accatcatta tttcccaaaa atttgattac aatgcactaa ttaatgaatg    660
tttcttacat tatcatatta tcatatctga cattttgttt ttacttttta taataattat   720
```

```
tttaaaaagt catacatgca aataattttt taatagttta cagttaaatt tttacagtaa    780
aaatgcatga aaattaaact ttattttttcc aagtcatcat ttagtcaaat cccaaaacaa   840
tgattatttt ttgcaaatga atgtttattg aacatttaaa tgtagcctaa ttaattctgg    900
ttatggtgtc aatgttccaa aacctaatgc aagatcttag caagtacata catagatcta   960
attttaaact tatctttacg caagagatat aaagattata catctagttt taaacattaa   1020
cttttgtttt tgtgttaaaa aacagtaaca ttttcttaat tttgtagagt gacgtgctcc   1080
aaccatatta acgaagattt taattggtat tcaagttcat gaacttagta aataagtttt   1140
ggtcttcagt tttcaatttt cattacaaca tttatgtaaa atatcaacgt tttctgaaat   1200
ttgttgcttg tgtgctccaa ccacatttaa gagattatag aaattaattt tcaagaagat   1260
aatgattcct actcttgctg gccctaccat agtacaataa atccactcat aaatcaacaa   1320
gtcgtcgtca taggcaattg ggcatcatat cataaacaat acgtacgtga tattatctag   1380
tgtctctcag tttactttat gagaaattat ttttctttaa aaaagttaa ttaataaaaa    1440 catttgcgat accgtgagtt acaagaaatc cgccgaattc atctctataa ataaaaggat   1500
ctatatgaga ggtaaaatca tattaactca aaatgggttc catgcgtcta ttagtagtgg   1560
cattgttgtg tgcatttgct atgcatgcag gttttttcagt ctcttatgct cagcttactc   1620
ctacgttcta cagagaaaca tgtccaaatc tgttccctat tgtgtttgga gtaatcttcg   1680
atgcttcttt caccgatccc cgaatcgggg ccagtctcat gaggcttcat tttcatgatt   1740
gctttgttca agtacgtact tttttttttc cttccaaaat gccctgcata tttaacaaga   1800
ttgctttgtt cacctagaaa aatgtgtttt tttcaacgat cttacgtacg tttgtttggt   1860
ttgaaaaata aatcagaaag agatcaagaa aatagctaga aagaaagcaa cgttttttta   1920
aaaggtattt agtgtgagaa aaatattaaa actgaagaga aagaaattaa ataagctttt   1980
cttgaatgat atttacatgt cttattaact taaagtcacc ttttttcttt aagttgtgct   2040
tgaagaaaaa agatgtcttt cagtttagtt ttgattaatg ctaattatat ttttaattaa   2100
ttaattaata ctatatatct atttaccata ttaattatta ctatatttca tgatgacaac   2160
agacaagtat tctaaagagg tatcggtaga tgattaattt ttttataaaa aaatcttttg   2220
cgtgtataga tattcttta taattggtgc agaaacttgt aatgctaatt gcaattaatc    2280
ttacattgat taactaatag ctataatcaa tatttaggtt aggtatagga gacaaatcaa   2340
gtgatctgaa caaattaagt tgttatattt gcattgtgac agggttgtga tggatcagtt   2400
ttgctgaaca acactgatac aatagaaagc gagcaagatg cacttccaaa tatcaactca   2460
ataagaggat tggacgttgt caatgacatc aagacagcgg tggaaaatag ttgtccagac   2520
acagtttctt gtgctgatat tcttgctatt gcagctgaaa tagcttctgt tctggtaatt   2580
aataactcct aattaattcc caaccattaa aaagttgcat gattggattc aaaattctat   2640
ggtattgggg ttctgatata aatttgtaat taaattgcac taaaaaaaat tatcatatac   2700
ttttaataaa aaaaatttat ctaatttaat ttattattaa aactattttt aaaattcaat   2760
cctaactctt ttttaatcgg agcatgtaag ctggcaccca ccgtatatcg ttggaagatg   2820
ctataaaacc atttaattaa tggatggaat cagtcaaaac attaattca aaatactctt    2880 aattgtgatt agtaatcatg ttcgggcaag ttacgttgtg tataattaat ttgacttaat   2940
cagataaaaa aacaaatgga cgcaagccgg ttggtataga tatcactggc ctgtagaata   3000
tgtggttttt cacgtttaaa taaaagctag ctactatatt atatttagtc tttttttttc   3060
```

```
ttaaacccat ttaacgtgat ttattgactg tgaaacatgt ttccacacac aggcttagaa      3120
actcctcgca actaacatct ccaaaatttg actatttatt tatgaagata attcatctat      3180
gatgttcaac tctattatat atatgtatca tcgcagtatt aagaattata atagtcaaat      3240
atagaagtat atcgggtaaa tgtagttgca tgtgcgacct gtttcgtgta aaatgcttat      3300
tctatatagc tttttttatt ggaaaataac gatgaactaa aaacgaaagg gtatcatata      3360
gtttgacttt tatgttagag agagacatct taatttggtc atatgttaaa taattaatta      3420
caatgcatac acaaatattt atgccatatc taaaaaatga taaaatatca taggtatact      3480
caactatatg atatccccat aacagaaatt gtacttttct tcaggcaatg aacttaacat      3540
ttctgtttgc taaaaacaaa catccactta agtggttcaa acatatttat gtaataattt      3600
acagggagga ggtccaggat ggccagttcc attaggaaga agggacagct taacagcaaa      3660 ccgaacccctt gcaaatcaaa accttccagc acctttcttc aacctcactc aacttaaagc      3720
ttcctttgct gttcaaggtc tcaacaccct tgatttagtt acactctcag gtatacataa      3780 tcaattttt atttgctatt agctagcaat aaaaagtctc tgatacagac atatttagat      3840
aaattaattt ctccataaac atttataata aaattatcaa tttatgtact taaaaattat      3900
ggattgaagc tcttttcatc caacttttac taaagttaag gtgcatataa tataaaataa      3960
actatctctt gtttcttata aaagattga agataagtta aagtctactt ataaatcatt      4020
aatatatgta taggtggtca tacgtttgga agagctcggt gcagtacatt cataaaccga      4080
ttatacaact tcagcaacac tggaaacccct gatccaactc tgaacacaac atacttagaa      4140
gtattgcgtg caagatgccc ccagaatgca actggggata acctcaccaa tttggacctg      4200
agcacacctg atcaatttga caacagatac tactccaatc ttctgcagct caatggctta      4260
cttcagagtg accaagaact tttctccact cctggtgctg ataccattcc cattgtcaat      4320
agcttcagca gtaaccagaa tacttttcttt tccaacttta gagtttcaat gataaaaatg      4380
ggtaatattg gagtgctgac tggggatgaa ggagaaattc gcttgcaatg taattttgtg      4440
aatggagact cgtttggatt agctagtgtg gcgtccaaag atgctaaaca aaagcttgtt      4500
gctcaatcta aataaaccaa taattaatgg ggatgtgcat gctagctagc atgtaaaggc      4560
aaattaggtt gtaaacctct ttgctagcta tattgaaata aaccaaagga gtagtgtgca      4620
tgtcaattcg attttgccat gtacctcttg gaatattatg taataattat ttgaatctct      4680
ttaaggtact taattaatca                                                  4700

<210> SEQ ID NO 3
<211> LENGTH: 1119
<212> TYPE: DNA
<213> ORGANISM: Glycine max

<400> SEQUENCE: 3
caatgctgcg ttaactccta gacattactg ggaaacgatg cttccaagaa ctcccttgcc        60
gaaagcaatc acagagctac taagccttga agtaggtcc atatttgaat atgccgggaa       120
tgatgaccag tcagaaagta ggtccatatt aggatacgct ggctataatc aagacgagga       180
tgatgtgagc aaacacaata tacaaatctt caacaggttg ttttttcttgg aagaggacct       240 gcgtgctggc aaaatattca acatgaagtt cgtcaacaac acaaaagcca cagtcccgtt       300
gctaccgcgc caaatttcga aacaaatacc gttctcagaa gataaaaaga gcaagtgtt       360 ggcgatgctt ggcgtggaag cgaactcaag caacgccaag atcatagcgg agaccattgg       420
tctttgccaa gagcctgcaa cggagggaga aaggaaacac tgcgcgactt cgttggagtc       480
```

```
catggttgat tcgtcgttt ccgcgctcgg gaagaacgtt ggtgctttct caacagagaa    540
agaaagggaa actgagtctg aaagtttgt agtggtgaaa atggggtga ggaagttggg     600 agatgataag gttattgcct gtcatccaat gagttaccct tatgttgtgt ttgggtgtca   660
tctagtgcca aggagtagcg ggtatttggt gcgcttgaag ggagaagatg gggttcgagt   720
gaaagcagtt gttgcgtgcc acagagacac gtcaaagtgg gaccataatc atggggcatt   780
caaagtgctc aatcttaagc ctgggaatgg tacagtatgc catgtcttca ctgaggggaa   840
tcttctttgg cttccaaatt agattaatta ccatatacat atttgtcctt gttctatcct   900
taaataagtg gaatcacctg aagaattgtg cgtaatgagt tgtttgtctt tgtggaaatt   960
gttatctgtc ttgcatcacc aaataggtat atataaaata acaggagcgt ggtatttgtt  1020
gcacaaaaat ggatttcaac cgatcaaaaa aatatagcct ttaccaatta aagggtttg   1080 gctttgttag caaataataa aaataaaata tcttgatgg                         1119
```

<210> SEQ ID NO 4
<211> LENGTH: 2447
<212> TYPE: DNA
<213> ORGANISM: Glycine max

<400> SEQUENCE: 4

```
caaagtttta acatgaaagg caataataca cttttgttgc atttattcta cactactctc     60
ttcctgtttc ttgtagtgtc aagttcatct tcaacaggga atgaaagtaa cgatgacact    120
aacagtaaag aagtttatat cgtgtacatg ggagctgcag attcaacaaa agcttctctt    180
aaaaatgagc acgctcagat tctgaattca gtgctaagaa ggaatgagaa tgccctagta    240
cggaactaca agcatggttt ctctgggttc gcagctcgtc tatcaaaaga ggaggcaaac    300
tcaattgctc agaaacctgg tgtggtgtct gttttccctg accccattct gaagctccac    360
actacacgtt catgggattt cctcaaaagc caaactcgtg tcaatatcga caccaaacca    420
aatacgctgt ccggttcttc ttttcttca tcagacgtca ttcttggcgt cttagacaca    480
ggcatatggc cagaggcggc gagttttagc gacaaggggt tcggtcctgt tccatcccga    540
tggaaaggca cctgcatgac atcaaaagac ttcaattcct cttgttgtaa caggaagata    600
attggcgcga ggttttaccc taacccagag agaaaacgg caagggattt caacggacat    660
gggactcacg tttcgtcgac ggcagtgggc gtgccggtga gtggcgcatc gttctatggt    720 ctggcggcg gacggcaag gggtgggtcc cctgagtcaa ggttggcggt ttacaaagtg     780 tgtgggctt ttgggtcatg tcctgggtcg gccattcttg cggggtttga cgatgccatt    840
cacgacggag tggatatctt gtcgctgtcg ctcggtggat tcggtggaac caaaaccgat    900
ttgaccaccg acccgattgc gattggagca ttccactccg tccagcgcgg catcctggtg    960
gtctgcgccg ccgggaacga cggagaacca ttcaccgttc tcaacgacgc accttggatt   1020
ttaaccgttg cagcttccac catcgaccgt gatcttcaat ccgacgtggt cttgggtaat   1080
aaccaagtcg tcaagggaag agccataaat ttctcccctc ttttaaattc tcccgattat   1140
ccaatgatat atgctgagtc tgctgccagg gcaaatatct ccaacataac tgatgcaaga   1200
caatgccacc cagattcatt agatccaaaa aaagtcatag gaagattgt ggtttgtgat    1260 ggaaaaaatg acatttatta ttcaactgat gagaaaattg tcatagtgaa ggcgttggga   1320
ggaataggtc tggttcatat tactgatcaa tctggatcag tagcattta ttatgtggac    1380 ttcccagtaa cagaggtaaa atcaaaacat ggcgacgcaa tcctccagta catcaactca   1440
```

```
actagccatc cagtgggaac aatactagca acagttacaa ttcctgatta taagcctgct    1500 cccccgggtgg gttattttc atcaagaggg ccttcattga ttacaagcaa tgttctcaag    1560
cctgatattg cagccccggg agttaacatt ctcgctgcat ggtttggaaa tgacacatca    1620
gaggttccaa aaggaagaaa gccctcacta tatcgcatac tctcaggaac ttccatggct    1680
actccacatg tttcagggct tgcatgcagt gtcaaaagaa aaacccccac ttggagtgcc    1740
tccgcaatca aatctgccat catgacttca gcaattcaaa atgacaattt gaagggtccc    1800
ataacaacgg attcagggtt gatagccaca ccttatgact atggagcagg ggcaattaca    1860
acatctgaac cattgcaacc ggggctagtt tatgaaacca caacgttga ctacttgaac    1920 tatttgtgtt acaatggact taacataacc atgataaagg tcatctccgg aactgtcccc    1980
gagaatttca attgtcccaa ggattcgagc tctgatctca tctccagcat caactaccct    2040
tccatagcag taaacttcac tggcaaagca gacgcggtcg tgagtagaac tgtcacaaac    2100
gttgacgaag aagatgaaac agtgtacttc cccgttgttg aagctcctag tgaagtaatt    2160
gtcacactct ttccatataa tcttgagttt acgacaagta ttaaaaaaca aagctacaat    2220
attactttca gaccgaagac ctccttgaag aaagatttgt ttggatctat cacttggagt    2280
aacgacaaat atatggttcg aattcctttt gtattaacta aatagtgaaa ttaaaaagta    2340
gcgatgaata aatgcaagct aagttcttcg tggtgcctac actcgagtcc tgattattta    2400
ttattcatat gccttctgtt taatttatt tattatactt tcagcct                   2447

<210> SEQ ID NO 5
<211> LENGTH: 829
<212> TYPE: DNA
<213> ORGANISM: Glycine max

<400> SEQUENCE: 5
gccttaaggc aacgacagcg agttcttctg ttgttcgttg actccaagga cggggtctta    60
gttggtggct tcgtggtttc cttctttggt ggcttcgtgg ttgttgtctt tgtcatcctt    120
gttgttgatg tcttcttcgg ttcggtctcc tcggatttct tcaacgtcaa ctctggctcc    180
tccaccactg tttcctctgt ctccttctct tcggtcgtcg tcttctcttt agtctcctct    240
tttgacttct tcactttctt cttcgtcttc tcggatttct tgatgacttt tgtctttgtc    300
ttagtcgtgg tcgtcgttgg tgtctccttc tcttgtttgg tcgactctgt caccttcggg    360
gtcatctcca aggacaactc tttgacttc gaatctgaat acctgtcaca ctcactcttt    420
ttgttcaaat ttttaccagg atcaacaccc ctagtaatcc agatggtaaa acgtacagta    480
caacttttcg aaaaaaaaaa taaataaaga aatcaaatga aataataatt atataataat    540
aatatactac caattcagaa accaacataa tacctcccat atggatgcac actcgtgttg    600
tgaaccgagg tgtagtcgca cgaatggtgc accactgtac tctttaagat cctcaacaca    660
taacttcact cgttcgacga cgaccacgac ctcaaatccc tactcccaaa taaataaacc    720
gtcccaatgt actcaaacac tactacacaa taacacaaag aaatccaaac ttatttacta    780
taaatgaaat tttttttttt tttttagat ctagctggcg tcgggttga                 829

<210> SEQ ID NO 6
<211> LENGTH: 700
<212> TYPE: DNA
<213> ORGANISM: Glycine max

<400> SEQUENCE: 6
taagctttca agagacaaac tgctttgaaa aatgggatcc aaggttgttg catccgttgc    60
```

-continued

```
ccttctcctc tccatcaaca ttcttttcat ttccatggtt agctccagca gccactacga    120
tccacagccc caaccttctc acgtcactgc tcttattaca cgacctagtt gtccggatct    180
gagtatttgc ctcaatattt taggcgggtc tctaggaacc gtggatgatt gttgtgccct    240
catcggtggt cttggtgaca ttgaagccat tgtgtgcctt tgcatccaac tcagggccct    300
cggaatatta aaccttaacc gtaatttgca gttaatatta aactcctgtg gacgaagcta    360
cccgtcaaac gccacttgcc cccgaaccta agaacagaat atgtatggca ctaattacca    420
tattacttcg tatcatggtg tttgtttgtt tgtctgtgtt taaagttaag gatgttatac    480
ccttcgtgcc tgctacatat atatagtggg cactataata ttaccaataa attaacgtcc    540
atatataaga ataataataa ataaataaat atttctatac aaataaaggt tacgtaatgt    600
tgttgttctc gtggatgggg atcttatctt cctcctcgct atctttgttt atcgtatttc    660
agtgaaagtt gttcaataaa agtccttgt tcaacaagta                           700
```

<210> SEQ ID NO 7
<211> LENGTH: 3368
<212> TYPE: DNA
<213> ORGANISM: Glycine max

<400> SEQUENCE: 7

```
tctttcgatc aatactaata aagtcttatt tgccttccag agacaattga gtccgttggc     60
acgcagagac aaattatggt aatttgcccc tttttgaaga cttcaatgtc tttcgatcaa    120
gactattaaa gtcttctttg ccttctagag acaaattatg gtcatctgat tcttttgaa    180 tacttcaatg tctttcaatc aagacaatca aagttttttc gaatacttca aagtcttctt    240
tgccttccgg agacaattaa gtctgttgga acgcagagac aaattatgat catctacccc    300
atttcgaaga cttcaatgtc tttcgataaa gactattaaa gtcttctttg ccttccggag    360
acaatcaagt tcattggcac gtagagacaa attatggtca tctgcctctt ttcgaatact    420
tcaatgtctt tcgattaaga ctatcaaagt cttcttttcc ttccggagac aatcaggttc    480
tttggcacgc agagacaaat tatgttcatc tgcctctttt cgaagacttc aatgtctttc    540
gatcaagact atcaaagtct tctttgcctt ccgaagacaa tcaagtctgt tggcacgcaa    600
agtttgagga aaaattggac gaagatcggg acaaatggac cgtatggttt gacggagcgt    660
caaacattct aggccatggc attggggcag tattggtctc tccggacaat caatgtgtac    720 cttttcacaac caggctagga ttcgactgca ccaacaacga tcttcggtgc aattactcaa    780
atcggggaac taaggtggaa tgaagttgtc gtcattttgg gcaaggacaa gggagttgtt    840
ggagctaacc atggcatagc aaaggagatt gagggagagg ataattaggg catcaacacc    900
catggaaccc atttaatttc ccaacataga ttgatagaaa tattattgca gtctctcttg    960
atagcttaaa tattgatgag caagtgctct tgcttgtggt ttctagctga acttacagg    1020 tacgagtata agattactaa acttgtttcg atcctgaacc cgaactcgcc tgtcacttaa    1080 aattttttaaa atttttgcat aatttaatca aaaggcataa aatttttatt actagttaat    1140 tttttttta gaattttac ataatttaat attattttct taactatttt ttagatacac    1200
gcgctataat aaatttattt atatatatgt agttaaaaat aaatgtttaa taatcaattt    1260 atttttcta aaatcaaatt tttaatattt ttttacaaaa aaatattttt ctaagttgaa    1320
tcgtgtatgg gacggggtca gggatacccg atatctgacg ggtacgagga tgagacaata    1380
aacttaaatc cgtcgagtat tggatacgag tatgggaata tgttggggag tcggggtaag    1440
```

```
gaattgagga acaatatcc atacccaccc gccctattgt catgtctaga cactacaaag    1500
aagggttaaa gaaacctaag ttaaaatagt agattatatg acatttagtc ctgtaaaaag    1560
aagaagagaa agatgtagaa aattttcaag aaagatatca agttaaataa tattttttcaa   1620 agtttgattt ttaattatat caaacaacgt agtgtgattc atgtaattgg tgacttacct    1680
actagtataa aaatttgttc tctttgttgt tgttgcatgt atggaatgaa ttttaaaaaa    1740
atcataaata taatttgaaa tcattttaaa attatgtaaa atcatttcga attattgatc    1800
tagattaaac aattacttag tgtaacaaga gaattttttgc ttagatttaa acttaatct     1860 ggctagcacc tagagattta ttttttgtaat gatccatgac aatatcataa ttatgataat   1920
atatgtcata atttaaattt gtattcatct ttctttaaaa aatatacttg aaagtgttaa    1980
attgtacttc aaagatttag catattagtt tagttctgga taataaatta aaattattat    2040
tctcaaaaat gagataattc tttcatgtac aattcttcat acatagtatc aaatgtcttc    2100
ttcattttat gacacatgcc ttttaatttt tatattaata aaattaattt tttattaaat    2160
taaataatat tttaatctct ttaatgcttg aattaatata ttttttttta aaaaactaag    2220
catgacaagg tatttacaat ttactctaga aataatatac actaattaac acaagaataa    2280
gtatttttca aaatattttt ttttcatac aaaccacaag tatctgcaac aaaacttcct    2340
ttgagtgttt aagagagtta catacccaaa acagaaatgt gggaccgttg atcatcacac    2400
caattcaatt tattcagacg ctcgctttgt ggtaattggc ctataaattg tatcccaaac    2460
ttcagttaga caacaaaagc acttgttcac caattaagct ttcaagagac aaactgcttt    2520
gaaaaatggg atccaaggtt gttgcatccg ttgcccttct cctctccatc aacattcttt    2580
tcatttccat ggttagctcc agcagccact acgatccaca gccccaacct tctcacgtca    2640
ctgctcttat tacacgacct agttgtccgg atctgagtat ttgcctcaat attttaggcg    2700
ggtctctagg aaccgtggat gattgttgtg ccctcatcgg tggtcttggt gacattgaag    2760
ccattgtgtg cctttgcatc caactcaggg ccctcggaat attaaacctt aaccgtaatt    2820
tgcagttaat attaaactcc tgtggacgaa gctacccgtc aaacgccact tgcccccgaa    2880
cctaagaaca gaatatgtat ggcactaatt accatattac ttcgtatcat ggtgtttgtt    2940
tgtttgtctg tgtttaaagt taaggatgtt atacccttcg tgcctgctac atatatatag    3000
tgggcactat aatattacca ataaattaac gtccatatat aagaataata ataaataaat    3060
aaatatttct atacaaataa aggttacgta atgttgttgt tctcgtggat ggggatctta    3120
tcttcctcct cgctatcttt gtttatcgta tttcagtgaa agttgttcaa taaaagtcct    3180
ttgttcaaca agtgattcct tctctctctg tctttcttt cactttcgta ttttctttag    3240
gtataaggtg gcaaaatag acaggaatat cgatcttgtg ataaaattaa aatcggtttg    3300
ctgatgtttt aattagttag aaaaaagaag acatatattt atcgtaattc ctgttcatga    3360
ttataaga                                                            3368
```

<210> SEQ ID NO 8
<211> LENGTH: 7235
<212> TYPE: DNA
<213> ORGANISM: Glycine max

<400> SEQUENCE: 8

```
gtcgactcga tctcaaattt tatttcattt aaaataaaac ataatttaat tttcgtctct      60
cttccttatt gtatcattat aaaagtagga aacaaatat aaattagaac aaacataata    120
ttaattaata agaataatt gtttgttgct ttgaattttc tattctaata acattaggta    180
```

-continued

```
gtaataaaat taagttgagt ttcattttt tgaaagaatt aacttaataa ttgtatattt      240
ttgtttaagt ataatatttt agataatgta ttatcacatt aaaaatttag agtgatagac      300
aaattatgtt tattaatcaa tattatgttt atttaattgt ttgttttaag ttaggtttgt      360
tttcatattt tttttagtgt ttttattata atgagaaaaa aaatggagga taaaagataa      420
aaattatatt atattttact cttaaataaa acaaaatttg gagtcctaaa aattagttta      480
atgaaaactt gttgacatag gtctaatcta ttcaataatc atgttagctt atttgtgctc      540
ttggactcct tcattaacgg taatagatga atgaatttat tgcatttctt tcacttttga      600
ttactaaaat ttaaattttc attttcgaa atgaattcg ttactatttt atacatttaa       660
aaataaaaat gattatttca tcttataatt atcaaataat atgcctgtga tgatgatttt     720
tttcaaaaat tgaaaatgtc ttattgccta gttaggctat agaatctttt tggctcatct     780
caatcgcatg gcgacatggt taccgcgttc attgggtaat tatatttatg tatttaaatt     840
aattctatta aaccaattc tattaaagct gaaaactaaa atgacactta atttctgtaa      900
gagtcgtgta attagcgagc cagagtaatg caaccaaaga gcttcttttcc ccaccttaat    960 tcctttataa tgaatttgat tgataccata catagctaag ctttttttc tttcgattta     1020 catagccaag ctttagctgc tatatataat atgttgttta taaattttg acatgttgca    1080 ttacatgtta ctaactggtt gcaacctcca gttttggtta tcgaatatat gctggccggc    1140
accaactaca aaaatttct gtatggctgg ctactaatac tatatcttca aatgtctcac     1200
tttacatgga ctgagtgcat aacgggcaat tgcagtgctc ataaggaata cgcatgcaat    1260
cattttatca tcgcagattg ttgcttttcc ttcactgtaa aaaaaataa aaataacaat     1320 taattgagca ccgaatgaac tagaccgatt gcatgcatta taatacatga agaaaattat    1380
ttatactaat cttttgtttc aagttttaaa gttgacttttt ttgttttaca agcacaataa   1440
caatcaaata accataatt taatcattaa aaagataaac aaactcatta gataaaataa     1500
taattatgat aaaatatgtt taagtcctct atatttaagt tgaattttgt ttttagtctt    1560
tcaaattgtg catttagtc tctgaaattt tattttaaaa aaatagtctt tgggcttact     1620
ctccaaaatt tgcacatttt aattttaggt tattgattaa agattaaaaa cattttttt    1680 tatcaaattt agggaccaaa ttacttgata taaatactca agaactaaaa acaaatttca    1740
ataaaaatat aagggattaa aaatatattt tattctgata actaacaatc atcaaatttt   1800 atgcaatca tatgtaacct tttataatat aattgtaaga ataattaatt ttaataaata    1860
aataaataaa tgagacttat aatagtaaat acatatgttt gcctaggtaa taacaatgat    1920
aacaagtaat agaattatca ttcttattgt atctattaat taatatatta ttagatgtat   1980
taattagtat atatatttt tactataaat agtatatatt attaattatt atacatttat    2040
taaagtatat tcattaaaga ttttgaggga ggggagctga agccactaac ccccgtaaat    2100
ccgtccttgc acaaaacacg acatgagaat ggttttgtat actccacaat ttaatatcca    2160
ataaaataat ttcttttta ttttaattag gaaactccaa gattgcttta acttatacaa     2220
aatctgaata acacaaaaaa ataaaaaatc ggaattaaat gttgcccgat tgttgactaa    2280
cttatacaaa atcttattta aatgcttaaa atcgtgtcat aatataatga atatatattt    2340
gcaaatatat atttattata taattgcaaa tatatattct aattttgagt ataaataaca    2400
gcatgtgagg gtgcagcaaa acacacactg agtgcaacaa agttttaaca tgaaaggcaa    2460
taatacactt ttgttgcatt tattctacac tactctcttc ctgtttcttg tagtgtcaag    2520
```

```
ttcatcttca acagggaatg aaagtaacga tgacactaac agtaaagaag tttatatcgt    2580
gtacatggga gctgcagatt caacaaaagc ttctcttaaa aatgagcacg ctcagattct    2640
gaattcagtg ctaagaaggt acgtataatt acataatatt attattatat gggcaccaat    2700
taattaattt gatgattgat gtgtttacat attttgtgtg aatgaattga aggaatgaga    2760
atgccctagt acggaactac aagcatggtt tctctgggtt cgcagctcgt ctatcaaaag    2820
aggaggcaaa ctcaattgct cagaaacctg gtgtggtgtc tgttttccct gaccccattc    2880
tgaagctcca cactcacgt tcatgggatt tcctcaaaag ccaaactcgt gtcaatatcg    2940
acaccaaacc aaatacgctg tccggttctt ctttttcttc atcagacgtc attcttggcg    3000
tcttagacac aggttgtcca taatcaaaaa aaaaaaaaaa acatgatata tatgtgtgtg    3060
tttcattttt taaaaatgtt aataataata tatacaaaaa tggaatattt caggcatatg    3120
gccagaggcg gcgagtttta gcgacaaggg tttcggtcct gttccatccc gatggaaagg    3180
cacctgcatg acatcaaaag acttcaattc ctcttgttgt aacaggtaaa ctaaaatgtg    3240
aaaccataat aataataata ataataataa taaatatata aaggcgaacg ttattaatta    3300
ttaattatta ttagaaaaaa ggtgatttca gcttgctgtt taagaaggtt tggaatgaat    3360
cctatttaat taggtagtgg atggaataac ggttaggttt gtatttatag gaagataatt    3420
ggcgcgaggt tttaccctaa cccagaggag aaaacggcaa gggatttcaa cggacatggg    3480
actcacgttt cgtcgacggc agtgggcgtg ccggtgagtg gcgcatcgtt ctatggtctg    3540
gcggcgggga cggcaagggg tgggtcccct gagtcaaggt tggcggttta caaagtgtgt    3600
ggggcttttg ggtcatgtcc tgggtcggcc attcttgcgg ggtttgacga tgccattcac    3660
gacggagtgg atatcttgtc gctgtcgctc ggtggattcg gtggaaccaa aaccgatttg    3720
accaccgacc cgattgcgat tggagcattc cactccgtcc agcgcggcat cctggtggtc    3780
tgcgccgccg ggaacgacgg agaaccattc accgttctca acgacgcacc ttggatttta    3840
accgttgcag cttccaccat cgaccgtgat cttcaatccg acgtggtctt gggtaataac    3900
caagtcgtca aggtacctac atattctact ttaaatcggt gcagtgcaac taatgtcatc    3960
ttttctcatc gttgataatt attaaacttc agggaagagc cataaatttc tcccctcttt    4020
taaattctcc cgattatcca atgatatatg ctgagtctgc tgccagggca aatatctcca    4080
acataactga tgcaaggtac gtactctaaa aaccatttgt cgtttcgtat tggacaaact    4140
tcaaatcaag caatcaacta agcaataaca aacaagtgtt tcatcaccaa tttatatgtaa    4200
tactcatata taacctctta gcaaatgatt aaatcatttg tcacatgcag acaatgccac    4260
ccagattcat tagatccaaa aaagtcata gggaagattg tggtttgtga tggaaaaaat    4320
gacatttatt attcaactga tgagaaaatt gtcatagtga aggcgttggg aggaataggt    4380
ctggttcata ttactgatca atctggatca gtagcatttt attatgtgga cttcccagta    4440
acagaggtaa aatcaaaaca tggcgacgca atcctccagt acatcaactc aactaggtaa    4500
ggatattata tagcacttga agaagcaac attcttgatt aattttagaa tttgctttga    4560
tcacgagtta ttttctttta attctttgtg catatatgta atataaagcc atccagtggg    4620
aacaatacta gcaacagtta caattcctga ttataagcct gctccccggg tgggttattt    4680
ttcatcaaga gggccttcat tgattacaag caatgttctc aaggtatgat atgacgatcg    4740
atagaattat acatatcaat catcatcctc aatatgctca ttgctcaaac actaaacaga    4800
acattcattc tttctttctt tctttctttc tagcctgata ttgcagcccc gggagttaac    4860
attctcgctg catggtttgg aaatgacaca tcagaggttc caaaaggaag aaagccctca    4920
```

```
ctatatcgca tactctcagg aacttccatg gctactccac atgtttcagg gcttgcatgc    4980
agtgtcaaaa gaaaaaaccc cacttggagt gcctccgcaa tcaaatctgc catcatgact    5040
tcaggtcacc catttgataa tgtgatctaa gtaagtaatg tgatccagca aaatgtacca    5100
taccaactca tatcattcta taaattaata tgtatgcagc aattcaaaat gacaatttga    5160
agggtcccat aacaacggat tcagggttga tagccacacc ttatgactat ggagcagggg    5220
caattacaac atctgaacca ttgcaaccgg ggctagttta tgaaaccaac aacgttgact    5280
acttgaacta tttgtgttac aatggactta acataaccat gataaaggtc atctccggaa    5340
ctgtccccga gaatttcaat tgtcccaagg attcgagctc tgatctcatc tccagcatca    5400
actacccttc catagcagta aacttcactg gcaaagcaga cgcggtcgtg agtagaactg    5460
tcacaaacgt tgacgaagaa gatgaaacag tgtacttccc cgttgttgaa gctcctagtg    5520
aagtaattgt cacactcttt ccatataatc ttgagtttac gacaagtatt aaaaaacaaa    5580
gctacaatat tactttcaga ccgaagacct ccttgaagaa agatttgttt ggatctatca    5640
cttggagtaa cgacaaatat atggttcgaa ttccttttgt attaactaaa tagtgaaatt    5700
aaaaagtagc gatgaataaa tgcaagctaa gttcttcgtg gtgcctacac tcgagtcctg    5760
attatttatt attcatatgc cttctgtttt aatttaattt attatacttt cagcctctct    5820
aatatgtttt tttcttttgc aaatatataa gctgacttac tatttacact caaaattagt    5880
tccaacttat tcactagccg tttgccctca gcttaattaa aaaaaagaaa tgtgatttaa    5940
ttacattaat tatagctgga tcgtagtaac ctcggatttt tacacgggtt ggtaattcaa    6000
catcaatttc atgcttcaaa tgcaaactcc tcaaaagtag ttgcagacta aaatgatgaa    6060
tttttaacaa aacttgtaca aaggtaaggg ggaactaggg aagtgagctc ataaaataag    6120
gaaactgttt cgactgagtt ttgagtaagg tgtggctgaa ttttggcttg agttgtggtg    6180
agctgtagca gagtttcgac tttgttgtgg taagctatga cttagttttg acgaattgtg    6240
gtgagttgtg gtcgaatgga atcttggatc tcctaatccg gtgtaggaga agtacctaca    6300 aaaggactc caacaatcaa ctcaattgga tccgagatac ttatgtatcg atgtatgaaa    6360
tgattaaaac ataccttgtt gtgttttatt tatgtcaata tatacatatt cgacattaag    6420
gaggttacac taactagata gtcctctaag cgttgcgtga tcgtgaaaag ttagtgatca    6480
tcactatcga gttcataggt tgtacggtac ataaatccca ctaatcgagt aactatcaag    6540
ttcatggggg ttgtacggta cataagtctg tcagattccc atgatgggta ttgctaagtt    6600
gaataaatcg ggcatataca ttacacgagt ttaagatgat ttaattttcc ttatatatca    6660
ttattttata ctgggtgagt gttttctttg aaaaactgag gtgtggatcc aacctcttga    6720
gaagtgcttt taaaaaaatg aggtttggat cctatctctt gagaggtgct tgaaaaagct    6780
tatcaaaata gttattggca ttcaatgttg ttttcaaccg agggcaatta aacacacctt    6840
tgattagtgg gcaattgaag ttagaaagaa gcttataaag gatagtatta ttatactatt    6900
acaaccaagc aaacaatgtt tacttcaaag ttgataccct attgatataa tgtattattt    6960
actatgagtt aaaatgtaat ttgaaaaaaa aaatgtaact gaaaatgttc ggatgatttt    7020 catatttgt aaaaaaaaaa aaaaagaaa aaaagttat taggctaatt tttgcaaagt     7080
acattttggt atgaaaaacc aaaaacagaa gtaatgcatt ttgtgccatg gcagaatgca    7140
gagtatctac ccaggattca ttatgaacaa cttaatgcta agcatcatca gttaaccccc    7200
caaattaatc ttgaaagcta caattctatt ctaga                              7235
```

<210> SEQ ID NO 9
<211> LENGTH: 8310
<212> TYPE: DNA
<213> ORGANISM: Glycine max

<400> SEQUENCE: 9

| | | | | | | |
|---|---|---|---|---|---|---|
| gagctccgcg | aaatttgtta | tggccatact | cttccttgcg | agccctcttg | gtctcttgtt | 60 |
| caagggctct | tgcggtagtt | gcattctctt | cccgtaattt | ggcacactcc | ttccggatgt | 120 |
| gtgtagcggc | taacttgaac | ttctccttgg | caagtttcgc | ctttcctaac | tcgttttttga | 180 |
| gagcttggac | ttcttcgtct | tcttccggtg | cttcgaaact | gtctttgctg | acgacttta | 240 |
| acttggcgag | ccaatctaaa | cctcgtattt | gaactttcag | ccattcatga | taaccaccaa | 300 |
| tgatgccatt | acgaatgccc | ctaagttctt | gatctttcct | taacgggtt | tcccatgcct | 360 |
| tatggattct | ttgtatagcc | ttgaaatttt | gcatgccgaa | atctctcaca | aggaaaggag | 420 |
| aaatccttc | ttccatcggt | gttcccctca | tggggtaccc | tagttgtctt | atagcgagcg | 480 |
| cgggattgta | gttgatacaa | cccctcgttc | ttatcagtgg | aatgtttggg | taccctccac | 540 |
| atgagaaaag | gactccctcc | tttccttcct | tccatcgggg | gaaccaacta | attgttctac | 600 |
| ctcctatctc | ggccaagagt | tggtcccaat | ctattcctct | cttttcagca | cacgagtgat | 660 |
| ggctttggag | cggacatgga | tgcctcgtgt | tttgctggaa | caggtgtgaa | accaaccaaa | 720 |
| cacagagagc | gggcaagcaa | cagatgatcc | atgcgctact | cttctcgcac | cttcggtcaa | 780 |
| atgtgtcaaa | taaatctgcc | aagacagcta | ccaccgggct | ttcctgtttg | gaaagaggac | 840 |
| gaccccaaag | attagcaatg | ctaacacatc | cataaacggg | acccaatctt | cttgatttgc | 900 |
| catatccctc | gccttgtctt | ctaggtactt | ccgtggtagg | cccgctatgc | cgtttcgagt | 960 |
| ttgttttacg | cggtccaaac | tcttgctga | atctttgacc | acggtcgcaa | ttctgctcaa | 1020 |
| agaggggaga | cacccggaga | aaagatatga | ttttcttccc | ccgagaggac | atcctagaat | 1080 |
| ctcctcaaat | tcttcaatgg | tcggtaccaa | ttggaagtct | ccgaacgtga | agcatctcaa | 1140 |
| aggctggtcg | tagtattggg | tgagtgacgc | aatggcctct | atggatacct | ctggtatggt | 1200 |
| caaatctaag | atcgatcttg | gattgttgtt | ggttttgttg | aagtattttc | taaccttttg | 1260 |
| aatatgttac | taatgtcaaa | tttattattt | gttataaaat | ctttttgtct | gggtttattt | 1320 |
| tctagggttt | tctttaattt | ttccagaaaa | actttctttt | cctggggatc | aggtatagaa | 1380 |
| ttgattgcct | caaacaagag | atcgatctct | ccgaaattgc | acacagtggt | caatgtctca | 1440 |
| gcatatctgt | tttatagttg | tggattctat | aagtcaattt | agattattgt | taattaccta | 1500 |
| agttattgtt | ttaaattcat | acataattaa | ctttgtctta | acaacaacag | acatctgact | 1560 |
| gagacaagta | tgtgagcggg | gaattctgat | gtgtatggat | tcctcgagcc | acagtctatt | 1620 |
| cagagatctg | ggcaatcgca | gtttgaatca | gaaagttaca | tcaagagttg | gatgcagagt | 1680 |
| tcaaaacgcg | atgtctacct | tggagcctac | ctgaatggga | aagtcaaata | aaacaactaa | 1740 |
| atttaaataa | tatataatac | tacaataacc | catattcatc | tccactgcag | cggacacagg | 1800 |
| aaaatggtct | ttattctgcc | taaggaaaac | cttgttgtct | ggttttgttc | cttgcataac | 1860 |
| aggtcagaca | actaccttaa | gggaataatt | aacaggtcag | tgttgttttt | aatacatttg | 1920 |
| cattagcata | actcaacaac | atcaatattt | taatgttcct | cgtattcaac | agtgctttga | 1980 |
| aaggacttga | tgatactcca | caatctaaat | ccaaggctgg | tgctaggtgg | atcgttgtta | 2040 |
| aggtacgtga | tttaaataaa | acttctactt | atatatactg | cttatgtgtg | tgtacactaa | 2100 |
| ttgtagttaa | cgtttaatta | atatccaaat | ttcattatgt | atttagtgta | atagacaaaa | 2160 |

```
aggaagcact gagtgcggct attacatcat acactagatg tccatgataa tcttaggaac    2220
ttttaggaat aattgggaaa ccgtaattgt ttatttcaaa caaagtttat tttcttgtca    2280
ttggtattac attattaact tatgttttat ttgatcatgc agtattttaa cgatgttaaa    2340
ccattggaag caaagagatt gaaggtgctt cgcatccagt gggcacaatt ttatctcaaa    2400
gttacaaatc aaagttagga tgttagggaa ctatttcatt ttaggttact taattagttt    2460
actaccttgt tttacatttt tgccaattgc tatgccattt gaacattgaa tattcttaat    2520
tgatagttat taataaatca tttattcata gttatcaatt gatagtttac tatagcttta    2580
tactaaaaac cgtttaaaag cagaatgcaa atgatatatg ctgtgatcta tggtctgatt    2640
tcaattttac aggttcaatt ttgagttttt ttgtaaaaac aaaagtgta ttaaaaaaaa     2700 ctaaaaacaa aatcggtttt ttacaaaaat cgatgttaac atacaactta acatcggttt    2760
ctcaaaaaac cgatgtttgt gtatattaac attgattttt gtaaaaaacc aatattaacc    2820
tatgaaaatt taacattggt ttttatacaa aaccgatgtt aacttataga ttaacatcag    2880
ttttgtataa aaacttatgt taacgtttct aacttaacat caattttat agaaaaccga     2940 tgttaatata tgagttaaca tcgattttga tacaaaactg atgttaatct ataagctaac    3000
atcggttttg tagataaccg atattttaaa ttttacgtta aactgatgtt aacgataata    3060
ctttcaacat cgattaaaaa tcgatgtaga aagtcgtaaa taaccgatgt agaaaatcta    3120
ttttctaata gtgtccatct caatatatgt ttggatagtg tcggcattac cctggtttga    3180
ctaatgcttt tgcactcaaa ttgtcacacc ataaaatcgg tgttctgaga atgggcaagc    3240
taatcttctt gatccattga gaacctaatt ttcattattt ttttacctaa acataaaaac    3300 acaaaatat aagaaaataa aataaaatcc ttatctaaat tcagaacata aaataaataa    3360
catctttcat gttaatattt taaaattcat tattttgaag ccaaatgggt taaaattta     3420 taacaagtga cttaaaatta aaatttccaa aaataagtag aaaattagat aatttaaaaa    3480
ttaccaaact cattttatcc ttcatgactg ttatgtactg atgcagtgta attacccaca    3540
ttataaatgg taattacaaa ctagtactac cttataaatt aattacccc attctcctat      3600 cttacaaata aaattaaaaa tacggacaaa catggcagtg gtgtggtttc gctttaaaaa    3660
taaaaatata caaacatgaa agtgatgtgt tttcgttgtt atatataata atgctcacga    3720
tcgagactca actaaatgat cacgcaaatg ttttctttag gatgaagcct gttgctaatt    3780
tcttcatctc aaaatccggt cattacgcaa tttatagatt tgtcgagatt ttggcttctt    3840 ctttaaatt gcgcataaaa acttatcaat gtataccta tggctgcatg aaattaccta    3900
ttcttatggt tgcatattaa atgttcatac tttttatatt attttatta gattaaattg      3960 taattttgat ccctatttt aaattaaggc attccattaa tggaccattt atgtgacaaa     4020
agattaaata acttaaaaat acaaaaaggt cttagtataa attaaattta aaatatttta    4080
tataaagata aaataataaa accataaaat acttacttta tttagttaat tttataaata    4140 ctatttttaca tgtatcatta attagtccag aattattaat ttttttaatt ataaaaattt   4200
ataaattgaa ataaaatatt taatatttaa atatatttaa catttaattt tacatgtact    4260 tattttctt ataaaatttt attttaaaat aaatcaacta aaatttgttg ttattttagt     4320
ataattttaa aaaaatacat aaactaatat atagattatt ttaaaattat ttatctaat     4380 ttatgaaaat taagtagatt taaaataaca tttaactaat ctaaaattta aaatttatta    4440
cttgttataa ttaaaataaa cttttcatt atttatatat aaaaataaat gtagataatt     4500
```

```
ttatcaatta cataaaataa tttatatata actaatttac atattaatttt atttaatttt   4560 cctcatttat ataattgata ttgaaaaact tatttactaa atatttttta tagttaaaat   4620
aaaaatatta acatgttttt ttcctaaaaa cattaaatat tcaaatttta ttcatttatt   4680
taattaaaat aaaggtaatt tacatattaa aataaattac ataatttgta taatttatat   4740
attaataaaa aaatatataa attaatttaa attagtcaaa taaaaataaa aatatataaa   4800
ctattcaata tatatatata tatatatata tatatatata tatatatata taatataatg   4860
acatacaaga aaattaaaag gatttataaa aaggatttat atattaaata tttttttaatt  4920 cataaatttt tataatttaa aaaattaact catacataaa taatatttaa aaaattagtt   4980
aaaaaaataa atatcttaat agtttgttat tttaattta aataagagat tataagttta    5040
attcttatta tttttttca taattttaac tcttaccaag tattttttc actttgttta    5100 atctctattc tctctctctt tatatatata tatatatata tatataataa atttctaatc   5160 aactaaaatag tgtatatttt acatgcagag tacataaaaa ttaaaattgg gtataatagt   5220
tattgtacgt catctcactc actcttcctc ttagagtcta tatatatgca atatctctgg   5280
tctccctatc accttctctt ctctaagcac tttactttt ttttcagcca tggagtttca    5340
ttgccttcca atatttcttt atctcaatgt gagcataaac cttccttttt catctcgttt   5400
tttaacctgt attgcgtgaa gttggatttc ttcattaatt atcatttta ttatagcaat    5460 aagtatcaag tgatgggttt tgcatgaat tatgtagttg atgttgatga cagccaatgc    5520
tgcgttaact cctagacatt actgggaaac gatgcttcca agaactccct tgccgaaagc   5580
aatcacagag ctactaagcc ttggtgagta agaaatcaaa ttgaaataaa ataagcaaca   5640
cttttgtaat taaatctgaa acgataaatg tacgtaaaca aaaatagaa ttagaaacca    5700 atgcaaacag ctataagcct ttttttgtaa tagctaatct gccttaatta aaccattgaa   5760
tgactcaata tgttcatctt tttttccttt tagtagaata ctgcccttct tcatattcga   5820
tatactattg gcttccttag tgaattctta ttctaatggt tgcatagctg tgttctcact   5880
aagcctcctt tcccatgtct ttgattctat gaaacgaaac tttcaaaact tggaatcacc   5940
tattaagtac aataaagaaa taattaattt tatttttatc ctttaattat tttatgaatt   6000
tggttccttt attttatttg atatattttt tacaaatttg gttttctcat tatttttaatt   6060 gtttattttt tgttcatctc ttaacttaat atccaacatt tcataaatat gctgacataa   6120
tactagatta ttatatcacc tgtgggata ttcatgttgc acaattagtg gaggctcaaa    6180
ttcgtgaaaa aataaataaa atttggagag accatattca ccaaatcaga atagtataca   6240
gagacaaaaa aaaaaaaaaa aaacaaatta tgcaacgaat gaaaagttaa ccattatatt   6300
tagtattgag taatttgaag tcagtgtgag acatggcaac gtagttaact tactttaatt   6360
aaaaatatga ataattaaaa taggaatata taacggattc ggattctctc cagcaatgat   6420
gaggacgtag gattaatttt atggctgaga gtaaatccaa aaagatacgc aaaccacgta   6480
tcaccgctac tgcttgacca aatggaagcg acttcaaacc aaaattagga caaagaaaat   6540
aaaaatacaa atgtcaataa actcaatata caaagacaga gtgtaagttt tactaaatgg   6600
aaagctggaa ttgaagtaaa agctttacat atatattgct tgctaaacaa ttttgaattt   6660
ttttatcttt ggattcttgc taaacaatta attatatcta ttaatatttc tctaataata   6720
tgggatacac ttattattat tattattatt attattatta ttattattat tatttgatttt  6780 aaatataatt ttgatatttg actaatatta aattatttt aaacaatcac aaatttcgaa    6840
taattaatga taatattaag ttatttttcat atttgactag tatcaaaaag ttatttacac   6900
```

-continued

```
atttgactta ctgttatttt attttagttc tctagttttt aaaagtataa taagttagtt      6960
cttttcatttc ttttctattt tccatttttaa ttaaaaaaaa ttcaattttt attttatttt    7020
gtaacaatgg gctgaaaata gctactaaaa ttttggctgt gttttctttt accaatcaga      7080
aagtaggtcc atatttgaat atgccgggaa tgatgaccag tcagaaagta ggtccatatt      7140
aggatacgct ggctataatc aagacgagga tgatgtgagc aaacacaata tacaaatctt      7200
caacaggttg tttttcttgg aagaggacct gcgtgctggc aaaatattca acatgaagtt      7260
cgtcaacaac acaaaagcca cagtcccgtt gctaccgcgc caaatttcga acaaataccc     7320
gttctcagaa gataaaaaga agcaagtgtt ggcgatgctt ggcgtggaag cgaactcaag      7380
caacgccaag atcatagcgg agaccattgg tctttgccaa gagcctgcaa cggagggaga      7440
aaggaaacac tgcgcgactt cgttggagtc catggttgat ttcgtcgttt ccgcgctcgg      7500
gaagaacgtt ggtgctttct caacagagaa agaaagggaa actgagtctg aaagtttgt      7560
agtggtgaaa atgggggtga ggaagttggg agatgataag gttattgcct gtcatccaat     7620
gagttaccct tatgttgtgt ttgggtgtca tctagtgcca aggagtagcg ggtatttggt     7680
gcgcttgaag ggagaagatg gggttcgagt gaaagcagtt gttgcgtgcc acagagacac    7740
gtcaaagtgg gaccataatc atggggcatt caaagtgctc aatcttaagc ctgggaatgg     7800
tacagtatgc catgtcttca ctgagggaa tcttctttgg cttccaaatt agattaatta     7860
ccatatacat atttgtcctt gttctatcct taaataagtg gaatcacctg aagaattgtg     7920
cgtaatgagt tgtttgtctt tgtggaaatt gttatctgtc ttgcatcacc aaataggtat     7980
atataaaata acaggagcgt ggtatttgtt gcacaaaaat ggatttcaac cgatcaaaaa     8040
aatatagcct ttaccaatta gaagggtttg gctttgttag caaataataa aaataaaata     8100
tcttgatgga taaatggttg ctaagttgat taagattgtg gcagaatacc aagtcaatga     8160
atagtccatc acaagcatca aaagaaaaga taatgattcc ttgaaaatag aaagcacttt     8220
gtgttttgaa ttcaaaatgc acactggaga gttgttggag gttacaagcc agatcgagtc     8280
gactcccttt agtgagggtt aattgagctc                                       8310
```

<210> SEQ ID NO 10
<211> LENGTH: 119
<212> TYPE: PRT
<213> ORGANISM: Glycine max

<400> SEQUENCE: 10

```
Met Gly Ser Lys Val Val Ala Ser Val Ala Leu Leu Leu Ser Ile Asn
 1               5                  10                  15

Ile Leu Phe Ile Ser Met Val Ser Ser Ser His Tyr Asp Pro Gln
                20                  25                  30

Pro Gln Pro Ser His Val Thr Ala Leu Ile Thr Arg Pro Ser Cys Pro
            35                  40                  45

Asp Leu Ser Ile Cys Leu Asn Ile Leu Gly Gly Ser Leu Gly Thr Val
        50                  55                  60

Asp Asp Cys Cys Ala Leu Ile Gly Gly Leu Gly Asp Ile Glu Ala Ile
 65                  70                  75                  80

Val Cys Leu Cys Ile Gln Leu Arg Ala Leu Gly Ile Leu Asn Leu Asn
                85                  90                  95

Arg Asn Leu Gln Leu Ile Leu Asn Ser Cys Gly Arg Ser Tyr Pro Ser
                100                 105                 110

Asn Ala Thr Cys Pro Arg Thr
            115
```

<210> SEQ ID NO 11
<211> LENGTH: 286
<212> TYPE: PRT
<213> ORGANISM: Glycine max

<400> SEQUENCE: 11

```
Asn Ala Ala Leu Thr Pro Arg His Tyr Trp Glu Thr Met Leu Pro Arg
  1               5                  10                  15

Thr Pro Leu Pro Lys Ala Ile Thr Glu Leu Leu Ser Leu Glu Ser Arg
             20                  25                  30

Ser Ile Phe Glu Tyr Ala Gly Asn Asp Asp Gln Ser Glu Ser Arg Ser
         35                  40                  45

Ile Leu Gly Tyr Ala Gly Tyr Asn Gln Asp Glu Asp Val Ser Lys
     50                  55                  60

His Asn Ile Gln Ile Phe Asn Arg Leu Phe Phe Leu Glu Glu Asp Leu
 65                  70                  75                  80

Arg Ala Gly Lys Ile Phe Asn Met Lys Phe Val Asn Asn Thr Lys Ala
                 85                  90                  95

Thr Val Pro Leu Leu Pro Arg Gln Ile Ser Lys Gln Ile Pro Phe Ser
            100                 105                 110

Glu Asp Lys Lys Lys Gln Val Leu Ala Met Leu Gly Val Glu Ala Asn
        115                 120                 125

Ser Ser Asn Ala Lys Ile Ile Ala Glu Thr Ile Gly Leu Cys Gln Glu
    130                 135                 140

Pro Ala Thr Glu Gly Glu Arg Lys His Cys Ala Thr Ser Leu Glu Ser
145                 150                 155                 160

Met Val Asp Phe Val Val Ser Ala Leu Gly Lys Asn Val Gly Ala Phe
                165                 170                 175

Ser Thr Glu Lys Glu Arg Glu Thr Glu Ser Gly Lys Phe Val Val Val
            180                 185                 190

Lys Asn Gly Val Arg Lys Leu Gly Asp Asp Lys Val Ile Ala Cys His
        195                 200                 205

Pro Met Ser Tyr Pro Tyr Val Val Phe Gly Cys His Leu Val Pro Arg
    210                 215                 220

Ser Ser Gly Tyr Leu Val Arg Leu Lys Gly Glu Asp Gly Val Arg Val
225                 230                 235                 240

Lys Ala Val Val Ala Cys His Arg Asp Thr Ser Lys Trp Asp His Asn
                245                 250                 255

His Gly Ala Phe Lys Val Leu Asn Leu Lys Pro Gly Asn Gly Thr Val
            260                 265                 270

Cys His Val Phe Thr Glu Gly Asn Leu Leu Trp Leu Pro Asn
        275                 280                 285
```

<210> SEQ ID NO 12
<211> LENGTH: 770
<212> TYPE: PRT
<213> ORGANISM: Glycine max

<400> SEQUENCE: 12

```
Met Lys Gly Asn Asn Thr Leu Leu His Leu Phe Tyr Thr Thr Leu
  1               5                  10                  15

Phe Leu Phe Leu Val Val Ser Ser Ser Ser Thr Gly Asn Glu Ser
             20                  25                  30

Asn Asp Asp Thr Asn Ser Lys Glu Val Tyr Ile Val Tyr Met Gly Ala
```

```
                35                  40                  45
Ala Asp Ser Thr Lys Ala Ser Leu Lys Asn Glu His Ala Gln Ile Leu
 50                  55                  60

Asn Ser Val Leu Arg Arg Asn Glu Asn Ala Leu Val Arg Asn Tyr Lys
 65                  70                  75                  80

His Gly Phe Ser Gly Phe Ala Ala Arg Leu Ser Lys Glu Glu Ala Asn
                 85                  90                  95

Ser Ile Ala Gln Lys Pro Gly Val Val Ser Val Phe Pro Asp Pro Ile
                100                 105                 110

Leu Lys Leu His Thr Thr Arg Ser Trp Asp Phe Leu Lys Ser Gln Thr
                115                 120                 125

Arg Val Asn Ile Asp Thr Lys Pro Asn Thr Leu Ser Gly Ser Ser Phe
130                 135                 140

Ser Ser Ser Asp Val Ile Leu Gly Val Leu Asp Thr Gly Ile Trp Pro
145                 150                 155                 160

Glu Ala Ala Ser Phe Ser Asp Lys Gly Phe Gly Pro Val Pro Ser Arg
                165                 170                 175

Trp Lys Gly Thr Cys Met Thr Ser Lys Asp Phe Asn Ser Ser Cys Cys
                180                 185                 190

Asn Arg Lys Ile Ile Gly Ala Arg Phe Tyr Pro Asn Pro Glu Glu Lys
                195                 200                 205

Thr Ala Arg Asp Phe Asn Gly His Gly Thr His Val Ser Ser Thr Ala
                210                 215                 220

Val Gly Val Pro Val Ser Gly Ala Ser Phe Tyr Gly Leu Ala Ala Gly
225                 230                 235                 240

Thr Ala Arg Gly Gly Ser Pro Glu Ser Arg Leu Ala Val Tyr Lys Val
                245                 250                 255

Cys Gly Ala Phe Gly Ser Cys Pro Gly Ser Ala Ile Leu Ala Gly Phe
                260                 265                 270

Asp Asp Ala Ile His Asp Gly Val Asp Ile Leu Ser Leu Ser Leu Gly
                275                 280                 285

Gly Phe Gly Gly Thr Lys Thr Asp Leu Thr Thr Asp Pro Ile Ala Ile
290                 295                 300

Gly Ala Phe His Ser Val Gln Arg Gly Ile Leu Val Val Cys Ala Ala
305                 310                 315                 320

Gly Asn Asp Gly Glu Pro Phe Thr Val Leu Asn Asp Ala Pro Trp Ile
                325                 330                 335

Leu Thr Val Ala Ala Ser Thr Ile Asp Arg Asp Leu Gln Ser Asp Val
                340                 345                 350

Val Leu Gly Asn Asn Gln Val Val Lys Gly Arg Ala Ile Asn Phe Ser
                355                 360                 365

Pro Leu Leu Asn Ser Pro Asp Tyr Pro Met Ile Tyr Ala Glu Ser Ala
370                 375                 380

Ala Arg Ala Asn Ile Ser Asn Ile Thr Asp Ala Arg Gln Cys His Pro
385                 390                 395                 400

Asp Ser Leu Asp Pro Lys Lys Val Ile Gly Lys Ile Val Val Cys Asp
                405                 410                 415

Gly Lys Asn Asp Ile Tyr Tyr Ser Thr Asp Glu Lys Ile Val Ile Val
                420                 425                 430

Lys Ala Leu Gly Gly Ile Gly Leu Val His Ile Thr Asp Gln Ser Gly
                435                 440                 445

Ser Val Ala Phe Tyr Tyr Val Asp Phe Pro Val Thr Glu Val Lys Ser
            450                 455                 460
```

-continued

```
Lys His Gly Asp Ala Ile Leu Gln Tyr Ile Asn Ser Thr Ser His Pro
465                 470                 475                 480

Val Gly Thr Ile Leu Ala Thr Val Thr Ile Pro Asp Tyr Lys Pro Ala
                485                 490                 495

Pro Arg Val Gly Tyr Phe Ser Ser Arg Gly Pro Ser Leu Ile Thr Ser
                500                 505                 510

Asn Val Leu Lys Pro Asp Ile Ala Ala Pro Gly Val Asn Ile Leu Ala
            515                 520                 525

Ala Trp Phe Gly Asn Asp Thr Ser Glu Val Pro Lys Gly Arg Lys Pro
        530                 535                 540

Ser Leu Tyr Arg Ile Leu Ser Gly Thr Ser Met Ala Thr Pro His Val
545                 550                 555                 560

Ser Gly Leu Ala Cys Ser Val Lys Arg Lys Asn Pro Thr Trp Ser Ala
                565                 570                 575

Ser Ala Ile Lys Ser Ala Ile Met Thr Ser Ala Ile Gln Asn Asp Asn
                580                 585                 590

Leu Lys Gly Pro Ile Thr Thr Asp Ser Gly Leu Ile Ala Thr Pro Tyr
            595                 600                 605

Asp Tyr Gly Ala Gly Ala Ile Thr Thr Ser Glu Pro Leu Gln Pro Gly
        610                 615                 620

Leu Val Tyr Glu Thr Asn Asn Val Asp Tyr Leu Asn Tyr Leu Cys Tyr
625                 630                 635                 640

Asn Gly Leu Asn Ile Thr Met Ile Lys Val Ile Ser Gly Thr Val Pro
                645                 650                 655

Glu Asn Phe Asn Cys Pro Lys Asp Ser Ser Ser Asp Leu Ile Ser Ser
                660                 665                 670

Ile Asn Tyr Pro Ser Ile Ala Val Asn Phe Thr Gly Lys Ala Asp Ala
            675                 680                 685

Val Val Ser Arg Thr Val Thr Asn Val Asp Glu Glu Asp Glu Thr Val
        690                 695                 700

Tyr Phe Pro Val Val Glu Ala Pro Ser Glu Val Ile Val Thr Leu Phe
705                 710                 715                 720

Pro Tyr Asn Leu Glu Phe Thr Thr Ser Ile Lys Lys Gln Ser Tyr Asn
                725                 730                 735

Ile Thr Phe Arg Pro Lys Thr Ser Leu Lys Lys Asp Leu Phe Gly Ser
                740                 745                 750

Ile Thr Trp Ser Asn Asp Lys Tyr Met Val Arg Ile Pro Phe Val Leu
            755                 760                 765

Thr Lys
    770
```